US011130782B2

(12) United States Patent
Love

(10) Patent No.: US 11,130,782 B2
(45) Date of Patent: Sep. 28, 2021

(54) NICOTINIC ACETYLCHOLINE RECEPTOR PEPTIDE ANTAGONIST CONOTOXIN COMPOSITIONS AND RELATED METHODS

(71) Applicant: Glo Pharma, Inc., Encinitas, CA (US)

(72) Inventor: Robert A. Love, San Diego, CA (US)

(73) Assignee: GLO PHARMA, INC.

(*) Notice: Subject to any disclaimer, the term of this patent is extended or adjusted under 35 U.S.C. 154(b) by 0 days.

(21) Appl. No.: 16/653,724

(22) Filed: Oct. 15, 2019

(65) Prior Publication Data
US 2020/0115414 A1 Apr. 16, 2020

Related U.S. Application Data

(60) Provisional application No. 62/867,128, filed on Jun. 26, 2019, provisional application No. 62/746,398, filed on Oct. 16, 2018.

(51) Int. Cl.
*C07K 7/08* (2006.01)
*A61Q 19/08* (2006.01)
*A61K 8/64* (2006.01)
*A61K 38/00* (2006.01)

(52) U.S. Cl.
CPC ............... *C07K 7/08* (2013.01); *A61K 8/64* (2013.01); *A61Q 19/08* (2013.01); *A61K 38/00* (2013.01)

(58) Field of Classification Search
CPC .......... A61K 38/00; A61K 8/64; A61Q 19/08; C07K 7/08; C07K 14/43504
See application file for complete search history.

(56) References Cited

U.S. PATENT DOCUMENTS

| | | | |
|---|---|---|---|
| 4,447,356 A | 5/1984 | Olivera | |
| 5,846,514 A | 12/1998 | Foster et al. | |
| 6,268,473 B1 * | 7/2001 | Olivera | A61P 21/00 530/325 |
| 6,334,997 B1 | 1/2002 | Foster et al. | |
| 7,964,630 B2 | 6/2011 | Imfeld et al. | |
| 8,735,541 B2 | 5/2014 | Watkins et al. | |
| 9,550,808 B2 | 1/2017 | Zhmak et al. | |
| 9,815,875 B2 | 11/2017 | Peters et al. | |
| 2015/0361137 A1 | 12/2015 | Zhmak et al. | |

FOREIGN PATENT DOCUMENTS

| | | |
|---|---|---|
| EP | 1180524 B1 | 8/2006 |
| EP | 2945963 B1 | 3/2017 |
| WO | WO-9921878 A1 | 5/1999 |
| WO | WO-2006047900 A2 | 5/2006 |
| WO | WO-2013062444 A1 | 5/2013 |
| WO | WO-2017102588 A1 | 6/2017 |
| WO | WO-2020081583 A1 | 4/2020 |

OTHER PUBLICATIONS

Croskey et al. "Evaluation of the Impact of Proline on the Folding of alpha-Conotoxins" Kern Ind, vol. 53, Nos. 7-8, pp. 333-338. (Year: 2004).*
Hargittai. "Conotoxins: Disulfide-rich Small Peptides", Kern Ind, vol. 53, Nos. 7-8, pp. 343-348. (Year: 2004).*
Nishiuchi et al. Primary and secondary structure of conotoxin GI, a neurotoxic tridecapeptide from a marine snail. FEBS Letters, vol. 148, No. 2, pp. 260-262. (Year: 1982).*
Liu et al. Two Potent α3/5 Conotoxins from Piscivorous Conus achatinus,Acta Biochimica et Biophysica Sinica 2007, Vo. 39, No. 6, pp. 438-444. (Year: 2007).*
Hashimoto et al. Structure-Activity Relations of Conotoxins at the Neuromuscular Junction. European Journal of Pharmacology, vol. 118, pp. 351-354. (Year: 1985).*
Thermo. Technical Information. N-terminal Acetylation and C-terminal Amidation of Peptides. 2 pages. (Year: 2004).*
Blanchfield et al. Synthesis, Structure Elucidation, in Vitro Biological Activity, Toxicity, and Caco-2 Cell Permeability of Lipophilic Analogues of r-Conotoxin MII. J Med Chem, 2003, vol. 46, pp. 1266-1272. (Year: 2003).*
Kasheverov et al. alpha-Conotoxin analgs with additional positive charge show increased selectivity towrads Torpedo californica and some neuronal subtypes of nicotinic acetylcholine receptors. The FEBS Journal, 2006. vol. 273, pp. 4470-4481. (Year: 2006).*
Albuquerque et al.: Mammalian Nicotinic Acetylcholine Receptors: From Structure to Function. Physiol. Rev. 89(1):73-120 (2009).
Almeda et al.: Snake Venom Peptides and Low Mass Proteins: Molecular Tools and Therapeutic Agents. Current Medicinal Chemistry. 23:1-29 (2016).
Armishaw et al.: A Synthetic Combinatorial Strategy for Developing α-Conotoxin Analogs as Potent α7 Nicotinic Acetylcholine Receptor Antagonists. The Journal of Biological Chemistry. 285(3):1809-1821 (2010).
Atassi et al.: Mapping by Synthetic Peptides of the Binding Sites for Acetylcholine Receptor on α-Bungarotoxin. Journal of Protein Chemistry. 7(5):655-656 (1988).
Berge et al.: Pharmaceutical Salts. Journal of Pharmaceutical Science. 66:1-19 (1997).
BOTOX Cosmetic BLA 103000. Reference ID 4263846 product label for Botox Cosmetic. 22 pages, revised May 2018.
BOTOX: Reference ID 4086832 Manufactured by Allergan Pharmaceuticals. 37 pages (2017).
Bundgaard. Design of Prodrugs. 7 9:21 24 (1985).
Chan et al.: Discovery of a Potent and Selective α3β4 Nicotinic Acetylcholine Receptor Antagonist from an α-Conotoxin Synthetic Combinatorial Library. Journal of Medicinal Chemistry. 57:3511-3521 (2014).

(Continued)

Primary Examiner — Marcela M Cordero Garcia
(74) Attorney, Agent, or Firm — Wilson Sonsini Goodrich & Rosati

(57) ABSTRACT

The present invention relates to novel peptide antagonists that inhibit binding of acetylcholine to the active site of the muscle-type nicotinic acetylcholine receptor. The peptide antagonists of the invention are useful in cosmetic compositions that prevent or improve the appearance of skin wrinkles and related skin conditions. The invention further relates to cosmetic and pharmaceutical compositions comprising a peptide antagonist of the invention, and methods for their use.

17 Claims, No Drawings
Specification includes a Sequence Listing.

(56) References Cited

OTHER PUBLICATIONS

Dekan et al.: α-Conotoxin Iml incorporating stable cystathionine bridges maintains full potency and identical three-dimensional structure. J. Am. Chem. Soc. 133: 15866-15869 (2011).
DiMarco et al.: Discovery of novel, highly potent and selective b-hairpin mimetic CXCR4 inhibitors with excellent anti-HIV activity and pharmacokinetic profiles. Bioorganic & Medicinal Chemistry 14: 8396-8404 (2006).
DSM Bright Science. Brighter Living. SYN®-Ake Product Data Sheet. 3 pages (2015).
Dysport BLA 125274. Reference ID 4111174 product labeling for Dysport. 32 pages, revised Jun. 2017.
Holtman et al., The novel small molecule α9α10 nicotinic acetylcholine receptor antagonist ZZ-204G is analgesic. European Journal of Pharmacology 670(2-3):500-508 (2011).
Hsiao et al.: rotein Engineering of Venom Toxins by Synthetic Aproach and NMR Dynamic Simulation: Status of BAsic Amino Acid Residues in Waglerin I. Riochemical and Biophysical research Communications 227(1467):59-63 (1996).
JEUVEAU. Reference ID 4461637 product label. 8 pages, revised Jul. 2019.
Kalamida et al.: Muscle and neuronal nicotinic acetylcholine receptors. The FEBS Journal 274:3799-3845 (2007).
Kim et al.: Amino acid sequences of two novel long-chain neurotoxins from the venom of the sea snake Laticauda colubrina. Biochem. J. 207: 215-223 (1982).
Knerr et al.: Synthesis and activity of thioether-containing analogues of the complement inhibitor compstatin. ACS Chem Biol. 6(7): 753-760 (2011).
Kyte et al.: A simple method for displaying the hydropathic character of a protein. J. Mol. Biol. 157:105-131 (1982).
Lebbe et al.: Conotoxins Targeting Nicotinic Acetylcholine Receptors: An Overview. Marine Drugs. ISSN 1660:3397. 12:2970-3004 (2014).
Lebbe et al.: Structure-Function Elucidation of a New α-Conotoxin, Lo1a, from Conus longurionis. The Journal of Biological Chemistry. 289(14):9573-9583 (2014).

McDaniel et al.: A Novel Peptide Mimicking the Interaction of α-Neurotoxins with Acetylcholine Receptor. Journal of Protein Chemistry. 6(5):455-461 (1987).
McIntosh et al., Alpha-conotoxin GIC from Conus geographus, a novel peptide antagonist of nicotinic acetylcholine receptors. Journal of Biological Chemistry 277(37):33610-33615 (2002).
Nguyen et al.: Making circles: recent advance in chemical and enzymatic approaches in peptide macrocyclization. Journal of Biochemistry and Chemical Sciences 1(1): 1-13 (2017).
PCT/US2019/056360 International Search Report and Written Opinion dated Feb. 24, 2020.
Peigneur et al.: Struture-Function Elucidation of a New α-Conotoxin, MilIA, from Conus milnedwardsi. Marine Drugs (MDPI). 17(535):16 pages (2019).
Pentapharm Sny®-Ake Product Description. Four Pages 2020.
Sellin et al.: Conformational Analysis of a Toxic Peptide from Trimeresurus wagleri which Blocks the Nicotinic Acetylcholine Receptor. Biophysical Journal. vol. 70. p. 3-13 (1996).
Shelukhina et al., Azemiopsin, a selective peptide antagonist of muscle nicotinic acetylcholine receptor: preclinical evaluation as a local muscle relaxant. Toxins (Basel) 10(1):1-25 pii: E34. doi: 10.3390/toxins10010034 (2018).
Spicer et al.: Selective chemical protein modification. Nature Communications 5: 4740 (2014).
Tam et al.: Chemical Synthesis of Circular Proteins. The Journal of Biological Chemistry 287(32): 27020-27025 (2012).
Thakre: Snake Venom Peptides Use in Anti-Ageining Products. International Journal of Science and Research (IJSR). ISSN (Online): 2319-7065. 7(1): 53-58 (2018).
Thapa et al.: Conotoxins and their Regulatory Considerations. Pharmaceutical Regulatory Affairs: Open Access. Pharmaceut Reg Affairs. 3:3 1-6 (2014).
Utkin et al.: Azemiopsin from Azemiops feae Viper Venom, a Novel Polypeptide Ligand of Nicotinic Acetylcholine Receptor, J. of Biol. Chem. 287(32):27079-27086 (2012).
Xeomin BLA 125360. Reference ID 4286266 product labeling for Xeomin. 20 pages, revised Jul. 2018.

* cited by examiner

```
                      SEQUENCE LISTING

<160> NUMBER OF SEQ ID NOS: 79

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Glu Cys Cys Asn Pro Ala Cys Gly Arg His Tyr Ser Cys
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Cys Cys Asn Pro Ala Cys Gly Lys His Phe Ser Cys
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 3

Gly Arg Cys Cys His Pro Ala Cys Gly Lys Asn Tyr Ser Cys
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Cys Lys Pro Ala Cys Gly Lys Asn Tyr Ser Cys
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 5

Cys Xaa Arg Pro Ala Cys Gly His Asn Tyr Ser Xaa
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 6

Cys Xaa His Pro Ala Cys Gly His Asn Tyr Ser Xaa
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (2)..(2)
```

```
<223> OTHER INFORMATION: Cyt
<220> FEATURE:
<221> NAME/KEY: MOD_RES
<222> LOCATION: (6)..(6)
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 7

Xaa Xaa Lys Pro Ala Xaa Gly Lys Gln Tyr Ser Xaa
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Cys Arg Pro Ala Cys Gly Lys Gln Tyr Ser Cys
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (6)..(6)
<223> OTHER INFORMATION: Cyt

<400> SEQUENCE: 9

Xaa Cys His Pro Ala Xaa Gly Lys Gln Tyr Ser Cys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (6)..(6)
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 10

Xaa Xaa His Pro Ala Xaa Gly Arg Gln Tyr Ser Xaa
```

```
<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 11

Cys Xaa His Pro Ala Cys Gly Arg Asn Tyr Ser Xaa
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Cys Arg Pro Ala Cys Gly Arg Asn Tyr Ser Cys
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (6)..(6)
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 13

Xaa Xaa Lys Pro Ala Xaa Gly Arg Asn Tyr Ser Xaa
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Sec
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (6)..(6)
<223> OTHER INFORMATION: Sec
<220> FEATURE:
<221> NAME/KEY: MOD_RES
<222> LOCATION: (12)..(12)
<223> OTHER INFORMATION: Cyt

<400> SEQUENCE: 14

Xaa Xaa Lys Pro Ala Xaa Gly Lys Asn Tyr Ser Xaa
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (6)..(6)
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 15

Xaa Xaa His Pro Ala Xaa Gly Lys Asn Tyr Ser Xaa
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (6)..(6)
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 16

Xaa Xaa His Pro Ala Xaa Gly Lys Asn Tyr Ser Xaa
1               5                   10
```

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sec
<220> FEATURE:
<221> NAME/KEY: MOD_RES
<222> LOCATION: (2)..(2)
<223> OTHER INFORMATION: Sec
<220> FEATURE:
<221> NAME/KEY: MOD_RES
<222> LOCATION: (6)..(6)
<223> OTHER INFORMATION: Sec
<220> FEATURE:
<221> NAME/KEY: MOD_RES
<222> LOCATION: (12)..(12)
<223> OTHER INFORMATION: Sec

<400> SEQUENCE: 17

Xaa Xaa Asn Pro Ala Xaa Gly Arg His Tyr Ser Xaa
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (6)..(6)
<223> OTHER INFORMATION: Cyt

<400> SEQUENCE: 18

Xaa Cys Asn Pro Ala Xaa Gly Arg His Tyr Ser Cys
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Cys Cys Gln Pro Ala Cys Gly Lys His Tyr Ser Cys
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cyt
<220> FEATURE:

```
<221> NAME/KEY: MOD_RES
<222> LOCATION: (6)..(6)
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 20

Cys Xaa Asn Pro Ala Xaa Gly Lys His Tyr Ser Xaa
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (6)..(6)
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 21

Xaa Xaa Asn Pro Ala Xaa Gly Arg His Tyr Ser Xaa
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (6)..(6)
<223> OTHER INFORMATION: Cyt

<400> SEQUENCE: 22

Xaa Cys Asn Pro Ala Xaa Gly Arg His Tyr Ser Cys
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
```

```
<222> LOCATION: (12)..(12)
<223> OTHER INFORMATION: Cyt

<400> SEQUENCE: 23

Cys Xaa Asn Pro Ala Cys Gly Lys His Tyr Ser Xaa
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (6)..(6)
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 24

Xaa Xaa Asn Pro Ala Xaa Gly Lys His Tyr Ser Xaa
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (6)..(6)
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 25

Xaa Xaa Asn Pro Ala Xaa Gly Arg His Tyr Ser Xaa
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Cyt
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (6)..(6)
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 26

Xaa Xaa Asn Pro Ala Xaa Gly Arg His Tyr Ser Xaa
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (3)..(3)
<223> OTHER INFORMATION: Cyt
<220> FEATURE:
<221> NAME/KEY: MOD_RES
<222> LOCATION: (7)..(7)
<223> OTHER INFORMATION: Cyt
<220> FEATURE:
<221> NAME/KEY: MOD_RES
<222> LOCATION: (13)..(13)
<223> OTHER INFORMATION: Cyt

<400> SEQUENCE: 27

Arg Xaa Xaa His Pro Ala Xaa Gly Lys Asn Tyr Ser Xaa
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (3)..(3)
<223> OTHER INFORMATION: Cyt
<220> FEATURE:
<221> NAME/KEY: MOD_RES
<222> LOCATION: (7)..(7)
<223> OTHER INFORMATION: Cyt
<220> FEATURE:
<221> NAME/KEY: MOD_RES
<222> LOCATION: (13)..(13)
<223> OTHER INFORMATION: Cyt

<400> SEQUENCE: 28

Arg Xaa Xaa His Pro Ala Xaa Gly Lys Asn Tyr Ser Xaa
1               5                   10
```

```
<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Cys Cys His Pro Ala Cys Gly Lys Asn Tyr Ser Cys
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Cyt
<220> FEATURE:
<221> NAME/KEY: MOD_RES
<222> LOCATION: (13)..(13)
<223> OTHER INFORMATION: Cyt

<400> SEQUENCE: 30

Arg Cys Xaa Lys Pro Ala Cys Gly Lys Asn Tyr Ser Xaa
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Cyt
<220> FEATURE:
<221> NAME/KEY: MOD_RES
<222> LOCATION: (13)..(13)
<223> OTHER INFORMATION: Cyt

<400> SEQUENCE: 31

Arg Cys Xaa His Pro Ala Cys Gly Lys Asn Tyr Ser Xaa
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (7)..(7)
<223> OTHER INFORMATION: Cyt

<400> SEQUENCE: 32

Arg Xaa Cys His Pro Ala Xaa Gly Arg Asn Tyr Ser Cys
1               5                   10
```

```
<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (3)..(3)
<223> OTHER INFORMATION: Cyt
<220> FEATURE:
<221> NAME/KEY: MOD_RES
<222> LOCATION: (7)..(7)
<223> OTHER INFORMATION: Cyt
<220> FEATURE:
<221> NAME/KEY: MOD_RES
<222> LOCATION: (13)..(13)
<223> OTHER INFORMATION: Cyt

<400> SEQUENCE: 33

Arg Xaa Xaa Arg Pro Ala Xaa Gly Lys Asn Tyr Ser Xaa
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (3)..(3)
<223> OTHER INFORMATION: Cyt
<220> FEATURE:
<221> NAME/KEY: MOD_RES
<222> LOCATION: (7)..(7)
<223> OTHER INFORMATION: Cyt
<220> FEATURE:
<221> NAME/KEY: MOD_RES
<222> LOCATION: (13)..(13)
<223> OTHER INFORMATION: Cyt

<400> SEQUENCE: 34

Arg Xaa Xaa His Pro Ala Xaa Gly His Asn Tyr Ser Xaa
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (3)..(3)
<223> OTHER INFORMATION: Cyt
<220> FEATURE:
<221> NAME/KEY: MOD_RES
```

```
<222> LOCATION: (7)..(7)
<223> OTHER INFORMATION: Cyt
<220> FEATURE:
<221> NAME/KEY: MOD_RES
<222> LOCATION: (13)..(13)
<223> OTHER INFORMATION: Cyt

<400> SEQUENCE: 35

Arg Xaa Xaa Arg Pro Ala Xaa Gly Lys Asn Tyr Ser Xaa
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Sec
<220> FEATURE:
<221> NAME/KEY: MOD_RES
<222> LOCATION: (3)..(3)
<223> OTHER INFORMATION: Sec
<220> FEATURE:
<221> NAME/KEY: MOD_RES
<222> LOCATION: (7)..(7)
<223> OTHER INFORMATION: Sec
<220> FEATURE:
<221> NAME/KEY: MOD_RES
<222> LOCATION: (13)..(13)
<223> OTHER INFORMATION: Sec

<400> SEQUENCE: 36

Arg Xaa Xaa His Pro Ala Xaa Gly Lys Asn Tyr Ser Xaa
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (3)..(3)
<223> OTHER INFORMATION: Cyt
<220> FEATURE:
<221> NAME/KEY: MOD_RES
<222> LOCATION: (7)..(7)
<223> OTHER INFORMATION: Cyt
<220> FEATURE:
<221> NAME/KEY: MOD_RES
<222> LOCATION: (13)..(13)
<223> OTHER INFORMATION: Cyt

<400> SEQUENCE: 37

Lys Xaa Xaa His Pro Ala Xaa Gly Lys Asn Tyr Ser Xaa
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
```

```
                        peptide
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (3)..(3)
<223> OTHER INFORMATION: Cyt
<220> FEATURE:
<221> NAME/KEY: MOD_RES
<222> LOCATION: (7)..(7)
<223> OTHER INFORMATION: Cyt
<220> FEATURE:
<221> NAME/KEY: MOD_RES
<222> LOCATION: (13)..(13)
<223> OTHER INFORMATION: Cyt

<400> SEQUENCE: 38

Lys Xaa Xaa His Pro Ala Xaa Gly Arg Asn Tyr Ser Xaa
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (6)..(6)
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 39

Xaa Xaa His Pro Ala Xaa Gly Arg His Tyr Ser Xaa
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Cys Cys Lys Pro Ala Cys Gly Arg His Tyr Ser Cys
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cyt
```

```
<220> FEATURE:
<221> NAME/KEY: MOD_RES
<222> LOCATION: (12)..(12)
<223> OTHER INFORMATION: Cyt

<400> SEQUENCE: 41

Cys Xaa His Pro Ala Cys Gly Arg His Tyr Ser Xaa
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 42

Cys Xaa His Pro Ala Cys Gly Arg His Tyr Ser Xaa
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (6)..(6)
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 43

Xaa Xaa His Pro Ala Xaa Gly Lys His Tyr Ser Xaa
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (2)..(2)
<223> OTHER INFORMATION: Cyt
<220> FEATURE:
```

```
<221> NAME/KEY: MOD_RES
<222> LOCATION: (6)..(6)
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 44

Xaa Xaa His Pro Ala Xaa Gly Arg His Tyr Ser Xaa
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (6)..(6)
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 45

Xaa Xaa His Pro Ala Xaa Gly Lys His Tyr Ser Xaa
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (6)..(6)
<223> OTHER INFORMATION: Cyt

<400> SEQUENCE: 46

Xaa Cys His Pro Ala Xaa Gly Arg Lys Tyr Ser Cys
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
```

<222> LOCATION: (6)..(6)
<223> OTHER INFORMATION: Cyt

<400> SEQUENCE: 47

Xaa Cys His Pro Ala Xaa Gly Arg Lys Tyr Ser Cys
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (6)..(6)
<223> OTHER INFORMATION: Cyt

<400> SEQUENCE: 48

Xaa Cys His Pro Ala Xaa Gly Arg Lys Tyr Ser Cys
1               5                   10

<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (6)..(6)
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 49

Xaa Xaa His Pro Ala Xaa Gly Arg His Tyr Ser Xaa
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (6)..(6)

```
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 50

Xaa Xaa Lys Pro Ala Xaa Gly Arg His Tyr Ser Xaa
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Sec
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (6)..(6)
<223> OTHER INFORMATION: Sec
<220> FEATURE:
<221> NAME/KEY: MOD_RES
<222> LOCATION: (12)..(12)
<223> OTHER INFORMATION: Cyt

<400> SEQUENCE: 51

Xaa Xaa His Pro Ala Xaa Gly Lys His Tyr Ser Xaa
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (2)..(2)
<223> OTHER INFORMATION: Sec
<220> FEATURE:
<221> NAME/KEY: MOD_RES
<222> LOCATION: (6)..(6)
<223> OTHER INFORMATION: Cyt
<220> FEATURE:
<221> NAME/KEY: MOD_RES
<222> LOCATION: (12)..(12)
<223> OTHER INFORMATION: Sec

<400> SEQUENCE: 52

Xaa Xaa His Pro Ala Xaa Gly Arg His Tyr Ser Xaa
1               5                   10

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 53

Trp Tyr Pro Lys Pro
1               5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Pro Arg Pro Ala
1               5

<210> SEQ ID NO 55
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Cys Lys Met Trp Ala Asp Ala Phe Thr Ser Ser Arg Gly Lys Val Val
1               5                   10                  15

Glu Cys Gly

<210> SEQ ID NO 56
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Glu Cys Cys His Pro Ala Cys Gly Lys His Phe Ser Cys
1               5                   10

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asp Asn Trp Trp Pro Lys Arg Pro His
1               5

<210> SEQ ID NO 58
<211> LENGTH: 74
<212> TYPE: PRT
<213> ORGANISM: Bungarus multicinctus

<400> SEQUENCE: 58

Ile Val Cys His Thr Thr Ala Thr Ser Pro Ile Ser Ala Val Thr Cys
1               5                   10                  15

Pro Pro Gly Glu Asn Leu Cys Tyr Arg Lys Met Trp Cys Asp Ala Phe
            20                  25                  30

Cys Ser Ser Arg Gly Lys Val Val Glu Leu Gly Cys Ala Ala Thr Cys
```

```
                35                  40                  45
Pro Ser Lys Lys Pro Tyr Glu Glu Val Thr Cys Cys Ser Thr Asp Lys
    50                  55                  60
Cys Asn Pro His Pro Lys Gln Arg Pro Gly
65                  70

<210> SEQ ID NO 59
<211> LENGTH: 69
<212> TYPE: PRT
<213> ORGANISM: Laticauda colubrina

<400> SEQUENCE: 59

Arg Ile Cys Tyr Leu Ala Pro Arg Asp Thr Gln Ile Cys Ala Pro Gly
1               5                   10                  15

Gln Glu Ile Cys Tyr Leu Lys Ser Trp Asp Asp Gly Thr Gly Phe Leu
            20                  25                  30

Lys Gly Asn Arg Leu Glu Phe Gly Cys Ala Ala Thr Cys Pro Thr Val
        35                  40                  45

Lys Pro Gly Ile Asp Ile Lys Cys Cys Ser Thr Asp Lys Cys Asn Pro
    50                  55                  60

His Pro Lys Leu Ala
65

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Cys Cys Asn Pro Ala Cys Gly Lys Asn Tyr Ser Cys
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Cys Cys His Pro Ala Cys Gly Arg His Tyr Ser Cys
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Cys Cys Asn Pro Ala Cys Gly Lys Asn Tyr Lys Cys
1               5                   10

<210> SEQ ID NO 63
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (6)..(6)
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 63

Xaa Xaa Asn Pro Ala Xaa Gly Lys Asn Tyr Ser Xaa
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (6)..(6)
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 64

Xaa Xaa His Pro Ala Xaa Gly Arg His Tyr Ser Xaa
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (6)..(6)
<223> OTHER INFORMATION: Cyt
<220> FEATURE:
<221> NAME/KEY: MOD_RES
<222> LOCATION: (12)..(12)
<223> OTHER INFORMATION: Cyt
```

<400> SEQUENCE: 65

Xaa Xaa Asn Pro Ala Xaa Gly Lys Asn Tyr Lys Xaa
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 66

Cys Xaa Asn Pro Ala Cys Gly Lys Asn Tyr Ser Xaa
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 67

Cys Xaa His Pro Ala Cys Gly Arg His Tyr Ser Xaa
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 68

Cys Xaa Asn Pro Ala Cys Gly Lys Asn Tyr Lys Xaa
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (6)..(6)
<223> OTHER INFORMATION: Cyt

<400> SEQUENCE: 69

Xaa Cys Asn Pro Ala Xaa Gly Lys Asn Tyr Ser Cys
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (6)..(6)
<223> OTHER INFORMATION: Cyt

<400> SEQUENCE: 70

Xaa Cys His Pro Ala Xaa Gly Arg His Tyr Ser Cys
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (6)..(6)
<223> OTHER INFORMATION: Cyt

<400> SEQUENCE: 71

Xaa Cys Asn Pro Ala Xaa Gly Lys Asn Tyr Lys Cys
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (7)..(7)
<223> OTHER INFORMATION: Cyt

<400> SEQUENCE: 72

Arg Xaa Cys His Pro Ala Xaa Gly Lys Asn Tyr Ser Cys
1               5                   10
```

```
<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Cyt
<220> FEATURE:
<221> NAME/KEY: MOD_RES
<222> LOCATION: (13)..(13)
<223> OTHER INFORMATION: Cyt

<400> SEQUENCE: 73

Arg Cys Xaa His Pro Ala Cys Gly Lys Asn Tyr Ser Xaa
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Arg Cys Cys His Pro Ala Cys Gly Lys Asn Tyr Ser Cys
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (3)..(3)
<223> OTHER INFORMATION: Cyt
<220> FEATURE:
<221> NAME/KEY: MOD_RES
<222> LOCATION: (7)..(7)
<223> OTHER INFORMATION: Cyt
<220> FEATURE:
<221> NAME/KEY: MOD_RES
<222> LOCATION: (13)..(13)
<223> OTHER INFORMATION: Cyt

<400> SEQUENCE: 75

Arg Xaa Xaa His Pro Ala Xaa Gly Lys Asn Tyr Ser Xaa
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Cyt
```

```
<220> FEATURE:
<221> NAME/KEY: MOD_RES
<222> LOCATION: (12)..(12)
<223> OTHER INFORMATION: Cyt

<400> SEQUENCE: 76

Cys Xaa His Pro Ala Cys Gly Lys Asn Tyr Ser Xaa
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (2)..(2)
<223> OTHER INFORMATION: Cyt
<220> FEATURE:
<221> NAME/KEY: MOD_RES
<222> LOCATION: (6)..(6)
<223> OTHER INFORMATION: Cyt
<220> FEATURE:
<221> NAME/KEY: MOD_RES
<222> LOCATION: (12)..(12)
<223> OTHER INFORMATION: Cyt

<400> SEQUENCE: 77

Xaa Xaa His Pro Ala Xaa Gly Lys Asn Tyr Ser Xaa
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Cys Cys His Pro Ala Cys Gly Lys Asn Tyr Ser Cys
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cyt
<220> FEATURE:
<221> NAME/KEY: MOD_RES
<222> LOCATION: (6)..(6)
<223> OTHER INFORMATION: Cyt

<400> SEQUENCE: 79

Xaa Cys His Pro Ala Xaa Gly Lys Asn Tyr Ser Cys
1               5                   10
```

US 11,130,782 B2

NICOTINIC ACETYLCHOLINE RECEPTOR PEPTIDE ANTAGONIST CONOTOXIN COMPOSITIONS AND RELATED METHODS

CROSS-REFERENCE TO RELATED APPLICATIONS

This application claims the benefit of U.S. Provisional Application Ser. No. 62/867,128 filed Jun. 26, 2019 and U.S. Provisional Application Ser. No. 62/746,398 filed Oct. 16, 2018, which applications are incorporated herein by reference.

SEQUENCE LISTING

The instant application contains a Sequence Listing which has been submitted electronically in ASCII format and is hereby incorporated by reference in its entirety. Said ASCII copy, created on Oct. 9, 2019, is named 54780-703_201_SL.txt and is 30,738 bytes in size.

BACKGROUND OF THE INVENTION

Muscle-type nicotinic acetylcholine receptors in vertebrate skeletal muscles mediate neuromuscular transmission at the neuromuscular junction. They respond to the binding of acetylcholine to cause muscle contraction.

SUMMARY OF THE INVENTION

The present invention includes compositions and methods relating to novel peptide antagonists that inhibit binding of acetylcholine (ACh) to the active site of the muscle-type nicotinic acetylcholine receptor (muscle nAChR). In some embodiments, the invention includes cosmetic or pharmaceutical compositions comprising a peptide antagonist of the invention. In some embodiments, the peptide antagonists of the invention are useful in topical cosmetic or pharmaceutical compositions for preventing or improving of the appearance of skin wrinkles or related skin conditions. In some embodiments, the invention relates to pharmaceutical compositions for preventing or treating a disorder ameliorated by inhibition of muscle nAChR, e.g., migraine headache. In some embodiments, the invention relates to methods of using a cosmetic or pharmaceutical composition comprising a peptide antagonist of the invention. In some embodiments, the invention relates to methods for blocking or inhibiting neuromuscular transmission and/or ACh binding to muscle nAChR using a compositions or method of the invention.

The present invention includes a muscle-type nicotinic acetylcholine receptor peptide antagonist comprising an amino acid sequence Xaa1-Xaa2-Xaa3-Xaa4-Xaa5-Xaa6-Xaa7-Xaa8-Xaa9-Xaa10-Xaa11-Xaa12-Xaa13-Xaa14, wherein: Xaa1 is absent or selected from Ala, Gly, Val, Leu, Ile and a derivative of Ala, Gly, Val, Leu, or Ile; Xaa2 is absent or selected from: Asn, Asp, Gln, Glu, Arg, His, Lys, Phe, Trp, Tyr, Ala, Gly, Val, Leu, Ile, and a derivative of Asn, Asp, Gln, Glu, Arg, His, Lys, Phe, Trp, Tyr, Ala, Gly, Val, Leu, or Ile; Xaa3 and Xaa8 form a linkage Xaa3-Xaa8; Xaa4 and Xaa14 form a linkage Xaa4-Xaa14; Xaa5 is selected from: Asn, Asp, Gln, Glu, Arg, His, Lys, and a derivative of Asn, Asp, Gln, Glu, Arg, His, or Lys; Xaa6 is selected from: Pro and a derivative thereof; Xaa7 is selected from: Ala, Gly, Val, Leu, Ile and a derivative of Ala, Gly, Val, Leu, or Ile; Xaa9 is selected from: Ala, Gly, Val, Leu, Ile and a derivative of Ala, Gly, Val, Leu, or Ile; Xaa10 is selected from: Arg, His, Lys, and a derivative of Arg, His, or Lys; Xaa11 is selected from: Asn, Asp, Gln, Glu, Arg, His, Lys, and a derivative of Asn, Asp, Gln, Glu, Arg, His, or Lys; Xaa12 is selected from: Phe, Trp, Tyr, and a derivative of Phe, Trp, or Tyr; Xaa13 is selected from: Cys, Met, Sec, Ser, Thr, Arg, His, Lys, and a derivative of Cys, Met, Sec, Ser, Thr, Arg, His, or Lys; the N-terminus is optionally modified; and the C-terminus is optionally modified.

In some embodiments, the muscle-type nicotinic acetylcholine receptor peptide antagonist is the muscle-type nicotinic acetylcholine receptor peptide antagonist as initially set forth, wherein: Xaa1 is absent; Xaa2 is absent; the Xaa3-Xaa8 linkage is selected from: a Cys-Cys linkage, a Sec-Sec linkage, a cystathionine linkage, a lactam bridge, a thioether linkage, and a dicarba linkage; the Xaa4-Xaa14 linkage is selected from: a Cys-Cys linkage, a Sec-Sec linkage, a cystathionine linkage, a lactam bridge, a thioether linkage, and a dicarba linkage; Xaa5 is selected from: Asn, Asp, Gln, Glu, and a derivative of Asn, Asp, Gln, or Glu; Xaa6 is selected from: Pro and a derivative thereof; Xaa7 is selected from: Ala, Gly, Val, Leu, Ile and a derivative of Ala, Gly, Val, Leu, or Ile; Xaa9 is selected from: Ala, Gly, Val, Leu, Ile and a derivative of Ala, Gly, Val, Leu, or Ile; Xaa10 is selected from: Arg, His, Lys, and a derivative of Arg, His, or Lys; Xaa11 is selected from: Arg, His, Lys, and a derivative of Arg, His, or Lys; Xaa12 is selected from: Phe, Trp, Tyr, and a derivative of Phe, Trp, or Tyr; and Xaa13 is selected from: Cys, Met, Sec, Ser, Thr, and a derivative of Cys, Met, Sec, Ser, or Thr.

In some embodiments, the muscle-type nicotinic acetylcholine receptor peptide antagonist is the muscle-type nicotinic acetylcholine receptor peptide antagonist as initially set forth, wherein: Xaa1 is absent; Xaa2 is absent; the Xaa3-Xaa8 linkage is selected from: a Cys-Cys linkage, a Sec-Sec linkage, a cystathionine linkage, a lactam bridge, a thioether linkage, and a dicarba linkage; the Xaa4-Xaa14 linkage is selected from: a Cys-Cys linkage, a Sec-Sec linkage, a cystathionine linkage, a lactam bridge, a thioether linkage, and a dicarba linkage; Xaa5 is selected from: Arg, His, Lys, and a derivative of Arg, His, or Lys; Xaa6 is selected from: Pro and a derivative thereof; Xaa7 is selected from: Ala, Gly, Val, Leu, Ile and a derivative of Ala, Gly, Val, Leu, or Ile; Xaa9 is selected from: Ala, Gly, Val, Leu, Ile and a derivative of Ala, Gly, Val, Leu, or Ile; Xaa10 is selected from: Arg, His, Lys, and a derivative of Arg, His, or Lys; Xaa11 is selected from: Asn, Asp, Gln, Glu, and a derivative of Asn, Asp, Gln, or Glu; Xaa12 is selected from: Phe, Trp, Tyr, and a derivative of Phe, Trp, or Tyr; and Xaa13 is selected from: Cys, Met, Sec, Ser, Thr, and a derivative of Cys, Met, Sec, Ser, or Thr.

In some embodiments, the muscle-type nicotinic acetylcholine receptor peptide antagonist is the muscle-type nicotinic acetylcholine receptor peptide antagonist as initially set forth, wherein: Xaa1 is absent; Xaa2 is selected from: Arg, His, Lys, and a derivative of Arg, His, or Lys; the Xaa3-Xaa8 linkage is selected from: a Cys-Cys linkage, a Sec-Sec linkage, a cystathionine linkage, a lactam bridge, a thioether linkage, and a dicarba linkage; the Xaa4-Xaa14 linkage is selected from: a Cys-Cys linkage, a Sec-Sec linkage, a cystathionine linkage, a lactam bridge, a thioether linkage, and a dicarba linkage; Xaa5 is selected from: Arg, His, Lys, and a derivative of Arg, His, or Lys; Xaa6 is selected from: Pro and a derivative thereof; Xaa7 is selected from: Ala, Gly, Val, Leu, Ile and a derivative of Ala, Gly, Val, Leu, or Ile; Xaa9 is selected from: Ala, Gly, Val, Leu, Ile and a derivative of Ala, Gly, Val, Leu, or Ile; Xaa10 is selected from: Arg, His, Lys, and a derivative of Arg, His, or Lys; Xaa11 is selected from: Asn, Asp, Gln, Glu, and a derivative of Asn, Asp, Gln, or Glu; Xaa12 is selected from: Phe, Trp, Tyr, and a derivative of Phe, Trp, or Tyr; and Xaa13 is selected from: Cys, Met, Sec, Ser, Thr, and a derivative of Cys, Met, Sec, Ser, or Thr.

In some embodiments, the muscle-type nicotinic acetylcholine receptor peptide antagonist is the muscle-type nicotinic acetylcholine receptor peptide antagonist as initially set forth, wherein: Xaa1 is absent; Xaa2 is absent; the Xaa3-Xaa8 linkage is selected from: a Cys-Cys linkage, a Sec-Sec linkage, a cystathionine linkage, a lactam bridge, a thioether linkage, and a dicarba linkage; the Xaa4-Xaa14 linkage is selected from: a Cys-Cys linkage, a Sec-Sec linkage, a cystathionine linkage, a lactam bridge, a thioether linkage, and a dicarba linkage; Xaa5 is selected from: Arg, His, Lys, and a derivative of Arg, His, or Lys; Xaa6 is selected from: Pro and a derivative thereof; Xaa7 is selected from: Ala, Gly, Val, Leu, Ile and a derivative of Ala, Gly, Val, Leu, or Ile; Xaa9 is selected from: Ala, Gly, Val, Leu, Ile and a derivative of Ala, Gly, Val, Leu, or Ile; Xaa10 is selected from: Arg, His, Lys, and a derivative of Arg, His, or Lys; Xaa11 is selected from: Arg, His, Lys, and a derivative of Arg, His, or Lys; Xaa12 is selected from: Phe, Trp, Tyr, and a derivative of Phe, Trp, or Tyr; and Xaa13 is selected from: Cys, Met, Sec, Ser, Thr, and a derivative of Cys, Met, Sec, Ser, or Thr.

In some embodiments, the muscle-type nicotinic acetylcholine receptor peptide antagonist is the muscle-type nicotinic acetylcholine receptor peptide antagonist as initially set forth, wherein: Xaa1 is absent or selected from Ala, Gly, Val, Leu, Ile and a derivative of Ala, Gly, Val, Leu, or Ile; Xaa2 is absent or selected from: Asn, Asp, Gln, Arg, His, Lys, Phe, Trp, Tyr, Ala, Gly, Val, Leu, Ile, and a derivative of Asn, Asp, Gln, Arg, His, Lys, Phe, Trp, Tyr, Ala, Gly, Val, Leu, or Ile; the Xaa3-Xaa8 linkage is selected from: a Sec-Sec linkage, a cystathionine linkage, a lactam bridge, a thioether linkage, and a dicarba linkage; the Xaa4-Xaa14 linkage is selected from: a Sec-Sec linkage, a cystathionine linkage, a lactam bridge, a thioether linkage, and a dicarba linkage; Xaa5 is selected from: Asp, Gln, Glu, Arg, His, Lys, and a derivative of Asp, Gln, Glu, Arg, His, or Lys; Xaa6 is selected from: Pro and a derivative thereof; Xaa7 is selected from: Gly, Val, Leu, Ile and a derivative of Gly, Val, Leu, or Ile; Xaa9 is selected from: Ala, Val, Leu, Ile and a derivative of Ala, Val, Leu, or Ile; Xaa10 is selected from: His, Lys, and a derivative of His or Lys; Xaa11 is selected from: Asn, Asp, Gln, Glu, Arg, Lys, and a derivative of Asn, Asp, Gln, Glu, Arg, or Lys; Xaa12 is selected from: Phe, Trp, Tyr, and a derivative of Phe or Trp; and Xaa13 is selected from: Cys, Met, Sec, Thr, Arg, His, Lys, and a derivative of Cys, Met, Sec, Thr, Arg, His, or Lys.

In some embodiments, the muscle-type nicotinic acetylcholine receptor peptide antagonist is the muscle-type nicotinic acetylcholine receptor peptide antagonist as initially set forth, wherein: Xaa1 is absent or selected from Ala, Gly, Val, Leu, Ile and a derivative of Ala, Gly, Val, Leu, or Ile; Xaa2 is absent or selected from: Asn, Asp, Gln, Arg, His, Lys, Phe, Trp, Tyr, Ala, Gly, Val, Leu, Ile, and a derivative of Asn, Asp, Gln, Arg, His, Lys, Phe, Trp, Tyr, Ala, Gly, Val, Leu, or Ile; the Xaa3-Xaa8 linkage is selected from: a Sec-Sec linkage, a cystathionine linkage, a lactam bridge, a thioether linkage, and a dicarba linkage; the Xaa4-Xaa14 linkage is selected from: a Sec-Sec linkage, a cystathionine linkage, a lactam bridge, a thioether linkage, and a dicarba linkage; Xaa5 is selected from: Asp, Gln, Glu, Arg, Lys, and a derivative of Asp, Gln, Glu, Arg, or Lys; Xaa6 is selected from: Pro and a derivative thereof; Xaa7 is selected from: Gly, Val, Leu, Ile and a derivative of Gly, Val, Leu, or Ile; Xaa9 is selected from: Ala, Val, Leu, Ile and a derivative of Ala, Val, Leu, or Ile; Xaa10 is selected from: Arg, His, and a derivative of Arg or Lys; Xaa11 is selected from: Asn, Asp, Gln, Glu, Arg, Lys, and a derivative of Asn, Asp, Gln, Glu, Arg, or Lys; Xaa12 is selected from: Trp, Tyr, and a derivative of Trp or Tyr; and Xaa13 is selected from: Cys, Met, Sec, Thr, Arg, His, Lys, and a derivative of Cys, Met, Sec, Thr, Arg, His, or Lys.

In some embodiments, the muscle-type nicotinic acetylcholine receptor peptide antagonist is the muscle-type nicotinic acetylcholine receptor peptide antagonist as initially set forth, wherein: Xaa1 is absent or selected from Ala, Val, Leu, Ile and a derivative of Ala, Val, Leu, or Ile; Xaa2 is absent or selected from: Asn, Asp, Gln, Glu, His, Lys, Phe, Trp, Tyr, Ala, Gly, Val, Leu, Ile, and a derivative of Asn, Asp, Gln, Glu, His, Lys, Phe, Trp, Tyr, Ala, Gly, Val, Leu, or Ile; the Xaa3-Xaa8 linkage is selected from: a Sec-Sec linkage, a cystathionine linkage, a lactam bridge, a thioether linkage, and a dicarba linkage; the Xaa4-Xaa14 linkage is selected from: a Sec-Sec linkage, a cystathionine linkage, a lactam bridge, a thioether linkage, and a dicarba linkage; Xaa5 is selected from: Asn, Asp, Gln, Glu, Arg, Lys, and a derivative of Asn, Asp, Gln, Glu, Arg, or Lys; Xaa6 is selected from: Pro and a derivative thereof; Xaa7 is selected from: Gly, Val, Leu, Ile and a derivative of Gly, Val, Leu, or Ile; Xaa9 is selected from: Ala, Val, Leu, Ile and a derivative of Ala, Val, Leu, or Ile; Xaa10 is selected from: Arg, His, and a derivative of Arg or His; Xaa11 is selected from: Asp, Gln, Glu, Arg, His, Lys, and a derivative of Asp, Gln, Glu, Arg, His, or Lys; Xaa12 is selected from: Phe, Trp, and a derivative of Phe or Trp; and Xaa13 is selected from: Cys, Met, Sec, Thr, Arg, His, Lys, and a derivative of Cys, Met, Sec, Thr, Arg, His, or Lys.

In some embodiments, the muscle-type nicotinic acetylcholine receptor peptide antagonist is the muscle-type nicotinic acetylcholine receptor peptide antagonist as initially set forth, wherein: Xaa1 is absent; Xaa2 is absent or selected from: Arg, His, Lys, and a derivative of Arg, His, or Lys; the Xaa3-Xaa8 linkage is selected from: a Cys-Cys linkage, a Sec-Sec linkage, a cystathionine linkage, a lactam bridge, a thioether linkage, and a dicarba linkage; the Xaa4-Xaa14 linkage is selected from: a Cys-Cys linkage, a Sec-Sec linkage, a cystathionine linkage, a lactam bridge, a thioether linkage, and a dicarba linkage; Xaa5 is selected from: Arg, His, Lys, and a derivative of Arg, His, or Lys; Xaa6 is selected from: Pro and a derivative thereof; Xaa7 is selected from: Ala, Gly, Val, Leu, Ile and a derivative of Ala, Gly, Val, Leu, or Ile; Xaa9 is selected from: Ala, Gly, Val, Leu, Ile and a derivative of Ala, Gly, Val, Leu, or Ile; Xaa10 is selected from: Arg, His, Lys, and a derivative of Arg, His, or Lys; Xaa11 is selected from: Arg, His, Lys, Asn, Asp, Gln, Glu, and a derivative of Arg, His, Lys, Asn, Asp, Gln, or Glu; Xaa12 is selected from: Phe, Trp, Tyr, and a derivative of Phe, Trp, or Tyr; and Xaa13 is selected from: Cys, Met, Sec, Ser, Thr, and a derivative of Cys, Met, Sec, Ser, or Thr.

In some embodiments, the muscle-type nicotinic acetylcholine receptor peptide antagonist is the muscle-type nicotinic acetylcholine receptor peptide antagonist as initially set forth, wherein: Xaa1 is absent; Xaa2 is absent or selected from: Arg and a derivative of Arg; the Xaa3-Xaa8 linkage is a Cys-Cys linkage; the Xaa4-Xaa14 linkage is selected from: a Cys-Cys linkage and a cystathionine linkage; Xaa5 is selected from: His and a derivative of His; Xaa6 is selected from: Pro and a derivative thereof; Xaa7 is selected from: Ala and a derivative of Ala; Xaa9 is selected from: Gly and a derivative of Gly; Xaa10 is selected from: Arg, Lys, and a derivative of Arg or Lys; Xaa11 is selected from: His, Asn, and a derivative of His or Asn; Xaa12 is selected from: Tyr and a derivative of Tyr; and Xaa13 is selected from: Ser and a derivative of Ser.

In some embodiments, the Xaa3-Xaa8 linkage and the Xaa4-Xaa14 linkage are independently selected from: a Cys-Cys linkage; a Sec-Sec linkage; a cystathionine linkage; a lactam bridge, a thioether linkage, and a dicarba linkage. In some embodiments, the thioether linkage is a lanthionine linkage. In some embodiments, the linkage between Xaa3 and Xaa8 has a spatial separation between the alpha carbons or the geometric centers of each of Xaa3 and Xaa8 of about 3.5 to about 10 angstroms, wherein the linkage between Xaa4 and Xaa14 has a spatial separation between the alpha carbons or the geometric centers of each of Xaa4 and Xaa14 of about 3.5 to about 10 angstroms, or both.

In some embodiments, the muscle-type nicotinic acetylcholine receptor peptide antagonist is the muscle-type nicotinic acetylcholine receptor peptide antagonist of the present invention, wherein the N-terminus is modified to comprise $C_1$-$C_6$ acyl, $C_1$-$C_8$ alkyl, $C_6$-$C_{12}$ aralkyl, $C_5$-$C_{10}$ aryl, $C_4$-$C_8$ heteroaryl, formyl, or a lipid. In some embodiments, the N-terminus is not modified with an amino acid or a derivative of an amino acid.

In some embodiments, the muscle-type nicotinic acetylcholine receptor peptide antagonist is the muscle-type nicotinic acetylcholine receptor peptide antagonist of the present invention, wherein the C-terminus is modified to comprise $NH_2$, amino-acyl, amino-$C_1$-$C_8$ alkyl, amino-$C_6$-$C_{12}$-aralkyl, amino-$C_5$-$C_{10}$ aryl, amino-$C_4$-$C_8$ heteroaryl, or O—($C_1$-$C_8$ alkyl). In some embodiments, the C-terminus is not modified with an amino acid or a derivative of an amino acid.

In some embodiments, the muscle-type nicotinic acetylcholine receptor peptide antagonist is the muscle-type nicotinic acetylcholine receptor peptide antagonist of the present invention, wherein a lipid is covalently attached to a cysteine, serine, lysine, threonine or tyrosine. In some embodiments, the lipid is covalently attached to a cysteine or a lysine. In some embodiments, the lipid comprises a $C_6$-$C_{20}$ alkyl, $C_6$-$C_{20}$ alkenyl, $C_6$-$C_{20}$ alkynyl, or $C_6$-$C_{20}$ acyl group. In some embodiments, the lipid comprises a geranyl, farnesyl, or geranylgeranyl group. In some embodiments, the lipid comprises a undecyloyl, lauroyl, tridecyloyl, myristoyl, palmitoyl, or stearoyl group. In some embodiments, the lipid is a covalent modification of Cys added by palmitoylation or prenylation.

In some embodiments, the muscle-type nicotinic acetylcholine receptor peptide antagonist is the muscle-type nicotinic acetylcholine receptor peptide antagonist of the present invention comprising at least one derivative that is a non-canonical amino acid selected from the group consisting of: an aromatic side chain amino acid; a non-aromatic side chain amino acid; an aliphatic side chain amino acid; a side chain amide amino acid; a side chain ester amino acid; a heteroaromatic side chain amino acid; a side chain thiol amino acid; a beta amino acid; and a backbone-modified amino acid. In some embodiments, the aromatic side chain amino acid is a derivative of tyrosine, histidine, tryptophan, or phenylalanine. In some embodiments, the non-aromatic side chain amino acid is a derivative of serine, threonine, cysteine, methionine, arginine, asparagine, glutamine, aspartic acid, glutamic acid, lysine, proline, glycine, alanine, valine, isoleucine, or leucine. In some embodiments, the at least one derivative is a non-canonical amino acid selected from the group consisting of: 2-aminoadipic acid; 3-aminoadipic acid; beta-alanine; beta-aminoproprionic acid; 2-aminobutyric acid; 4-aminobutyric acid; piperidinic acid; 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminoproprionic acid; N-ethylglycine; N-ethylasparagine; hydroxylysine; allo-hydroxylysine; 3-hydroxyproline; 4-hydroxyproline; isodesmosine; allo-isoleucine; N-methylglycine; sarcosine; n-methylisoleucine; 6-N-methyllysine; N-methylvaline; norvaline; norleucine; and ornithine.

In some embodiments, the muscle-type nicotinic acetylcholine receptor peptide antagonist is the muscle-type nicotinic acetylcholine receptor peptide antagonist of the present invention, wherein one or more amino acids in the peptide have the D-amino acid configuration and the remaining amino acids in the peptide have the L-amino acid configuration.

In some embodiments, a muscle-type nicotinic acetylcholine receptor peptide antagonist of the invention selectively inhibits a muscle-type nicotinic acetylcholine receptor. In related embodiments, the $IC_{50}$ is about 1 millimolar to about 1 picomolar. In some embodiments, the $IC_{50}$ is determined by an activity assay. In some embodiments, the activity assay is a competitive binding assay or an assay of inhibition of the acetylcholine receptor ion channel conductance.

In some embodiments, the invention includes a cosmetic composition comprising a muscle-type nicotinic acetylcholine receptor peptide antagonist of the invention, for prevention or temporary improvement of the appearance of one or more of skin wrinkles, skin laxity, moderate to severe glabellar lines associated with corrugator and/or procerus muscle activity, moderate to severe lateral canthal lines associated with orbicularis oculi activity, and moderate to severe forehead lines associated with frontalis muscle activity, in a subject. In some embodiments, the cosmetic composition is formulated for topical use. In some embodiments, the cosmetic composition comprises one or more excipient selected from the group consisting of: water, a buffer, an absorption enhancer, a stability enhancer, diaminobutyroyl benzylamide, diacetate, glycerin, a gum, a hydrophilic colloid or derivative, a cellulosic derivative, an emulsifier, a fatty alcohol, an acrylic derivative, a mineral, a surfactant, a fat, an oil, a preservative, a monosaccharide, a disaccharide, a polysaccharide, a glycosaminoglycan, and a chelating agent. In some embodiments, the absorption enhancer is selected from the group consisting of: a liposome delivery system, a transfersome delivery system, an ethosome delivery system, a short chain alcohol, a long chain alcohol, a polyalcohol, urea, an amino acid, an amino acid ester, an amine, an amide, 1-dodecylazacycloheptan-2-one (AZONE®), a derivative of 1-dodecylazacycloheptan-2-one, a pyrrolidone, a pyrrolidone derivative, a terpene, a terpene derivative, a fatty acid, a fatty acid ester, a macrocyclic compound, a tenside, a sulfoxide, lecithin vesicles, water surfactants, a polyol, a small molecule tri, tetra, penta, hexa, septa or octa peptide, isoceteth-20, ethoxydiglycol, dimethyl sulfoxide, dimethyl isosorbide, and phloretin. In some embodiments, the stability enhancer is a small molecule peptide. In some embodiments, the small molecule peptide is selected from the group consisting of: a tripeptide, a tetrapeptide, a pentapeptide, a hexapeptide, a septapeptide, an octapeptide, Acetyl Hexapeptide-3 Cosmetic Topical Peptide, Melanotan II, ACVR2B (ACE-031), Argireline® Acetate, Argireline, Matrixyl Acetate (palmitoyl pentapeptide), peptide GHK spontaneously complexes with copper, Palmitoyl Tetrapeptide-3, Argireline, Acetyl Glutamyl Heptapeptide, Matrixyl™, Snap-8, Syn®-Tacks, Syn®-Coll, Syn®-Hycan, Leuphasyl®, Pepha®-Tight, Tego® Pep 4-17 and Trylagen®. In some embodiments, the cosmetic composition further comprises one or more other active ingredient. In some embodiments, the one or more other active ingredient is selected from the group consisting of: a second, different, muscle-type nicotinic acetylcholine receptor peptide antagonist, an antioxidant, a retinoid, a growth factor, a collagen stimulating peptide, a carrier peptide, a peptide that inhibits tTAT-superoxide dismutase, a peptide that inhibits a proteinase, a peptide that stimulates hyaluronan synthase 2, and a keratin-based peptide. In some embodiments, the cosmetic composition comprises a liposome delivery system. In some embodiments, the cosmetic composition is a cream, balm, gel, solution, serum, cosmetic, liquid, lotion, ointment, emulsion, milk, spray, mask, or the like. In some embodiments, the cosmetic composition comprises about 0.01% to about 5% w/w of the muscle-type nicotinic acetylcholine receptor peptide antagonist.

In some embodiments, the invention includes a cosmetic composition comprising a muscle-type nicotinic acetylcholine receptor peptide antagonist of the invention, for: prevention or temporary improvement of the appearance of one or more of skin wrinkles, skin laxity, moderate to severe glabellar lines associated with corrugator and/or procerus muscle activity, moderate to severe lateral canthal lines associated with orbicularis oculi activity, and moderate to severe forehead lines associated with frontalis muscle activity; treatment of overactive bladder (OAB); treatment of urinary incontinence; prophylaxis of headaches; treatment of spasticity; treatment of cervical dystonia; treatment of hypersalivation; treatment of blepharospasm associated with dystonia; or treatment of strabismus, in a subject. In some embodiments, the pharmaceutical composition is formulated for intradermal, subcutaneous, intramuscular, or intradetrusor administration. In some embodiments, the pharmaceutical composition comprises one or more excipient.

In some embodiments, the invention includes a method for preventing or temporarily improving the appearance in a subject for prevention or temporary improvement of the appearance of one or more of skin wrinkles, skin laxity, moderate to severe glabellar lines associated with corrugator and/or procerus muscle activity, moderate to severe lateral canthal lines associated with orbicularis oculi activity, and moderate to severe forehead lines associated with frontalis muscle activity, comprising applying an effective amount of the cosmetic composition comprising the muscle-type nicotinic acetylcholine receptor peptide antagonist of the invention to the subject. In some embodiments of this method, the muscle-type nicotinic acetylcholine receptor peptide antagonist is applied in one or more doses of the cosmetic composition. In some embodiments, a single dose of the cosmetic composition is applied about once per hour to about once per 2 weeks. In some embodiments, a single dose of the cosmetic composition is applied about once per day. In some embodiments, the cosmetic composition can be applied indefinitely with no adverse effect. In some embodiments, the dose of the cosmetic composition is a subimmunological dose.

The invention further includes a method for: preventing or temporarily improving one or more of the appearance of skin wrinkles, skin laxity, moderate to severe glabellar lines associated with corrugator and/or procerus muscle activity, moderate to severe lateral canthal lines associated with orbicularis oculi activity, and moderate to severe forehead lines associated with frontalis muscle activity; treatment of overactive bladder (OAB); treatment of urinary incontinence; prophylaxis of headaches; treatment of spasticity; treatment of cervical dystonia; treatment of hypersalivation; treatment of blepharospasm associated with dystonia; or treatment of strabismus; in a subject, comprising administering an effective amount of the pharmaceutical composition comprising the muscle-type nicotinic acetylcholine receptor peptide antagonist of the invention to the subject. In some embodiments, the muscle-type nicotinic acetylcholine receptor peptide antagonist is administered in one or more treatments with the pharmaceutical composition. In some embodiments, administration of each treatment comprises injection of the pharmaceutical composition by injection into one or more treatment sites. In some embodiments, each treatment comprises a subimmunological dose of the pharmaceutical composition.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

As used herein, the term "comprise" or variations thereof such as "comprises" or "comprising" are to be read to indicate the inclusion of any recited feature but not the exclusion of any other features. Thus, as used herein, the term "comprising" is inclusive and does not exclude additional, unrecited features. In some embodiments of any of the compositions and methods provided herein, "comprising" may be replaced with "consisting essentially of" or "consisting of." The phrase "consisting essentially of" is used herein to require the specified feature(s) as well as those which do not materially affect the character or function of the claimed invention. As used herein, the term "consisting" is used to indicate the presence of the recited feature alone.

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—$NH_2$ radical.
"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR³, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —OR$^a$, —SR$^a$, —OC(O)R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)

N($R^a$)$_2$, —N($R^a$)C(O)O$R^a$, —OC(O)—N($R^a$)$_2$, —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—O$R^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" or "cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—O$R^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$O$R^a$ (where t is 1 or 2) and —$R^b$—S(O)$_t$N($R^a$)$_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical are optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" or "heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—$OC(O)R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

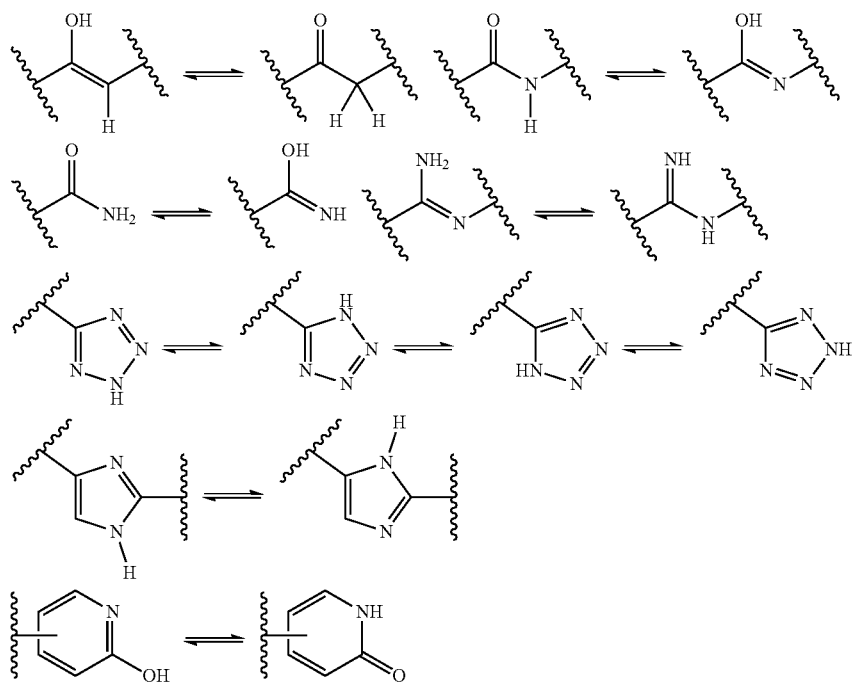

The compounds disclosed herein, in some embodiments, are used in different enriched isotopic forms, e.g., enriched in the content of $^2H$, $^3H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2H$), tritium ($^3H$), iodine-125 ($^{125}I$) or carbon-14 ($^{14}C$). Isotopic substitution with $^2H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{125}I$ are all contemplated. All isotopic variations of the compounds of the present invention, whether radioactive or not, are encompassed within the scope of the present invention.

In certain embodiments, the compounds disclosed herein have some or all of the $^1H$ atoms replaced with $^2H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., *supra.*

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

"Prodrug" is meant to indicate a compound that is, in some embodiments, converted under physiological conditions or by solvolysis to a biologically active compound described herein. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Muscle-Type Nicotinic Acetylcholine Receptor

The present invention relates to peptide antagonists of muscle-type nicotinic acetylcholine receptors, also referred to as muscle nAChR.

The muscle nAChR is a ligand-activated ion channel receptor having a structure generally described as a heteropentamer of four related, but genetically and immunologically distinct, subunits. The subunits are organized around a central pore in the membrane with a stoichiometry of two α subunits and one each of β, δ, and γ. Muscle nAChR is activated by the endogenous neurotransmitter acetylcholine (ACh, the natural receptor agonist) released by the nerve at the neuromuscular junction. ACh binds to the receptor resulting in transmission of a signal for channel activation, or gating.

The peptide antagonists of the invention bind in the active site of the muscle nAChR, inhibiting binding of ACh to the receptor. This results in a non-depolarizing blockage of the neuromuscular postsynaptic membrane, such that the signal from the nerve (the ACh release) is no longer effective in stimulating muscle contraction. See, e.g., Albuquerque, et al., 2009, "Mammalian Nicotinic Acetylcholine Receptors: From Structure to Function," Physiol. Rev. 89(1):73-120, and Kalamida, et al., 2007, "Muscle and neuronal nicotinic acetylcholine receptors," The FEBS Journal 274:3799-3845, each incorporated herein by reference in its entirety.

Intentional muscle deinnervation has been achieved using the anticholinergic botulinum toxin products: onabotulinumtoxin A (BTX-A, marketed as BOTOX®), abobotulinumtoxin A (Dysport®), and incobotulinumtoxin A (Xeomin®). BTX-A prevents the secretion of ACh, present in nerve cell vesicles, from the nerve cell at the synapse. This results in an absence of ACh at the synapse and failure to innervate the muscle cell. The mechanism of action of these toxins are thus pre-synaptic. Botulinum toxin is indicated for use in, e.g, preventing or improving of the appearance of skin wrinkles, e.g., in the face, skin laxity, moderate to severe glabellar lines associated with corrugator and/or procerus muscle activity, moderate to severe lateral canthal lines associated with orbicularis oculi activity (crow's feet lines), moderate to severe forehead lines associated with frontalis muscle activity; treatment of overactive bladder (OAB); treatment of urinary incontinence; prophylaxis of headaches in adult patients with chronic migraine; treatment of spasticity; treatment of cervical dystonia; treatment of hypersalivation (also called ptyalism or sialorrhea); treatment of blepharospasm associated with dystonia; treatment of and treatment of strabismus. (See, e.g., Botox Cosmetic BLA 103000, product labeling for Botox Cosmetic revised May 2018, product labeling for Botox revised April 2017, Dysport BLA 125274, product labeling for Dysport revised June 2017, Xeomin BLA 125360, product labeling for Xeomin revised July 2018, each incorporated herein by reference.)

In contrast, peptide antagonists of the invention occupy the ACh active site in muscle cell AChRs (post-synapse). When bound, a peptide antagonist of the invention blocks the binding of ACh that has been secreted from the nerve cell.

Peptide Antagonists of the Muscle-Type Nicotinic Acetylcholine Receptor

The present invention provides peptide antagonists of mammalian muscle nAChR, including human muscle nAChR. In some embodiments, a peptide antagonist of the invention has a desirable property, or an improved property relative to a muscle nAChR antagonist known in the art. Such a property can include, e.g., a pharmacokinetic property (including but not limited to absorption, bioavailability, distribution, metabolism, and excretion), a pharmacodynamic property (including but not limited to: receptor binding characteristics, e.g., binding half-life; postreceptor effects; and chemical interactions), enhanced activity (e.g., represented by $IC_{50}$), stability (e.g., represented by half-life), solubility (e.g., in a formulation), or permeability (e.g., permeability of the skin by a formulation containing the peptide antagonist). In some embodiments, a formulation containing a peptide antagonist of the invention has a desirable property, or an improved property relative to a formulation containing a muscle nAChR antagonist known in the art. In some embodiments, a desirable or improved property of a formulation of the invention is a property relating to the use of the formulation for an indication as described elsewhere herein, e.g., use for reducing or improving the appearance of skin wrinkles.

Peptide Antagonists

In some embodiments, a muscle-type nicotinic acetylcholine receptor peptide antagonist of the invention has 12-14 residues and comprises the amino acid sequence:
Xaa1-Xaa2-Xaa3-Xaa4-Xaa5-Xaa6-Xaa7-Xaa8-Xaa9-Xaa10-Xaa11-Xaa12-Xaa13-Xaa14
wherein:
Xaa1 is absent or selected from Ala, Gly, Val, Leu, Ile and a derivative of Ala, Gly, Val, Leu, or Ile;
Xaa2 is absent or selected from: Asn, Asp, Gln, Glu, Arg, His, Lys, Phe, Trp, Tyr, Ala, Gly, Val, Leu, Ile, and a derivative of Asn, Asp, Gln, Glu, Arg, His, Lys, Phe, Trp, Tyr, Ala, Gly, Val, Leu, or Ile;
Xaa3 and Xaa8 form a linkage Xaa3-Xaa8;
Xaa4 and Xaa14 form a linkage Xaa4-Xaa14;

Xaa5 is selected from: Asn, Asp, Gln, Glu, Arg, His, Lys, and a derivative of Asn, Asp, Gln, Glu, Arg, His, or Lys;

Xaa6 is selected from: Pro and a derivative thereof;

Xaa7 is selected from: Ala, Gly, Val, Leu, Ile and a derivative of Ala, Gly, Val, Leu, or Ile;

Xaa9 is selected from: Ala, Gly, Val, Leu, Ile and a derivative of Ala, Gly, Val, Leu, or Ile;

Xaa10 is selected from: Arg, His, Lys, and a derivative of Arg, His, or Lys;

Xaa11 is selected from: Asn, Asp, Gln, Glu, Arg, His, Lys, and a derivative of Asn, Asp, Gln, Glu, Arg, His, or Lys;

Xaa12 is selected from: Phe, Trp, Tyr, and a derivative of Phe, Trp, or Tyr;

Xaa13 is selected from: Cys, Met, Sec, Ser, Thr, Arg, His, Lys, and a derivative of Cys, Met, Sec, Ser, Thr, Arg, His, or Lys;

the N-terminus is optionally modified; and the C-terminus is optionally modified.

In some embodiments, the peptide antagonist of the invention does not consist of the following amino acid sequence:

Glu-Cys-Cys-Asn-Pro-Ala-Cys-Gly-Arg-His-Tyr-Ser-Cys (SEQ ID NO: 1)

wherein the first and third cysteine residues (Xaa3-Xaa8) are linked and the second and fourth cysteine residues (Xaa4-Xaa14) are linked (α-conotoxin GI, or CGI).

In some embodiments, the peptide antagonist of the invention does not consist of the following amino acid sequence:

Glu-Cys-Cys-Asn-Pro-Ala-Cys-Gly-Lys-His-Phe-Ser-Cys (SEQ ID NO: 2)

wherein the first and third cysteine residues (Xaa3-Xaa8) are linked and the second and fourth cysteine residues (Xaa4-Xaa14) are linked.

In some embodiments, the peptide antagonist of the invention does not consist of the following amino acid sequence:

Glu-Cys-Cys-His-Pro-Ala-Cys-Gly-Lys-His-Phe-Ser-Cys (SEQ ID NO: 56)

wherein the first and third cysteine residues (Xaa3-Xaa8) are linked and the second and fourth cysteine residues (Xaa4-Xaa14) are linked (an α-conotoxin GII sequence).

In some embodiments, the peptide antagonist of the invention does not consist of the following amino acid sequence:

Gly-Arg-Cys-Cys-His-Pro-Ala-Cys-Gly-Lys-Asn-Tyr-Ser-Cys (SEQ ID NO: 3)

wherein the first and third cysteine residues (Xaa3-Xaa8) are linked and the second and fourth cysteine residues (Xaa4-Xaa14) are linked (α-conotoxin MI, or CMI).

In some embodiments, the number of amino acid residues in a peptide antagonist of the invention is not more than 12, not more than 13 or not more than 14. In embodiments, a peptide antagonist of the invention consists of 12, 13 or 14 amino acid residues.

Non-limiting examples of peptide antagonists of the invention are shown in Table 1.

TABLE 1

Peptide Antagonist Examples

| SEQ ID NO | SEQUENCE |
|---|---|
| 4[3,4] | Ac-Cys-Cys-Lys-Pro-Ala-Cys-Gly-Lys-Asn-Tyr-Ser-Cys-NH$_2$ |
| 5[2,3] | Ac-Cys-(Cyt)-Arg-Pro-Ala-Cys-Gly-His-Asn-Tyr-Ser-(Cyt)-NH$_2$ |
| 6[2,3] | Ac-Cys-(Cyt)-His-Pro-Ala-Cys-Gly-His-Asn-Tyr-Ser-(Cyt)-NH$_2$ |
| 7[1,2] | Ac-(Cyt)-(Cyt)-Lys-Pro-Ala-(Cyt)-Gly-Lys-Gln-Tyr-Ser-(Cyt)-NH$_2$ |
| 8[3,4] | Ac-Cys-Cys-Arg-Pro-Ala-Cys-Gly-Lys-Gln-Tyr-Ser-Cys-NH$_2$ |
| 9[1,3] | Ac-(Cyt)-Cys-His-Pro-Ala-(Cyt)-Gly-Lys-Gln-Tyr-Ser-Cys-NH$_2$ |
| 10[1,2] | Ac-(Cyt)-(Cyt)-His-Pro-Ala-(Cyt)-Gly-Arg-Gln-Tyr-Ser-(Cyt)-NH$_2$ |
| 11[2,3] | H-Cys-(Cyt)-His-Pro-Ala-Cys-Gly-Arg-Asn-Tyr-Ser-(Cyt)-NH$_2$ |
| 12[3,4] | Ac-Cys-Cys-Arg-Pro-Ala-Cys-Gly-Arg-Asn-Tyr-Ser-Cys-NH$_2$ |
| 13[1,2] | Ac-(Cyt)-(Cyt)-Lys-Pro-Ala-(Cyt)-Gly-Arg-Asn-Tyr-Ser-(Cyt)-NH$_2$ |
| 14[2,5] | Ac-Sec-(Cyt)-Lys-Pro-Ala-Sec-Gly-Lys-Asn-Tyr-Ser-(Cyt)-NH$_2$ |
| 15[1,2] | Ac-(Cyt)-(Cyt)-His-Pro-Ala-(Cyt)-Gly-Lys-Asn-Tyr-Ser-(Cyt)-NH$_2$ |
| 16[1,2] | H-(Cyt)-(Cyt)-His-Pro-Ala-(Cyt)-Gly-Lys-Asn-Tyr-Ser-(Cyt)-NH$_2$ |
| 17[5,6] | Ac-Sec-Sec-Asn-Pro-Ala-Sec-Gly-Arg-His-Tyr-Ser-Sec-NH$_2$ |
| 18[1,3] | NH$_2$-(Cyt)-Cys-Asn-Pro-Ala-(Cyt)-Gly-Arg-His-Tyr-Ser-Cys-NH$_2$ |
| 19[3,4] | Ac-Cys-Cys-Gln-Pro-Ala-Cys-Gly-Lys-His-Tyr-Ser-Cys-NH$_2$ |
| 20[2,3] | Ac-Cys-(Cyt)-Asn-Pro-Ala-(Cyt)-Gly-Lys-His-Tyr-Ser-(Cyt)-NH$_2$ |
| 21[1,2] | Ac-(Cyt)-(Cyt)-Asn-Pro-Ala-(Cyt)-Gly-Arg-His-Tyr-Ser-(Cyt)-NH$_2$ |
| 22[1,4] | Ac-(Cyt)-Cys-Asn-Pro-Ala-(Cyt)-Gly-Arg-His-Tyr-Ser-Cys-NH$_2$ |

TABLE 1-continued

Peptide Antagonist Examples

| SEQ ID NO | SEQUENCE |
|---|---|
| 23[2,3] | Ac-Cys-(Cyt)-Asn-Pro-Ala-Cys-Gly-Lys-His-Tyr-Ser-(Cyt)-NH$_2$ |
| 24[1,2] | Ac-(Cyt)-(Cyt)-Asn-Pro-Ala-(Cyt)-Gly-Lys-His-Tyr-Ser-(Cyt)-NH$_2$ |
| 25[1,2] | NH$_2$-(Cyt)-(Cyt)-Asn-Pro-Ala-(Cyt)-Gly-Arg-His-Tyr-Ser-(Cyt)-NH$_2$ |
| 26[1,2] | H-(Cyt)-(Cyt)-Asn-Pro-Ala-(Cyt)-Gly-Arg-His-Tyr-Ser-(Cyt)-NH$_2$ |
| 27[1,2] | Ac-Arg-(Cyt)-(Cyt)-His-Pro-Ala-(Cyt)-Gly-Lys-Asn-Tyr-Ser-(Cyt)-NH$_2$ |
| 28[1,2] | H-Arg-(Cyt)-(Cyt)-His-Pro-Ala-(Cyt)-Gly-Lys-Asn-Tyr-Ser-(Cyt)-NH$_2$ |
| 29[3,4] | Ac-Arg-Cys-Cys-His-Pro-Ala-Cys-Gly-Lys-Asn-Tyr-Ser-Cys-NH$_2$ |
| 30[2,3] | Ac-Arg-Cys-(Cyt)-Lys-Pro-Ala-Cys-Gly-Lys-Asn-Tyr-Ser-(Cyt)-NH$_2$ |
| 31[2,3] | Ac-Arg-Cys-(Cyt)-His-Pro-Ala-Cys-Gly-Lys-Asn-Tyr-Ser-(Cyt)-NH$_2$ |
| 32[1,3] | Ac-Arg-(Cyt)-Cys-His-Pro-Ala-(Cyt)-Gly-Arg-Asn-Tyr-Ser-Cys-NH$_2$ |
| 33[1,2] | Ac-Arg-(Cyt)-(Cyt)-Arg-Pro-Ala-(Cyt)-Gly-Lys-Asn-Tyr-Ser-(Cyt)-NH$_2$ |
| 34[1,2] | Ac-Arg-(Cyt)-(Cyt)-His-Pro-Ala-(Cyt)-Gly-His-Asn-Tyr-Ser-(Cyt)-NH$_2$ |
| 35[1,2] | H-Arg-(Cyt)-(Cyt)-Arg-Pro-Ala-(Cyt)-Gly-Lys-Asn-Tyr-Ser-(Cyt)-NH$_2$ |
| 36[5,6] | Ac-Arg-Sec-Sec-His-Pro-Ala-Sec-Gly-Lys-Asn-Tyr-Ser-Sec-NH$_2$ |
| 37[1,2] | Ac-Lys-(Cyt)-(Cyt)-His-Pro-Ala-(Cyt)-Gly-Lys-Asn-Tyr-Ser-(Cyt)-NH$_2$ |
| 38[1,2] | Ac-Lys-(Cyt)-(Cyt)-His-Pro-Ala-(Cyt)-Gly-Arg-Asn-Tyr-Ser-(Cyt)-NH$_2$ |
| 39[1,2] | H-(Cyt)-(Cyt)-His-Pro-Ala-(Cyt)-Gly-Arg-His-Tyr-Ser-(Cyt)-NH$_2$ |
| 40[3,4] | Ac-Cys-Cys-Lys-Pro-Ala-Cys-Gly-Arg-His-Tyr-Ser-Cys-NH$_2$ |
| 41[2,3] | Ac-Cys-(Cyt)-His-Pro-Ala-Cys-Gly-Arg-His-Tyr-Ser-(Cyt)-NH$_2$ |
| 42[2,3] | H-Cys-(Cyt)-His-Pro-Ala-Cys-Gly-Arg-His-Tyr-Ser-(Cyt)-NH$_2$ |
| 43[1,2] | Ac-(Cyt)-(Cyt)-His-Pro-Ala-(Cyt)-Gly-Lys-His-Tyr-Ser-(Cyt)-NH$_2$ |
| 44[1,2] | Ac-(Cyt)-(Cyt)-His-Pro-Ala-(Cyt)-Gly-Arg-His-Tyr-Ser-(Cyt)-NH$_2$ |
| 45[1,2] | H-(Cyt)-(Cyt)-His-Pro-Ala-(Cyt)-Gly-Lys-His-Tyr-Ser-(Cyt)-NH$_2$ |
| 46[1,3] | Ac-(Cyt)-Cys-His-Pro-Ala-(Cyt)-Gly-Arg-Lys-Tyr-Ser-Cys-NH$_2$ |
| 47[1,3] | H-(Cyt)-Cys-His-Pro-Ala-(Cyt)-Gly-Arg-Lys-Tyr-Ser-Cys-NH$_2$ |
| 48[1,3] | Ac-(Cyt)-Cys-His-Pro-Ala-(Cyt)-Gly-Arg-Lys-Tyr-Ser-Cys-NH$_2$ |
| 49[1,2] | NH$_2$-(Cyt)-(Cyt)-His-Pro-Ala-(Cyt)-Gly-Arg-His-Tyr-Ser-(Cyt)-NH$_2$ |
| 50[1,2] | Ac-(Cyt)-(Cyt)-Lys-Pro-Ala-(Cyt)-Gly-Arg-His-Tyr-Ser-(Cyt)-NH$_2$ |
| 51[2,5] | Ac-Sec-(Cyt)-His-Pro-Ala-Sec-Gly-Lys-His-Tyr-Ser-(Cyt)-NH$_2$ |
| 52[1,6] | Ac-(Cyt)-Sec-His-Pro-Ala-(Cyt)-Gly-Arg-His-Tyr-Ser-Sec-NH$_2$ |
| 60[3,4] | Ac-Cys-Cys-Asn-Pro-Ala-Cys-Gly-Lys-Asn-Tyr-Ser-Cys-NH$_2$ |
| 61[3,4] | Ac-Cys-Cys-His-Pro-Ala-Cys-Gly-Arg-His-Tyr-Ser-Cys-NH$_2$ |
| 62[3,4] | Ac-Cys-Cys-Asn-Pro-Ala-Cys-Gly-Lys-Asn-Tyr-Lys-Cys-NH$_2$ |
| 63[1,2] | Ac-(Cyt)-(Cyt)-Asn-Pro-Ala-(Cyt)-Gly-Lys-Asn-Tyr-Ser-(Cyt)-NH$_2$ |
| 64[1,2] | Ac-(Cyt)-(Cyt)-His-Pro-Ala-(Cyt)-Gly-Arg-His-Tyr-Ser-(Cyt)-NH$_2$ |
| 65[1,2] | Ac-(Cyt)-(Cyt)-Asn-Pro-Ala-(Cyt)-Gly-Lys-Asn-Tyr-Lys-(Cyt)-NH$_2$ |
| 66[2,3] | Ac-Cys-(Cyt)-Asn-Pro-Ala-Cys-Gly-Lys-Asn-Tyr-Ser-(Cyt)-NH$_2$ |

TABLE 1-continued

Peptide Antagonist Examples

| SEQ ID NO | SEQUENCE |
|---|---|
| 67[2,3] | Ac-Cys-(Cyt)-His-Pro-Ala-Cys-Gly-Arg-His-Tyr-Ser-(Cyt)-NH$_2$ |
| 68[2,3] | Ac-Cys-(Cyt)-Asn-Pro-Ala-Cys-Gly-Lys-Asn-Tyr-Lys-(Cyt)-NH$_2$ |
| 69[1,4] | Ac-(Cyt)-Cys-Asn-Pro-Ala-(Cyt)-Gly-Lys-Asn-Tyr-Ser-Cys-NH$_2$ |
| 70[1,4] | Ac-(Cyt)-Cys-His-Pro-Ala-(Cyt)-Gly-Arg-His-Tyr-Ser-Cys-NH$_2$ |
| 71[1,4] | Ac-(Cyt)-Cys-Asn-Pro-Ala-(Cyt)-Gly-Lys-Asn-Tyr-Lys-Cys-NH$_2$ |
| 72[1,4] | Ac-Arg-(Cyt)-Cys-His-Pro-Ala-(Cyt)-Gly-Lys-Asn-Tyr-Ser-Cys-NH$_2$ |
| 73[2,3] | Ac-Arg-Cys-(Cyt)-His-Pro-Ala-Cys-Gly-Lys-Asn-Tyr-Ser-(Cyt)-NH$_2$ |
| 74[3,4] | Ac-Arg-Cys-Cys-His-Pro-Ala-Cys-Gly-Lys-Asn-Tyr-Ser-Cys-NH$_2$ |
| 75[1,2] | Ac-Arg-(Cyt)-(Cyt)-His-Pro-Ala-(Cyt)-Gly-Lys-Asn-Tyr-Ser-(Cyt)-NH$_2$ |
| 76[2,3] | Ac-Cys-(Cyt)-His-Pro-Ala-Cys-Gly-Lys-Asn-Tyr-Ser-(Cyt)-NH$_2$ |
| 77[1,2] | Ac-(Cyt)-(Cyt)-His-Pro-Ala-(Cyt)-Gly-Lys-Asn-Tyr-Ser-(Cyt)-NH$_2$ |
| 78[3,4] | Ac-Cys-Cys-His-Pro-Ala-Cys-Gly-Lys-Asn-Tyr-Ser-Cys-NH$_2$ |
| 79[1,4] | Ac-(Cyt)-Cys-His-Pro-Ala-(Cyt)-Gly-Lys-Asn-Tyr-Ser-Cys-NH$_2$ |

[1] Comprises a cystathionine (Cyt-Cyt) linkage at (Xaa3-Xaa8);
[2] comprises a cystathionine (Cyt-Cyt) linkage at (Xaa4-Xaa14);
[3] comprises a disulfide (Cys-Cys) linkage at (Xaa3-Xaa8);
[4] comprises a disulfide (Cys-Cys) linkage at (Xaa4-Xaa14);
[5] comprises a Sec-Sec linkage at (Xaa3-Xaa8);
[6] comprises a Sec-Sec linkage linkage at (Xaa4-Xaa14);
all referring to Xaa1-Xaa14 numbering provided herein.

Unless otherwise indicated in the table, a peptide listed in Table 1 can comprise all L-amino acids or all D-amino acids.

Amino Acid Substitutions

In any embodiment herein, a substitution of an amino acid is made at one or more positions as desired.

Amino acids can be classified based on chemical and structural properties of their sidechains, for example, naturally-occurring amino acids can be classified as hydrophobic (norleucine, Met, Ala, Val, Leu, and Ile), neutral hydrophilic (Cys, Ser, Thr, Asn, and Gln), acidic (Asp and Glu), basic (His, Lys, and Arg), chain orienting (Gly and Pro), and aromatic (Trp, Tyr, and Phe).

In some embodiments, a conservative amino acid substitution is made by substituting an amino acid of one of the above classes with a different member of that class. In some embodiments, conservative substitutions encompass non-naturally occurring amino acid residues, including peptidomimetics and other reversed or inverted forms of amino acid moieties.

In some embodiments, a non-conservative substitution is made by substituting an amino acid of one of the above classes with a member of a different class.

In some embodiments, substitution takes into account the hydropathic index of an amino acid (see, e.g., Kyte et al., 1982, J. Mol. Biol. 157:105-131, incorporated herein by reference). The hydropathic profile of a peptide can be calculated by giving each amino acid a numerical value, or hydropathy index, and repetitively averaging these values along the peptide chain. In such embodiments, each amino acid is assigned a hydropathic index based on hydrophobicity and charge characteristics. In some embodiments, the hydropathic indices used are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In some embodiments, an amino acid is substituted with a different amino acid having a hydropathic index within 0.1 to 0.5 of the original amino acid. In some embodiments, the hydropathic index is within 0.1, 0.2, 0.3, 0.4, or 0.5 of the original amino acid.

In some embodiments, amino acid substitutions are be made based on hydrophilicity. In some embodiments, the hydrophilicity values used are: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4).

In some embodiments, an amino acid is substituted with a different amino acid having a hydrophilicity value within 0.1 to 0.5 of the original amino acid. In some embodiments, the hydrophilicity value is within 0.1, 0.2, 0.3, 0.4, or 0.5 of the original amino acid.

In some embodiments, an amino acid is substituted as shown in the table below. In some embodiments, an amino acid is replaced with a conservative substitution as set forth in Table 2(I), or a derivative (also referred to as an analog herein) of a conservative substitution. In some embodiments, an amino acid is replaced with an alternative substitution as set forth in Table 2(II), showing each full list of alternatives for each amino acid, or a derivative of an alternative substitution.

TABLE 2

Amino Acid Substitutions

| Amino Acid | I. Conservative Substitutions | II. Alternative Substitutions |
|---|---|---|
| Ala | Gly, Ile, Leu, Val | any aliphatic amino acid or derivative thereof (Ala, Gly, Ile, Leu, Val) any hydrophobic amino acid or derivative thereof (Ala, Gly, Ile, Leu, Met, Phe, Pro, Val) |
| Arg | His, Lys | any basic amino acid or derivative thereof (Arg, His, Lys) any charged amino acid or derivative thereof (Asp, Arg, Glu, Lys) any basic amino acid with an electrically charged sidechain or derivative thereof (Arg, His, Lys) |
| Asn | Asp, Gln, Glu | any acidic amino acid or derivative thereof, or any amide of any acidic amino acid or derivative thereof (Asn, Asp, Gln, Glu) any polar amino acid or derivative thereof (Asn, Cys, Gln, His, Ser, Thr, Trp, Tyr) |
| Asp | Asn, Gln, Glu | any acidic amino acid or derivative thereof, or any amide of any acidic amino acid or derivative thereof (Asn, Asp, Gln, Glu) any charged amino acid or derivative thereof (Asp, Arg, Glu, Lys) any polar neutral amino acid or derivative thereof (Asp, Cys, Gln, Ser, Thr) any acidic amino acid with an electrically charged sidechain or derivative thereof (Asp, Glu) |
| Cys | Met, Sec, Ser, Thr | any hydroxyl or sulfur/selenium-containing amino acid or derivative thereof (Cys, Sec, Ser, Met, Thr) any polar amino acid or derivative thereof (Asn, Cys, Gln, His, Ser, Thr, Trp, Tyr) any polar neutral amino acid or derivative thereof (Asp, Cys, Gln, Ser, Thr) |
| Gln | Asn, Asp, Glu | any acidic amino acid or derivative thereof, or any amide of any acidic amino acid or derivative thereof (Asn, Asp, Gln, Glu) any polar amino acid or derivative thereof (Asn, Cys, Gln, His, Ser, Thr, Trp, Tyr) any polar neutral amino acid or derivative thereof (Asp, Cys, Gln, Ser, Thr) any acidic amino acid with an electrically charged sidechain or derivative thereof (Asp, Glu) |
| Glu | Asn, Asp, Gln | any acidic amino acid or derivative thereof, or any amide of any acidic amino acid or derivative thereof (Asn, Asp, Gln, Glu) any charged amino acid or derivative thereof (Asp, Arg, Glu, Lys) |

TABLE 2-continued

Amino Acid Substitutions

| Amino Acid | I. Conservative Substitutions | II. Alternative Substitutions |
|---|---|---|
| Gly | Ala, Ile, Leu, Val | any aliphatic amino acid or derivative thereof (Ala, Gly, Ile, Leu, Val) any hydrophobic amino acid or derivative thereof (Ala, Gly, Ile, Leu, Met, Phe, Pro, Val) |
| His | Arg, Lys | any basic amino acid or derivative thereof (Arg, His, Lys) any polar amino acid or derivative thereof (Asn, Cys, Gln, His, Ser, Thr, Trp, Tyr) any basic amino acid with an electrically charged sidechain or derivative thereof (Arg, His, Lys) |
| Ile | Ala, Gly, Leu, Val | any aliphatic amino acid or derivative thereof (Ala, Gly, Ile, Leu, Val) any hydrophobic amino acid or derivative thereof (Ala, Gly, Ile, Leu, Met, Phe, Pro, Val) |
| Leu | Ala, Gly, Ile, Val | any aliphatic amino acid or derivative thereof (Ala, Gly, Ile, Leu, Val) any hydrophobic amino acid or derivative thereof (Ala, Gly, Ile, Leu, Met, Phe, Pro, Val) |
| Lys | Arg, His | any basic amino acid or derivative thereof (Arg, His, Lys) any charged amino acid or derivative thereof (Asp, Arg, Glu, Lys) any basic amino acid with an electrically charged sidechain or derivative thereof (Arg, His, Lys) |
| Met | Cys, Sec, Ser, Thr | any hydroxyl or sulfur/selenium-containing amino acid or derivative thereof (Cys, Sec, Ser, Met, Thr) any hydrophobic amino acid or derivative thereof (Ala, Gly, Ile, Leu, Met, Phe, Pro, Val) |
| Phe | Trp, Tyr | any aromatic amino acid or derivative thereof (Phe, Trp, Tyr) any hydrophobic amino acid or derivative thereof (Ala, Gly, Ile, Leu, Met, Phe, Pro, Val) |
| Pro | | any cyclic amino acid or derivative thereof (Pro) any hydrophobic amino acid or derivative thereof (Ala, Gly, Ile, Leu, Met, Phe, Pro, Val) |
| Ser | Cys, Met, Sec, Thr | any hydroxyl or sulfur/selenium-containing amino acid or derivative thereof (Cys, Sec, Ser, Met, Thr) any polar amino acid or derivative thereof (Asn, Cys, Gln, His, Ser, Thr, Trp, Tyr) any polar neutral amino acid or derivative thereof (Asp, Cys, Gln, Ser, Thr) |
| Thr | Cys, Met, Sec, Ser | any hydroxyl or sulfur/selenium-containing amino acid or derivative thereof (Cys, Sec, Ser, Met, Thr) any polar amino acid or derivative thereof (Asn, Cys, Gln, His, Ser, Thr, Trp, Tyr) any polar neutral amino acid or derivative thereof (Asp, Cys, Gln, Ser, Thr) |

TABLE 2-continued

Amino Acid Substitutions

| Amino Acid | I. Conservative Substitutions | II. Alternative Substitutions |
|---|---|---|
| Trp | Phe, Tyr, | any aromatic amino acid or derivative thereof (Phe, Trp, Tyr) any polar amino acid or derivative thereof (Asn, Cys, Gln, His, Ser, Thr, Trp, Tyr) |
| Tyr | Phe, Trp | any aromatic amino acid or derivative thereof (Phe, Trp, Tyr) any polar amino acid or derivative thereof (Asn, Cys, Gln, His, Ser, Thr, Trp, Tyr) |
| Val | Ala, Gly, Ile, Leu | any aliphatic amino acid or derivative thereof (Ala, Gly, Ile, Leu, Val) any hydrophobic amino acid or derivative thereof (Ala, Gly, Ile, Leu, Met, Phe, Pro, Val) |

Constraining Structures

In some embodiments, the peptide antagonist of the present invention comprises a constraining structure including, but not limited to, a linkage, bridge or any means of ligation between residues at two positions. In some embodiments, the peptide is constrained by its ends or at positions within the peptide, or both. In some embodiments, the constraining structure influences a peptide antagonist property, e.g., a pharmacokinetic property (including but not limited to absorption, bioavailability, distribution, metabolism, and excretion), a pharmacodynamic property (including but not limited to: receptor binding characteristics, e.g., binding half-life; postreceptor effects; and chemical interactions), enhanced activity (e.g., represented by $IC_{50}$), stability (e.g., represented by half-life), solubility (e.g., in a formulation), or permeability (e.g., permeability of the skin by a formulation containing the peptide antagonist). In certain embodiments, the constraining structure enhances stability of the peptide antagonist. In certain embodiments, the constraining structure enhances permeability through the skin of the peptide antagonist. In certain embodiments, the constraining structure enhances solubility in a formulation, e.g., a topical formulation, of the peptide antagonist.

In embodiments, a peptide antagonist that is constrained as described herein is referred to as a macrocyclic peptide or structure. A macrocyclic peptide refers to a closed-ring structure of a linear peptide intramolecularly formed by linkage between two positions in the peptide, referred to as linkage amino acids, linkage amino acid derivatives, linkage molecule, linkage moiety, linkage residue, linkage entity, or the like, as appropriate. The two linkage amino acids, linkage amino acid derivatives, linkage molecules, linkage moieties, linkage residues, or linkage entities are separated from each other by two or more amino acid residues, bound to each other directly, bound via a linker, or the like.

In embodiments, a linkage of a peptide antagonist of the invention is formed by two linkage amino acids, linkage amino acid derivatives, linkage molecules, linkage moieties, linkage residues, or linkage entities bound to each other by, e.g., a disulfide bond, a peptide bond, an alkyl bond, an alkenyl bond, an ester bond, a thioester bond, an ether bond, a thioether bond, a phosphonate ether bond, an azo bond, a C—S—C bond, a C=N—C bond, a C=N—C bond, an amide bond, a lactam bridge, a carbamoyl bond, an urea bond, a thiourea bond, an amine bond, a thioamide bond, or the like. The macrocyclization may be formed by a bond between an N-terminal amino acid and a C-terminal amino acid of a peptide, by a bond between a terminal amino acid and a non-terminal amino acid, or by a bond between non-terminal amino acids.

For convenience, reference to a specific amino acid involved in a linkage can use the nomenclature for the unlinked amino acid (e.g., the structure it may have prior to formation of a linkage). It is also understood that certain linkages, e.g., synthetic linkages, may not be formed by connecting two amino acids or derivatives as commonly referenced in the art. Therefore, references to linked amino acids herein may use the most closely approximating language to describe each involved chemical entity at a given residue position in the peptide antagonist. Correspondingly, linked entities in the peptide sequence, e.g., Xaa3, Xaa4, Xaa8, and Xaa14, may be referred to as linked amino acids, although they are not amino acids as commonly referenced in the art. In some embodiments, Xaa3 and Xaa8, and Xaa4 and Xaa14, when linked entities (e.g., forming an Xaa3-Xaa8 linkage and an Xaa4-Xaa14 linkage), can be referred to as linked (or linkage-forming) amino acids, linked (or linkage-forming) amino acid derivatives, linked (or linkage-forming) molecules, linked (or linkage-forming) moieties, linked (or linkage-forming) residues, or linked (or linkage-forming) entities in the alternative. These terms can be used to refer to amino acids, molecules, moieties, residues, or entities present at any of Xaa3, Xaa4, Xaa8, or Xaa14, in the alternative, either when linked or unlinked. For example, when not linked but intended to be linked in a peptide antagonist of the invention, two linkage amino acids also can be referred to as linked (or linkage-forming) amino acids, linked (or linkage-forming) amino acid derivatives, linked (or linkage-forming) molecules, linked (or linkage-forming) moieties, linked (or linkage-forming) residues, or linked (or linkage-forming) entities in the alternative. When linked, two linkage amino acids can be referred to as linked (or linkage-forming) amino acids, linked (or linkage-forming) amino acid derivatives, linked (or linkage-forming) molecules, linked (or linkage-forming) moieties, linked (or linkage-forming) residues, or linked (or linkage-forming) entities, in the alternative. When not linked and not intended to be linked, two amino acids can be referred to as unlinked (or non-linkage forming) amino acids, unlinked (or non-linkage forming) amino acid derivatives, unlinked molecules, unlinked moieties, unlinked residues, or unlinked entities. In some embodiments, each residue at a non-linked amino acid position in a peptide antagonist of the invention can be referred to as an amino acid, amino acid derivative, molecule, moiety, residue or entity, or as an unlinked (or non-linkage forming) amino acid, unlinked (or non-linkage forming) amino acid derivative, unlinked (or non-linkage forming) molecule, unlinked (or non-linkage forming) moiety, unlinked (or non-linkage forming) residue or unlinked (or non-linkage forming) entity.

Any constraining structure known to those of skill in the art is contemplated for linking the residues. Examples of constraining structures and their respective linkage residues include, but are not limited to linkages or bridges selected from: a disulfide bridge (e.g., a Cys-Cys linkage, wherein each linkage amino acid is a Cys); a Sec-Sec linkage (selenocysteine linkage, wherein each linkage amino acid is a selenocysteine); a cystathionine linkage or bridge (e.g., Ser-Homocysteine linkage), also referred to herein as Cyt-Cyt (e.g., $CH_2$—$CH_2$—S—$CH_2$); a lactam bridge (e.g., Asp-Lys or Glu-Lys linkage), a thioether linkage (e.g., a lanthionine linkage, including but not limited to Cys-dehydroalanine or methyl variant), and a dicarba linkage (e.g., a linkage of an olefin-containing amino acid, e.g., allyl glycine or prenyl glycine). In some embodiments, a linkage is selected from: a disulfide bridge having linkage residues Cys-Cys; a selenocysteine linkage having linkage residues Sec-Sec; a cystathionine linkage having linkage residues Ser-Homocysteine; a lactam bridge having residues Asp-Lys or Glu-Lys; a lanthionine linkage having linkage residues Cys-dehydroalanine or a methyl variant, and a dicarba linkage linkage having linkage residues allyl glycine or prenyl glycine. In embodiments, linkage amino acid, linkage amino acid derivative, linkage molecule, linkage moiety, linkage residue, or linkage entity is selected from Cys, Sec, Ser, Homocysteine, Asp, Lys, Glu, dehydroalanine, or an olefin containing amino acid (e.g., allyl glycine or prenyl glycine).

In some embodiments, each of the Xaa3-Xaa8 and the Xaa4-Xaa14 linkage of a peptide antagonist of the invention is a linkage that is independently selected from: a disulfide bridge formed by two Cys linkage residues, a Sec-Sec linkage formed by two selenocysteine linkage residues, a cystathionine linkage formed by Ser and homocysteine linkage residues, a lactam bridge formed by Asp and Lys linkage residues or Glu and Lys linkage residues, a thioether linkage that is a lanthionine linkage formed by Cys and dehydroalanine or methyl variant residues, a dicarba linkage formed by olefin-containing linkage residues, e.g., an allyl glycine or prenyl glycine linkage residue, or any of these linkages formed by linkage residues as known and described in the art. In some embodiments, the Xaa3-Xaa8 or Xaa4-Xaa14 linkages are the same as one another, or different.

(See, e.g., Knerr et al., 2011, "Synthesis and activity of thioether-containing analogues of the complement inhibitor compstatin," ACS Chem Biol. 6(7): 753-760; DiMarco et al., 2006, "Discovery of novel, highly potent and selective b-hairpin mimetic CXCR4 inhibitors with excellent anti-HIV activity and pharmacokinetic profiles," Bioorganic & Medicinal Chemistry 14: 8396-8404; Dekan et al., 2011, "α-Conotoxin ImI incorporating stable cystathionine bridges maintains full potency and identical three-dimensional structure," J. Am. Chem. Soc. 2011, 133: 15866-15869; Nguyen and Wong, 2017, "Making circles: recent advance in chemical and enzymatic approaches in peptide macrocyclization," Journal of Biochemistry and Chemical Sciences 1(1): 1-13; Tam and Wong, 2012, "Chemical Synthesis of Circular Proteins," The Journal of Biological Chemistry 287(32): 27020-27025, each incorporated herein by reference in its entirety.) In some embodiments, any appropriate constraining structure resulting from the use of linkage residues as known in the art is contemplated for use in a peptide antagonist of the invention.

In some embodiments, a particular constraining structure is selected based on its resistance to degradation, e.g., degradation caused by the reduction of a disulfide bond constraining structure. In some embodiments, the peptide antagonist comprises a constraining structure that resists degradation by reduction. For example, in a reducing environment a disulfide bond may be susceptible to degradation and a resulting loss of activity or other desired peptide antagonist property. In some embodiments, a cystathione linkage or a linkage of at least two $C_1$-$C_6$ heterocycloalkyl rings confers increased stability relative to a disulfide bond.

In some embodiments, two amino acids in a chain are joined by a linkage to create a macrocyclic ring structure. In some embodiments, a linkage mimics a hairpin turn in a peptide. In some embodiments, linkages comprise covalent bonds between canonical or non-canonical amino acids such as cystathionine linkages, lactam bridges, or thioether bridges (e.g., a lanthionine linkage). In some embodiments, a linkage comprises a dipeptide. In some embodiments, a linkage comprises covalent bonds between canonical or non-canonical acid amino acids such as lanthionine or methyllanthionine linkages. In some embodiments, a linkage comprises at least one aromatic or non-aromatic ring. In some embodiments, a linkage comprises at least one cycloalkyl ring. In some embodiments, a linkage comprises at least one heterocyclic ring. In some embodiments, a linkage comprises at least two heterocyclic rings. In some embodiments, a linkage comprises at least one nitrogen-containing heterocycloalkyl ring.

In some embodiments, a linkage comprises the structure

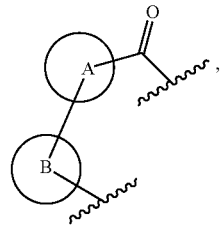

wherein A and B are heterocyclic rings. In some embodiments, a linkage comprises the structure

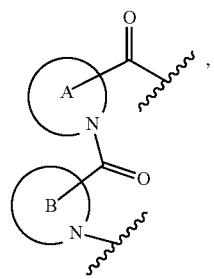

wherein A and B are heterocyclic rings.

In some embodiments, a linkage comprises pyrrolidine, piperidine, dehydropyrrolidine, dehydropiperidine, aziridine, azetidine, oxazolidine, or thiazolidine. In some embodiments, a linkage comprises two $C_1$-$C_6$ heterocycloalkyl rings. In some embodiments, a linkage comprises at least one five-membered heterocycloalkyl ring. In some embodiments, a linkage comprises at least one six-membered heterocycloalkyl ring. In some embodiments, a linkage comprises two five-membered heterocycloalkyl rings. In some embodiments, a linkage comprises two five-membered heterocycloalkyl rings, wherein each ring comprises at least one nitrogen atom. In some embodiments, a linkage comprises two five-membered heterocycloalkyl rings, wherein at least one ring comprises at least one nitrogen atom. In some embodiments, a linkage comprises two six-membered heterocycloalkyl rings. In some embodiments, the linkage comprises two $C_1$-$C_6$ heterocycloalkyl rings connected by an amide bond. In some embodiments, the linkage comprises two $C_1$-$C_6$ heterocycloalkyl rings connected by —C(=O)NH—. In some embodiments, a linkage comprises two pyrrolidine rings. In some embodiments, a linkage comprises at least one non-canonical amino (unnatural) acid residue. In some embodiments, a linkage comprises two amino acids (canonical or non-canonical), wherein a first amino acid has the (S) configuration at the alpha position, and the second amino acid has the (R) configuration at the alpha position. In some embodiments, a linkage comprises two amino acids (canonical or non-canonical) connected by a peptide bond. In some embodiments, a linkage comprises two proline residues (diproline linkage). In some embodiments, a linkage comprises two proline residues connected by a peptide bond. In some embodiments, a linkage comprises a D-proline and an L-proline (D-proline-L-proline or L-proline-D-proline).

In some embodiments, a linkage comprises a D-proline and an L-proline, or derivatives thereof. In some embodiments, such derivatives comprise substitutions to the pyrrolidine ring of a proline. In some embodiments, a linkage comprises a non-canonical amino acid residue selected from 3-fluoroproline, 4-fluoroproline, 3-hydroxyproline, 4-hydroxyproline, 3-aminoproline, 4-aminoproline, 3,4-dehydroproline, aziridine-2-carboxylic acid, azetidine-2-carboxylic acid, pipecolic acid, 4-oxa-proline, 3-thiaproline, or 4-thiaproline. In some embodiments, a linkage comprises two amino acids selected from proline, 3-fluoroproline, 4-fluoroproline, 3-hydroxyproline, 4-hydroxyproline, 3-aminoproline, 4-aminoproline, 3,4-dehydroproline, aziridine-2-carboxylic acid, azetidine-2-carboxylic acid, pipecolic acid, 4-oxa-proline, 3-thiaproline, or 4-thiaproline.

In some embodiments, a linkage comprises covalent bonds between canonical or non-canonical amino acids lactam bridges. In some embodiments, a linkage comprises the structure:

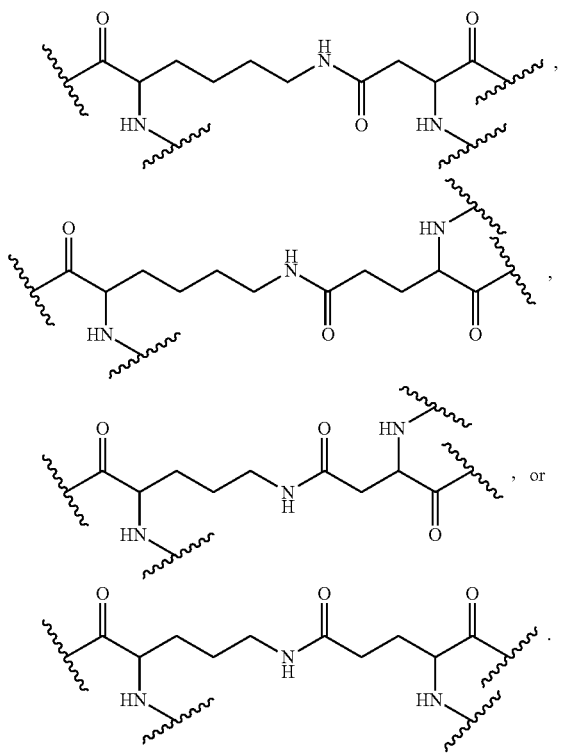

In some embodiments, a linkage comprises covalent bonds between canonical or non-canonical amino acids thioether bridges. In some embodiments, a linkage comprises the structure

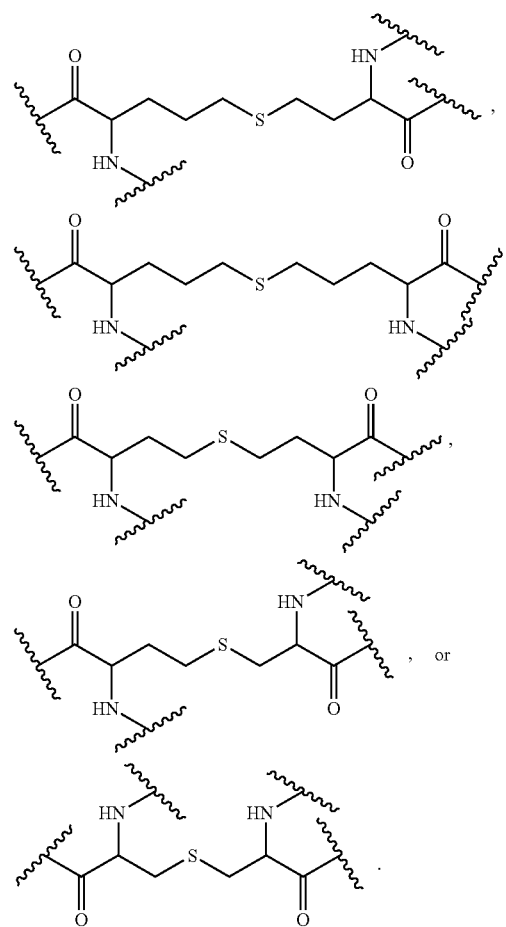

These and similar constraining structures can be used to link residues at terminal and/or nonterminal positions in the peptide. In some embodiments, Xaa3 and Xaa8 of a peptide antagonist of the invention are linked. In some embodiments, Xaa4 and Xaa14 of a peptide antagonist of the invention are linked. In some embodiments, Xaa3 and Xaa8, and Xaa4 and Xaa14, of a peptide antagonist of the invention are linked.

Linkage Spacing

In some embodiments, a constraining structure as described herein is selected based on the resulting spatial separation between the constrained residues. In some embodiments, the spatial separation influences a peptide antagonist property as described above. A peptide antagonist of the invention can comprise a constraining structure conferring a spatial separation of about 3.5 to about 10 Angstroms between alpha-carbons of the two linked amino acid residues, or between the geometrical centers of the two linked residues (e.g., amino acid derivatives). In some embodiments, the spatial separation between the alpha-carbons of the two linked amino acid residues, or the spatial separation between the geometrical centers of the two linked residues, is about 3.5 Ångströms to about 10 Ångströms. In some embodiments, the spatial separation between the alpha-carbons of the two linked amino acid residues, or the spatial separation between the geometrical centers of the two linked residues, is at least about 3.5 Ångströms. In some embodiments, the spatial separation between the alpha-carbons of the two linked amino acid residues, or the spatial separation between the geometrical centers of the two linked residues, is at most about 10 Ångströms. In some embodiments, the spatial separation between the alpha-carbons of the two linked amino acid residues, or the spatial separation between the geometrical centers of the two linked residues, is about 3.5 Ångströms to about 4.5 Ångströms, about 3.5 Ångströms to about 5 Ångströms, about 3.5 Ångströms to about 5.5 Ångströms, about 3.5 Ångströms to about 6 Ångströms, about 3.5 Ångströms to about 6.5 Ångströms, about 3.5 Ångströms to about 7 Ångströms, about 3.5 Ångströms to about 7.5 Ångströms, about 3.5 Ångströms to about 8 Ångströms, about 3.5 Ångströms to about 8.5 Ångströms, about 3.5 Ångströms to about 9 Ångströms, about 3.5 Ångströms to about 10 Ångströms, about 4.5 Ångströms to about 5 Ångströms, about 4.5 Ångströms to about 5.5 Ångströms, about 4.5 Ångströms to about 6 Ångströms, about 4.5 Ångströms to about 6.5 Ångströms, about 4.5 Ångströms to about 7 Ångströms, about 4.5 Ångströms to about 7.5 Ångströms, about 4.5 Ångströms to about 8 Ångströms, about 4.5 Ångströms to about 8.5 Ångströms, about 4.5 Ångströms to about 9 Ångströms, about 4.5 Ångströms to about 10 Ångströms, about 5 Ångströms to about 5.5 Ångströms, about 5 Ångströms to about 6 Ångströms, about 5 Ångströms to about 6.5 Ångströms, about 5 Ångströms to about 7 Ångströms, about 5 Ångströms to about 7.5 Ångströms, about 5 Ångströms to about 8 Ångströms, about 5 Ångströms to about 8.5 Ångströms, about 5 Ångströms to about 9 Ångströms, about 5 Ångströms to about 10 Ångströms, about 5.5 Ångströms to about 6 Ångströms, about 5.5 Ångströms to about 6.5 Ångströms, about 5.5 Ångströms to about 7 Ångströms, about 5.5 Ångströms to about 7.5 Ångströms, about 5.5 Ångströms to about 8 Ångströms, about 5.5 Ångströms to about 8.5 Ångströms, about 5.5 Ångströms to about 9 Ångströms, about 5.5 Ångströms to about 10 Ångströms, about 6 Ångströms to about 6.5 Ångströms, about 6 Ångströms to about 7 Ångströms, about 6 Ångströms to about 7.5 Ångströms, about 6 Ångströms to about 8 Ångströms, about 6 Ångströms to about 8.5 Ångströms, about 6 Ångströms to about 9 Ångströms, about 6 Ångströms to about 10 Ångströms, about 6.5 Ångströms to about 7 Ångströms, about 6.5 Ångströms to about 7.5 Ångströms, about 6.5 Ångströms to about 8 Ångströms, about 6.5 Ångströms to about 8.5 Ångströms, about 6.5 Ångströms to about 9 Ångströms, about 6.5 Ångströms to about 10 Ångströms, about 7 Ångströms to about 7.5 Ångströms, about 7 Ångströms to about 8 Ångströms, about 7 Ångströms to about 8.5 Ångströms, about 7 Ångströms to about 9 Ångströms, about 7 Ångströms to about 10 Ångströms, about 7.5 Ångströms to about 8 Ångströms, about 7.5 Ångströms to about 8.5 Ångströms, about 7.5 Ångströms to about 9 Ångströms, about 7.5 Ångströms to about 10 Ångströms, about 8 Ångströms to about 8.5 Ångströms, about 8 Ångströms to about 9 Ångströms, about 8 Ångströms to about 10 Ångströms, about 8.5 Ångströms to about 9 Ångströms, about 8.5 Ångströms to about 10 Ångströms, or about 9 Ångströms to about 10 Ångströms. In some embodiments, the spatial separation between the alpha-carbons of the two linked amino acid residues, or the spatial separation between the geometrical centers of the two linked residues, is about 3.5 Ångströms, about 4.5 Ångströms, about 5 Ångströms, about 5.5 Ångströms, about 6 Ångströms, about 6.5 Ångströms, about 7 Ångströms, about 7.5 Ångströms, about 8 Ångströms, about 8.5 Ångströms, about 9 Ångströms, or about 10 Ångströms. In embodiments, a specific spatial separation is achieved using a linker or spacer molecule, as known in the art.

Amino Acid Derivatives

The present invention contemplates the use of an amino acid derivative or analog of any amino acid in any of the peptide antagonists of the invention. In some embodiments, amino acid modifications can be made chemically using any known method. Selective protein modifications are described in the literature, e.g., by Spicer and Davis, 2014, "Selective chemical protein modification," Nature Communications 5: 4740, incorporated herein by reference.

In some embodiments, an amino acid derivative is a non-canonical amino acid. In some embodiments, a non-canonical amino acid has an (S) configuration at the alpha position. In some embodiments, a non-canonical amino acid has an (R) configuration at the alpha position. In some embodiments, a non-canonical amino acid is an alpha amino acid. In some embodiments, a non-canonical amino acid is a beta or gamma amino acid. In some embodiments, a non-canonical amino acid is selected from the group consisting of: an aromatic side chain amino acid; a non-aromatic side chain amino acid; an aliphatic side chain amino acid; a side chain amide amino acid; a side chain ester amino acid; a heteroaromatic side chain amino acid; a side chain thiol amino acid; a beta amino acid; and a backbone-modified amino acid. In some embodiments, a non-canonical amino acid is a derivative of tyrosine, histidine, tryptophan, or phenylalanine. In some embodiments, a derivative of an amino acid comprises an ester, amide, disulfide, carbamate, urea, phosphate, ether of the amino acid. In some embodiments, a non-aromatic side chain amino acid is a derivative of serine, threonine, cysteine, methionine, arginine, asparagine, glutamine, aspartic acid, glutamic acid, lysine, proline, glycine, alanine, valine, isoleucine, or leucine. In some embodiments, a non-canonical amino acid is selected from the group consisting of 2-aminoadipic acid; 3-aminoadipic acid; beta-alanine; beta-aminoproprionic acid; 2-aminobutyric acid; 4-aminobutyric acid; piperidinic acid; 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminoproprionic acid; N-ethylglycine; N-ethyl asparagine; hydroxylysine; allo-hydroxylysine; 3-hydroxyproline; 4-hydroxyproline; isodesmosine; allo-isoleucine; N-methylglycine; sarcosine; n-methylisoleucine; 6-N-methyllysine; N-methylvaline; norvaline; norleucine; and ornithine. In some embodiments, a non-canonical amino acid is a proline derivative. In some embodiments, a proline derivative is 3-fluoroproline, 4-fluoroproline, 3-hydroxyproline, 4-hydroxyproline, 3-aminoproline, 4-aminoproline, 3,4-dehydroproline, aziridine-2-carboxylic acid, azetidine-2-carboxylic acid, pipecolic acid, 4-oxa-proline, 3-thiaproline, or 4-thiaproline. In some embodiments, a non-canonical amino acid comprises a lipid.

In some embodiments, a peptide antagonist of the invention comprises one or more amino acid derivative or analog, e.g., as known to those of skill in the art and described in the literature or herein. In some embodiments, a peptide antagonist of the invention comprises 1, 2, 3, 4, 5, 6, 7, 8, 9, 10, 11, 12, 13, 14, 1-2, 1-3, 1-4, 1-5, 1-6, 1-7, 1-8, 1-9, 1-10, 1-11, 1-12, or 1-13 amino acid derivatives.

In some embodiments, each amino acid derivative present in a peptide antagonist of the invention is a non-canonical amino acid independently selected from the group consisting of: an aromatic side chain amino acid; a non-aromatic side chain amino acid; an aliphatic side chain amino acid; a side chain amide amino acid; a side chain ester amino acid; a heteroaromatic side chain amino acid; a side chain thiol amino acid; a beta amino acid; and a backbone-modified amino acid, selected from e.g., the non-canonical amino acids described herein or known in the art and described in the published literature.

In some embodiments, the peptide antagonist comprises one or more amino acids that have the D-amino acid configuration, and the remaining amino acids in the peptide have the L-amino acid configuration.

In some embodiments, a non-canonical amino acid is a proline derivative. In some embodiments, a proline derivative comprises one or more substitutions on the pyrrolidine ring. In some embodiments, a proline derivative comprises one or more substitutions on the pyrrolidine ring, wherein the substitutions comprise halogen, alkoxy, amino, hydroxyl, alkyl (methyl, ethyl), thiol, or alkylthio. In some embodiments, a proline derivative comprises one or more substitutions on the pyrrolidine ring, wherein the substitutions comprise halogen, or alkyl (methyl, ethyl). In some embodiments, a proline derivative comprises one or more substitutions on the pyrrolidine ring, wherein the substitutions comprise halogen. In some embodiments, a proline derivative comprises one or more substitutions on the pyrrolidine ring, wherein the substitutions comprise alkoxy, hydroxyl, amino. In some embodiments, a proline derivative comprises one or more substitutions on the pyrrolidine ring, wherein the substitutions comprise halogen, alkoxy, alkyl (methyl, ethyl), thiol, or alkylthio.

Peptide Antagonist Tracking

In some embodiments, a peptide antagonist of the present invention comprises a tracker amino acid derivative that facilitates tracking of the peptide antagonist. Detection of a noncanonical tracker amino acid present in the peptide antagonist during an assay or following administration of a peptide composition to a subject or patient can provide useful information regarding a peptide antagonist property, e.g., a pharmacokinetic property (including but not limited to absorption, bioavailability, distribution, metabolism, and excretion), a pharmacodynamic property (including but not limited to: receptor binding characteristics, e.g., binding half-life; postreceptor effects; and chemical interactions), enhanced activity (e.g., represented by $IC_{50}$), stability (e.g., represented by half-life), solubility (e.g., in a formulation), or permeability (e.g., permeability of the skin by a formulation containing the peptide antagonist).

In some embodiments, a peptide comprising a tracker amino acid derivative is detected using any assay appropriate for detecting the particular tracker amino acid derivative present in the peptide antagonist. In some embodiments, a tryptophan derivative is the tracker amino acid. In some embodiments, the assay comprises a spectroscopic or radiolabeling detection method. In some embodiments, the assay measures a pharmacokinetic or pharmacodynamic peptide antagonist property.

N-Terminal Modification of the Peptide Antagonist

In some embodiments, the N-terminus amino group of the peptide antagonist of the invention is modified (N-terminal modifications). In some embodiments, the N-terminus of the peptide antagonist is not modified with an additional amino acid or amino acid derivative. In some embodiments, an unmodified N terminus comprises hydrogen. In some embodiments, an N-terminal modification comprises $C_1$-$C_6$ acyl, $C_1$-$C_8$ alkyl, $C_6$-$C_{12}$ aralkyl, $C_5$-$C_{10}$ aryl, $C_4$-$C_8$ heteroaryl, formyl, or a lipid. In some embodiments, an N-terminal modification comprises $C_6$-$C_{12}$ aralkyl. In some embodiments, an N-terminal modification comprises $C_1$-$C_6$ acyl. In some embodiments, an N-terminal modification comprises acetyl (Ac). In some embodiments, an N-terminal modification comprises $C_1$-$C_6$ alkyl. In some embodiments, an N-terminal modification comprises methyl, ethyl, propyl, or tert-butyl. In some embodiments, an N-terminal modification comprises $C_1$-$C_6$ aralkyl. In some embodiments, an N-terminal modification comprises benzyl. In some embodiments, an N-terminal modification comprises formyl. In some embodiments, a peptide described herein, e.g., any peptide having an amino acid sequence as listed in Table 1 (irrespective of the N-terminus shown in the table), has any of these N-terminal modification or an unmodified N-terminus.

C-Terminal Modification of the Peptide Antagonist

In some embodiments, the C-terminus acid group of the peptide antagonist of the invention is modified (C-terminal modifications). In some embodiments, the C-terminus is not modified with an additional amino acid or amino acid derivative. In some embodiments, the C-terminus is not modified with a glycine residue. In some embodiments, an unmodified C terminus comprises —OH. In some embodiments, a C-terminal modification comprises an amino group, wherein the amino group is optionally substituted. In some embodiments, a C-terminal modification comprises an amino group, wherein the amino group is unsubstituted (—NH2). In some embodiments, a C-terminal modification comprises an amino group, wherein the amino group is substituted. In some embodiments, a C-terminal modification comprises —NH2, -amino-acyl, -amino-$C_1$-$C_8$ alkyl, -amino-$C_6$-$C_{12}$-aralkyl, -amino-$C_5$-$C_{10}$ aryl, or -amino-$C_4$-$C_8$ heteroaryl, -amino-$C_4$-$C_8$ heteroaryl, or —O—($C_1$-$C_8$ alkyl). In some embodiments, a C-terminal modification comprises -amino-$C_6$-$C_{12}$-aralkyl. In some embodiments, a C-terminal modification comprises —O—($C_1$-$C_8$ alkyl). In some embodiments, a C-terminal modification comprises -amino-$C_6$-$C_{12}$-aralkyl. In some embodiments, a C-terminal modification comprises —NH—$CH_2$Phenyl. In some embodiments, a C-terminal modification comprises —OEt. In some embodiments, a C-terminal modification comprises —OMe. In some embodiments, a peptide described herein, e.g., any peptide having an amino acid sequence as listed in Table 1 (irrespective of the C-terminus shown in the table), has any of these C-terminal modifications or an unmodified C-terminus.

In some embodiments, both the N-terminus amino group and the C-terminus acid group of the peptide antagonist of the invention are modified. In some embodiments, a peptide described herein, e.g., any peptide having an amino acid sequence as listed in Table 1 (irrespective of the N-and C-termini shown in the table), has N- and C-termini independently selected from any described herein. In some embodiments, a peptide described herein, e.g., any peptide having an amino acid sequence as listed in Table 1 (irrespective of the N- and C-termini shown in the table), has N- and C-termini independently selected from: Ac, $NH_2$, and H.

Lipids

In some embodiments, a peptide antagonist of the present invention comprises a lipid moiety. In some embodiments, the lipid moiety is covalently attached to an amino acid in the peptide. In some embodiments, a lipid is attached to the N-terminus. In some embodiments, a lipid is attached to a cysteine, serine, lysine, threonine or tyrosine residue of the peptide antagonist (also referred to herein as "cys-lipid," "ser-lipid," "lys-lipid," "thr-lipid," or "tyr-lipid," respectively). In some embodiments, the lipid is covalently attached to a cysteine or lysine residue of the peptide antagonist. In some embodiments, a lipid is attached to a non-canonical amino acid. In some embodiments, a lipid comprises a hydrophobic group. In some embodiments, a lipid comprises a fatty acid group. In some embodiments, a lipid comprises a $C_6$-$C_{20}$ fatty acid group. In some embodiments, a lipid comprises a steroid. In some embodiments, a lipid comprises a wax. In some embodiments, a lipid comprises an alkyl group. In some embodiments, the lipid comprises a $C_6$-$C_{20}$ alkyl, $C_6$-$C_{20}$ alkenyl, $C_6$-$C_{20}$ alkynyl, or $C_6$-$C_{20}$ acyl group. In some embodiments, the lipid comprises one or more isoprenyl moieties. In some embodiments, the lipid comprises a geranyl, farnesyl, or geranylgeranyl group. In some embodiments, the lipid comprises an undecyloyl, lauroyl, tridecyloyl, myristoyl, palmitoyl, or stearoyl group. In some embodiments, a peptide described herein comprises an ester, amide, or thioester of a fatty acid.

In some embodiments, the lipid is a covalent modification of cysteine added by palmitoylation. In some embodiments, the lipid added by palmitoylation is a $C_6$-$C_{20}$ alkyl or a palmitoyl group.

In some embodiments, the lipid is a covalent modification of cysteine added by prenylation. In some embodiments, the lipid added by prenylation is a $C_6$-$C_{20}$ alkenyl, geranyl, farnesyl, or geranylgeranyl group.

In some embodiments, a cys-lipid has Structure I or II.

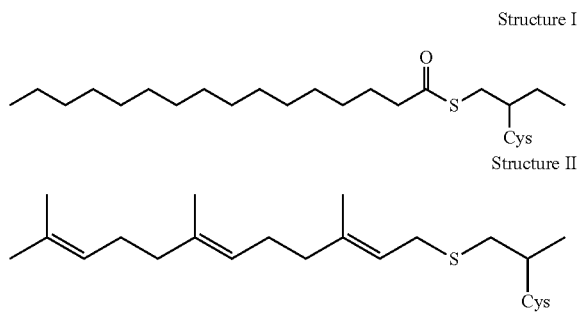

Structure I

Structure II

Evaluation of Peptide Antagonists

In some embodiments, a peptide antagonist of the invention is assayed to evaluate one or more peptide properties including but not limited to a pharmacokinetic property (e.g., absorption, bioavailability, distribution, metabolism, excretion, and the like), a pharmacodynamic property (including: receptor binding characteristics, e.g., binding half-life; postreceptor effects; chemical interactions, and the like), enhanced activity (e.g., represented by $IC_{50}$), stability (e.g., represented by half-life), solubility (e.g., in a formulation), or permeability (e.g., permeability of the skin by a formulation containing the peptide antagonist).

Natural muscle-type nAChR antagonists have been identified, e.g., alpha-conotoxins (described in, e.g., U.S. Pat. No. 8,735,541, "α-Conotoxin peptides," incorporated by reference herein), alpha-Bungarotoxin, from the snake *Bungarus multicinctus* (described by, e.g., Albuquerque, et al., 2009, incorporated by reference herein), neurotoxin LC-a, from the snake *Laticauda colubrina* (described by, e.g., Kim and Tamiya, 1982, Biochem. J. 207: 215-223, incorporated by reference herein), and neurotoxin azemiopsin, from the snake *Azemiops feae* (described by, e.g., Utkin, et al., 2012, Azemiopsin from Azemiops feae Viper Venom, a Novel Polypeptide Ligand of Nicotinic Acetylcholine Receptor, J. of Biol. Chem. 287(32):27079-27086, incorporated by reference herein).

In some embodiments, any in vivo or in vitro assay known in the art appropriate for testing a potential peptide antagonist's effect on an ion channel protein is contemplated for use in evaluating a peptide antagonist of the invention. In some embodiments, the binding of a peptide antagonist to the muscle nAChr receptor is assayed, e.g., in a competitive binding assay. In some embodiments, a flux-based assay is used to assess a change in ion channel activity. In some embodiments, an electrophysiological assay is used to measure the potency of peptide antagonist-channel interactions by providing data of ion channel function at the single cell or single channel level, within a small patch of membrane. In some embodiments, the electrophysiological assay is an automated assay. In some embodiments, the automated assay uses a commercially-available platforms, e.g., PatchXpress and IonFlux (Molecular Devices, LLC, Sunnyvale, Calif., USA), QPatch HT/HTX (Sophion, Copenhagen), or Patchliner and SynchroPatch (Nanion Technologies GmbH, Munich). In some embodiments, a fluorescence-based assay that measures the membrane-potential dependent or ion-concentration-dependent changes of fluorescence. In some embodiments, a voltage-sensitive dye assay is used to measure voltage changes across the cellular membrane using either the potential-dependent accumulation and redistribution. In some embodiments, an ion-specific fluorescent probe is used in an assay that measures intracellular ionic concentrations or the fluorescence resonance energy transfer (FRET) mechanism. In some embodiments, the assay is a high-throughput assay.

Other assays useful in evaluating a property of the peptide antagonists of the present invention include, e.g., skin and tissue penetration assays. In some embodiments, an assay measures the apparent treatment effect in a subject, e.g., assessment of a potential reduction in skin wrinkling can be used to evaluate a peptide antagonist. Specific exemplary assays for evaluating a peptide antagonist of the invention are described in detail herein in the Examples.

In some embodiments, a peptide antagonist is compared in an assay to a control. In some embodiments, the control is a negative control, e.g., a random peptide. In some embodiments, the control is positive control. In some embodiments, the control is any muscle nAChR peptide antagonist known in the art. In some embodiments, the control is any muscle nAChR peptide antagonist known in the art having a characterized activity level. In embodiments, the control peptide is a peptide set forth as any of SEQ ID NOS: 1-3 and 53-59. In embodiments, the control is, e.g., Glu-Cys-Cys-Asn-Pro-Ala-Cys-Gly-Arg-His-Tyr-Ser-Cys (SEQ ID NO: 1); Glu-Cys-Cys-Asn-Pro-Ala-Cys-Gly-Lys-His-Phe-Ser-Cys (SEQ ID NO: 2); or Gly-Arg-Cys-Cys-His-Pro-Ala-Cys-Gly-Lys-Asn-Tyr-Ser-Cys (SEQ ID NO: 3) or an inactivated or less toxic form thereof. In some embodiments, a useful control is a peptide as described in U.S. Pat. No. 9,550,808 (see, e.g., FIG. 2 therein) and in International Pub. No. WO 2017/102588, "Novel Use," each incorporated herein by reference herein in its entirety. In some embodiments, a control peptide has the amino acid sequence Trp-Tyr-Pro-Lys-Pro (SEQ ID NO: 53), described in U.S. Pat. No. 9,550,808, Gly-Pro-Arg-Pro-Ala (SEQ ID NO: 54) (Vialox® [INCI: Pentapeptide-3], marketed by Pentapharm/DS M), or (Syn®-Ake [INCI: Dipeptide Diaminobutyroyl Benzylamide Diacetate], marketed by Pentapharm/DSM). In some embodiments, the control is a muscle nAChR inhibitor that acts by a different mechanism, e.g., Inyline™ [INCI: Acetyl Hexapeptide-30] (marketed by Lipotec), which interferes with the clustering of the acetylcholine receptor.

In some embodiments, a peptide antagonist of the present invention preferentially inhibits the muscle nAChR over the neuronal nAChR.

In some embodiments, the muscle-type nicotinic acetylcholine receptor peptide antagonist selectively inhibits a muscle-type nicotinic acetylcholine receptor. In related embodiments, the peptide antagonist has an $IC_{50}$ of about 1 millimolar to about 1 picomolar.

In some embodiments, the $IC_{50}$ is about 1 millimolar to about 1 micromolar, about 1 millimolar to about 500 micromolar, about 500 micromolar to about 100 micromolar, about 100 micromolar to about 1 micromolar, about 1 micromolar to about 1 nanomolar, about 1 micromolar to about 1 nanomolar, about 1 micromolar to about 500 nanomolar, about 500 nanomolar to about 100 nanomolar, about 100 nanomolar to about 1 nanomolar, about about 1 nanomolar to about 1 picomolar, about 1 nanomolar to about 500 picomolar, about 500 picomolar to about 100 picomolar, about 100 micomolar to about 1 picomolar, about or less than about 1 millimolar, about or less than about 500 millimolar, about or less than about 100 millimolar, about or less than about 1 millimolar, about or less than about 1 micromolar, about or less than about 500 micromolar, about or less than about 100 micromolar, about or less than about 50 micromolar, about or less than about 20 micromolar, about or less than about 10 micromolar, about or less than about 5 micromolar, about or less than about 2 micromolar, about or less than about 1 micromolar, about or less than about 1 nanomolar, about or less than about 500 nanomolar, about or less than about 100 nanomolar, about or less than about 1 nanomolar, about or less than about 1 picomolar, about or less than about 500 picomolar, about or less than about 100 picomolar, or about or less than about 1 picomolar. In some embodiments, the $IC_{50}$ is about 20 nanomolar to about 125 nanomolar. In some embodiments, the $IC_{50}$ is about 20 nanomolar to about 25 nanomolar, about 20 nanomolar to about 30 nanomolar, about 20 nanomolar to about 40 nanomolar, about 20 nanomolar to about 50 nanomolar, about 20 nanomolar to about 60 nanomolar, about 20 nanomolar to about 70 nanomolar, about 20 nanomolar to about 75 nanomolar, about 20 nanomolar to about 80 nanomolar, about 20 nanomolar to about 90 nanomolar, about 20 nanomolar to about 100 nanomolar, about 20 nanomolar to about 125 nanomolar, about 25 nanomolar to about 30 nanomolar, about 25 nanomolar to about 40 nanomolar, about 25 nanomolar to about 50 nanomolar, about 25 nanomolar to about 60 nanomolar, about 25 nanomolar to about 70 nanomolar, about 25 nanomolar to about 75 nanomolar, about 25 nanomolar to about 80 nanomolar, about 25 nanomolar to about 90 nanomolar, about 25 nanomolar to about 100 nanomolar, about 25 nanomolar to about 125 nanomolar, about 30 nanomolar to about 40 nanomolar, about 30 nanomolar to about 50 nanomolar, about 30 nanomolar to about 60 nanomolar, about 30 nanomolar to about 70 nanomolar, about 30 nanomolar to about 75 nanomolar, about 30 nanomolar to about 80 nanomolar, about 30 nanomolar to about 90 nanomolar, about 30 nanomolar to about 100 nanomolar, about 30 nanomolar to about 125 nanomolar, about 40 nanomolar to about 50 nanomolar, about 40 nanomolar to about 60 nanomolar, about 40 nanomolar to about 70 nanomolar, about 40 nanomolar to about 75 nanomolar, about 40 nanomolar to about 80 nanomolar, about 40 nanomolar to about 90 nanomolar, about 40 nanomolar to about 100 nanomolar, about 40 nanomolar to about 125 nanomolar, about 50 nanomolar to about 60 nanomolar, about 50 nanomolar to about 70 nanomolar, about 50 nanomolar to about 75 nanomolar, about 50 nanomolar to about 80 nanomolar, about 50 nanomolar to about 90 nanomolar, about 50 nanomolar to about 100 nanomolar, about 50 nanomolar to about 125 nanomolar, about 60 nanomolar to about 70 nanomolar, about 60 nanomolar to about 75 nanomolar, about 60 nanomolar to about 80 nanomolar, about 60 nanomolar to about 90 nanomolar, about 60 nanomolar to about 100 nanomolar, about 60 nanomolar to about 125 nanomolar, about 70 nanomolar to about 75 nanomolar, about 70 nanomolar to about 80 nanomolar, about 70 nanomolar to about 90 nanomolar, about 70 nanomolar to about 100 nanomolar, about 70 nanomolar to about 125 nanomolar, about 75 nanomolar to about 80 nanomolar, about 75 nanomolar to about 90 nanomolar, about 75 nanomolar to about 100 nanomolar, about 75 nanomolar to about 125 nanomolar, about 80 nanomolar to about 90 nanomolar, about 80 nanomolar to about 100 nanomolar, about 80 nanomolar to about 125 nanomolar, about 90 nanomolar to about 100 nanomolar, about 90 nanomolar to about 125 nanomolar, or about 100 nanomolar to about 125 nanomolar. In some embodiments, the $IC_{50}$ is about 20 nanomolar, about 25 nanomolar, about 30 nanomolar, about 40 nanomolar, about 50 nanomolar, about 60 nanomolar, about 70 nanomolar, about 75 nanomolar, about 80 nanomolar, about 90 nanomolar, about 100 nanomolar, or about 125 nanomolar. In some embodiments, the $IC_{50}$ is at least about 20 nanomolar, about 25 nanomolar, about 30 nanomolar, about 40 nanomolar, about 50 nanomolar, about 60 nanomolar, about 70 nanomolar, about 75 nanomolar, about 80 nanomolar, about 90 nanomolar, or about 100 nanomolar. In some embodiments, the $IC_{50}$ is at most about 25 nanomolar, about 30 nanomolar, about 40 nanomolar, about 50 nanomolar, about 60 nanomolar, about 70 nanomolar, about 75 nanomolar, about 80 nanomolar, about 90 nanomolar, about 100 nanomolar, or about 125 nanomolar.

In some embodiments, the $IC_{50}$ of the peptide antagonist is about 25 nanomolar to about 150 nanomolar. In some embodiments, the $IC_{50}$ of the peptide antagonist is at least about 25 nanomolar. In some embodiments, the $IC_{50}$ of the peptide antagonist is at most about 150 nanomolar. In some embodiments, the $IC_{50}$ of the peptide antagonist is about 25 nanomolar to about 35 nanomolar, about 25 nanomolar to about 40 nanomolar, about 25 nanomolar to about 45 nanomolar, about 25 nanomolar to about 50 nanomolar, about 25 nanomolar to about 60 nanomolar, about 25 nanomolar to about 70 nanomolar, about 25 nanomolar to about 75 nanomolar, about 25 nanomolar to about 100 nanomolar, about 25 nanomolar to about 110 nanomolar, about 25 nanomolar to about 125 nanomolar, about 25 nanomolar to about 150 nanomolar, about 35 nanomolar to about 40 nanomolar, about 35 nanomolar to about 45 nanomolar, about 35 nanomolar to about 50 nanomolar, about 35 nanomolar to about 60 nanomolar, about 35 nanomolar to about 70 nanomolar, about 35 nanomolar to about 75 nanomolar, about 35 nanomolar to about 100 nanomolar, about 35 nanomolar to about 110 nanomolar, about 35 nanomolar to about 125 nanomolar, about 35 nanomolar to about 150 nanomolar, about 40 nanomolar to about 45 nanomolar, about 40 nanomolar to about 50 nanomolar, about 40 nanomolar to about 60 nanomolar, about 40 nanomolar to about 70 nanomolar, about 40 nanomolar to about 75 nanomolar, about 40 nanomolar to about 100 nanomolar, about 40 nanomolar to about 110 nanomolar, about 40 nanomolar to about 125 nanomolar, about 40 nanomolar to about 150 nanomolar, about 45 nanomolar to about 50 nanomolar, about 45 nanomolar to about 60 nanomolar, about 45 nanomolar to about 70 nanomolar, about 45 nanomolar to about 75 nanomolar, about 45 nanomolar to about 100 nanomolar, about 45 nanomolar to about 110 nanomolar, about 45 nanomolar to about 125 nanomolar, about 45 nanomolar to about 150 nanomolar, about 50 nanomolar to about 60 nanomolar, about 50 nanomolar to about 70 nanomolar, about 50 nanomolar to about 75 nanomolar, about 50 nanomolar to about 100 nanomolar, about 50 nanomolar to about 110 nanomolar, about 50 nanomolar to about 125 nanomolar, about 50 nanomolar to about 150 nanomolar, about 60 nanomolar to about 70 nanomolar, about 60 nanomolar to about 75 nanomolar, about 60 nanomolar to about 100 nanomolar, about 60 nanomolar to about 110 nanomolar, about 60 nanomolar to about 125 nanomolar, about 60 nanomolar to about 150 nanomolar, about 70 nanomolar to about 75 nanomolar, about 70 nanomolar to about 100 nanomolar, about 70 nanomolar to about 110 nanomolar, about 70 nanomolar to about 125 nanomolar, about 70 nanomolar to about 150 nanomolar, about 75 nanomolar to about 100 nanomolar, about 75 nanomolar to about 110 nanomolar, about 75 nanomolar to about 125 nanomolar, about 75 nanomolar to about 150 nanomolar, about 100 nanomolar to about 110 nanomolar, about 100 nanomolar to about 125 nanomolar, about 100 nanomolar to about 150 nanomolar, about 110 nanomolar to about 125 nanomolar, about 110 nanomolar to about 150 nanomolar, or about 125 nanomolar to about 150 nanomolar. In some embodiments, the $IC_{50}$ of the peptide antagonist is about 25 nanomolar, about 35 nanomolar, about 40 nanomolar, about 45 nanomolar, about 50 nanomolar, about 60 nanomolar, about 70 nanomolar, about 75 nanomolar, about 100 nanomolar, about 110 nanomolar, about 125 nanomolar, or about 150 nanomolar.

In some embodiments, the $IC_{50}$ is determined by any appropriate activity assay as described herein or known in the art. In some embodiments, the $IC_{50}$ represents the concentration of peptide antagonist at which 50% of the current through the receptor channel is blocked.

In some embodiments, the $IC_{50}$ observed using a peptide antagonist of the invention is lower than that of a control muscle nAChR peptide antagonist. In some embodiments, control peptide antagonist of the invention is a muscle nAChR peptide antagonist known in the art. In some embodiments, the $IC_{50}$ observed using a peptide antagonist of the invention is lower than that of a muscle nAChR peptide antagonist known in the art by about 2× to about 10×, or more, i.e., the $IC_{50}$ is 50% to 20% that observed in a muscle nAChR peptide antagonist known in the art. In some embodiments, this effect is observed relative to a muscle nAChR peptide antagonist as described in U.S. Pat. No. 9,550,808, "Peptide inhibitors of nicotinic acetylcholine receptor," (e.g., those shown in FIG. 2 therein) and in International Pub. No. WO 2017/102588, "Novel Use," each incorporated herein by reference herein in its entirety. In some embodiments, a control peptide has the amino acid sequence Trp-Tyr-Pro-Lys-Pro (SEQ ID NO: 53), described in U.S. Pat. No. 9,550,808. In embodiments, the control peptide is a peptide set forth as any of SEQ ID NOS: 1-3 and 53-59.

In some embodiments, the control peptide is Conotoxin GI (CGI, SEQ ID NO: 1). In some embodiments, the control peptide is Conotoxin MI (CMI, SEQ ID NO: 3). In some embodiments, the peptide antagonist of the invention has an $IC_{50}$ that is lower than the $IC_{50}$ observed for a control, e.g., CGI, CMI, or both. In some embodiments, the peptide antagonist of the invention has an $IC_{50}$ that is lower than the $IC_{50}$ observed for a control, e.g., CGI, CMI, or both, by about 1.25-fold to about 8-fold. In some embodiments, the peptide antagonist of the invention has an $IC_{50}$ that is lower than the $IC_{50}$ observed for a control, e.g., CGI, CMI, or both, by at least about 1.25-fold. In some embodiments, the peptide antagonist of the invention has an $IC_{50}$ that is lower than the $IC_{50}$ observed for a control, e.g., CGI, CMI, or both, by at most about 8-fold. In some embodiments, the peptide antagonist of the invention has an $IC_{50}$ that is lower than the $IC_{50}$ observed for a control, e.g., CGI, CMI, or both, by about 1.25-fold to about 1.5-fold, about 1.25-fold to about 2-fold, about 1.25-fold to about 2.5-fold, about 1.25-fold to about 3-fold, about 1.25-fold to about 4-fold, about 1.25-fold to about 4.5-fold, about 1.25-fold to about 5-fold, about 1.25-fold to about 6-fold, about 1.25-fold to about 7-fold, about 1.25-fold to about 7.5-fold, about 1.25-fold to about 8-fold, about 1.5-fold to about 2-fold, about 1.5-fold to about 2.5-fold, about 1.5-fold to about 3-fold, about 1.5-fold to about 4-fold, about 1.5-fold to about 4.5-fold, about 1.5-fold to about 5-fold, about 1.5-fold to about 6-fold, about 1.5-fold to about 7-fold, about 1.5-fold to about 7.5-fold, about 1.5-fold to about 8-fold, about 2-fold to about 2.5-fold, about 2-fold to about 3-fold, about 2-fold to about 4-fold, about 2-fold to about 4.5-fold, about 2-fold to about 5-fold, about 2-fold to about 6-fold, about 2-fold to about 7-fold, about 2-fold to about 7.5-fold, about 2-fold to about 8-fold, about 2.5-fold to about 3-fold, about 2.5-fold to about 4-fold, about 2.5-fold to about 4.5-fold, about 2.5-fold to about 5-fold, about 2.5-fold to about 6-fold, about 2.5-fold to about 7-fold, about 2.5-fold to about 7.5-fold, about 2.5-fold to about 8-fold, about 3-fold to about 4-fold, about 3-fold to about 4.5-fold, about 3-fold to about 5-fold, about 3-fold to about 6-fold, about 3-fold to about 7-fold, about 3-fold to about 7.5-fold, about 3-fold to about 8-fold, about 4-fold to about 4.5-fold, about 4-fold to about 5-fold, about 4-fold to about 6-fold, about 4-fold to about 7-fold, about 4-fold to about 7.5-fold, about 4-fold to about 8-fold, about 4.5-fold to about 5-fold, about 4.5-fold to about 6-fold, about 4.5-fold to about 7-fold, about 4.5-fold to about 7.5-fold, about 4.5-fold to about 8-fold, about 5-fold to about 6-fold, about 5-fold to about 7-fold, about 5-fold to about 7.5-fold, about 5-fold to about 8-fold, about 6-fold to about 7-fold, about 6-fold to about 7.5-fold, about 6-fold to about 8-fold, about 7-fold to about 7.5-fold, about 7-fold to about 8-fold, or about 7.5-fold to about 8-fold. In some embodiments, the peptide antagonist of the invention has an $IC_{50}$ that is lower than the $IC_{50}$ observed for a control, e.g., CGI, CMI, or both, by about 1.25-fold, about 1.5-fold, about 2-fold, about 2.5-fold, about 3-fold, about 4-fold, about 4.5-fold, about 5-fold, about 6-fold, about 7-fold, about 7.5-fold, or about 8-fold.

In some embodiments, a property of a peptide antagonist of the invention as measured in an activity assay described herein or known in the art is improved relative to that measured in the same or comparable assay using a different muscle nAChR peptide antagonist known in the art. In some embodiments, the improvement is by about 2× to about 10×, or more.

Indications

The peptide antagonists of the invention are contemplated for cosmetic uses in a subject, for indications including but not limited to the prevention or temporary improvement of the appearance of one or more of: skin wrinkles; skin laxity; moderate to severe glabellar lines associated with corrugator and/or procerus muscle activity; moderate to severe lateral canthal lines associated with orbicularis oculi activity (crow's feet lines); and moderate to severe forehead lines associated with frontalis muscle activity.

In some embodiments, peptide antagonists of the invention are contemplated for use in any cosmetic indication for which onabotulinum toxin A (BTX-A) has been approved by a regulatory authority. Currently approved indications for onabotulinum toxin A cosmetic are available from the U.S. Food and Drug Administration (10903 New Hampshire Avenue, Silver Spring, Md. 20993).

The peptide antagonists of the invention are contemplated for pharmaceutical use in a subject, for indications including but not limited to: prevention or temporary improvement of the appearance of one or more of skin wrinkles, e.g., in the face, skin laxity, moderate to severe glabellar lines associated with corrugator and/or procerus muscle activity, moderate to severe lateral canthal lines associated with orbicularis oculi activity (crow's feet lines), and moderate to severe forehead lines associated with frontalis muscle activity; treatment of overactive bladder (OAB); treatment of urinary incontinence; prophylaxis of headaches; treatment of spasticity; treatment of cervical dystonia; treatment of hypersalivation (also called ptyalism or sialorrhea); treatment of blepharospasm associated with dystonia; and treatment of strabismus.

In some embodiments, the subject is a mammal. In specific embodiments, the mammal is a human. In some embodiments, the human subject is a pediatric or adult subject, of any age.

Formulations

Peptide antagonists of the invention can be provided in a cosmetic or pharmaceutical composition. In some embodiments, cosmetic or pharmaceutical compositions of the invention are: formulated using excipients or carriers that are not toxic to keratinous tissue, e.g., skin, and are cosmetically, pharmaceutically and/or dermatologically acceptable; and administered in treatments comprising a subimmunological dose of the composition.

Administration of a formulation of the invention, e.g., a cosmetic or pharmaceutical composition, to a subject is not expected to result in adverse effects, even when administered repeatedly and often, e.g., as described herein. In embodiments, adverse effects are minor, few, or nonexistent. Adverse effects of topical application can include, e.g., mild to severe skin pain, redness, burning, itching, irritation, or any other side effects commonly associated with topical compositions. More severe effects avoided by formulations of the invention can include side effects associated with injectable neurotoxins as described in product labeling, e.g., as referenced herein.

Cosmetic and Pharmaceutical Compositions

The present invention includes a cosmetic composition comprising a peptide antagonist of the invention. In some embodiments, the cosmetic composition is formulated for topical administration. In some embodiments, the cosmetic composition is formulated for topical administration as a cream, balm, gel, solution, serum, cosmetic, liquid, lotion, ointment, emulsion, milk, spray, mask, or the like.

In some embodiments, a topical cosmetic or pharmaceutical composition comprises an excipient or carrier or a suitable combination of 2, 3, or more excipients or carriers. In some embodiments, any appropriate excipient or carrier or combination of multiple excipients and/or carriers is selected from excipients known to those of skill in the art and described in the literature, e.g., those useful in a topical formulation. In some embodiments, an excipient or carrier useful in a topical formulation is selected from the group consisting of: an inert excipient or carrier, a buffer, an absorption enhancer (penetrating agent), and a stability enhancer. In some embodiments, the inert excipient or carrier is water, isopropyi alcohol, gaseous fluorocarbons, ethyl alcohol, polyvinyl pyrrolidone, propylene glycol, a fragrance, a gel-producing material, stearyl alcohol, stearic acid, spermaceti, sorbitan monooleate, or methylcellulose. In some embodiments, the excipient is an inorganic compound. In some embodiments, an excipient is a carbohydrate. In some embodiments, the excipient is diaminobutyroyl benzylamide, diacetate, glycerin, a gum, a hydrophilic colloid or derivative, a cellulosic derivative, an emulsifier, a fatty alcohol, an acrylic derivative, a mineral, a surfactant, a fat, an oil, a preservative, a monosaccharide, a disaccharide, a polysaccharide, a glycosaminoglycan, or a chelating agent.

In some embodiments, the absorption enhancer is selected from the group consisting of: a liposome delivery system, a transfersome delivery system, an ethosome delivery system, a short chain alcohol, a long chain alcohol, a polyalcohol, urea, an amino acid, an amino acid ester, an amine, an amide, an azacyclo compound (e.g., 1-dodecylazacycloheptan-2-one (AZONE®) or a derivative of 1-dodecylazacycloheptan-2-one) a pyrrolidone, a pyrrolidone derivative, a terpene, a terpene derivative, a fatty acid, a fatty acid ester, a macrocyclic compound, a tenside, a sulfoxide, lecithin vesicles, water surfactants, a polyol, a small molecule tri, tetra, penta, hexa, septa or octa peptide, isoceteth-20, ethoxydiglycol, dimethyl sulfoxide (DMSO), dimethyl isosorbide, and phloretin. In some embodiments, the absorption enhancer is selected to have a minimal allergic or irritating effect.

In some embodiments, the stability enhancer is a small molecule peptide. In some embodiments, the small molecule peptide is selected from the group consisting of: a tripeptide, a tetrapeptide, a pentapeptide, a hexapeptide, a septapeptide, an octapeptide, Acetyl Hexapeptide-3 Cosmetic Topical Peptide, Melanotan II, ACVR2B (ACE-031), Argireline® Acetate, Argireline, Matrixyl Acetate (palmitoyl pentapeptide), peptide GHK spontaneously complexes with copper, Palmitoyl Tetrapeptide-3, Argireline, Acetyl Glutamyl Heptapeptide, Matrixyl™, Snap-8, Syn®-Tacks, Syn®-Coll, Syn®-Hycan, Leuphasyl®, Pepha®-Tight, Tego® Pep 4-17 and Trylagen®.

In some embodiments, the cosmetic composition further comprises one or more additional active ingredient. In some embodiments, the one or more additional active ingredient is selected from the group consisting of: a second, different, muscle-type nicotinic acetylcholine receptor peptide antagonist, an anti-wrinkle agent, a retinoid, an antioxidant, a retinoid, a growth factor, a collagen stimulating peptide, a carrier peptide, a peptide that inhibits tTAT-superoxide dismutase, a peptide that inhibits a proteinase, a peptide that stimulates hyaluronan synthase 2, and a keratin-based peptide.

In some embodiments, the cosmetic composition comprises a liposome delivery system. In some embodiments, the liposome delivery system can include, e.g., oil-in-water emulsions, micelles, mixed micelles, or liposomes. In some embodiments, a colloidal system is a liposome or microsphere. In some embodiments, a composition is formulated as a poly(D,L)lactide microspheres. In some embodiments the cosmetic composition is formulated to incorporate features as described below, for use in a pharmaceutical composition.

In some embodiments, the excipient(s) and/or liposome delivery system are selected using methods known to those of skill in the art to achieve the desired degree of penetration, e.g., to achieve substantially local delivery.

The present invention also includes pharmaceutical compositions comprising a peptide antagonist of the invention. In some embodiments, the pharmaceutical composition is formulated as described above for a cosmetic composition comprising a peptide antagonist of the invention. In some embodiments, the pharmaceutical composition is formulated for local injection, e.g., intradermal, intradetrusor, or subcutaneous injection. In some embodiments, the pharmaceutical composition may comprise a physiologically compatible saline solution. In some embodiments, an injectable pharmaceutical composition may comprise any one or more appropriate excipient, carrier, additive, or the like, as known to those of skill in the art and described in the literature.

In some embodiments, the composition is encapsulated in a slow release delivery vehicle suitable for local injection, e.g., a colloidal dispersion system or in polymer stabilized crystals. A colloidal dispersion system can include, e.g., nanocapsules, microspheres, beads, and lipid-based systems. Lipid-based systems (liposome delivery systems) include, e.g., oil-in-water emulsions, micelles, mixed micelles, and liposomes. In some embodiments, a colloidal system is a liposome or microsphere. In some embodiments, a composition is formulated as a poly(D,L)lactide microspheres.

In some embodiments, a cosmetic or pharmaceutical composition of the invention is formulated using any excipient, carrier, or additive as appropriate for the route of administration as described in, e.g, the most recent edition of e.g., Remington: The Science and Practice of Pharmacy, L. Allen, ed., $22^{nd}$ edition, and in U.S. Pat. No. 9,815,875, "Postsynaptically targeted chemodenervation agents and their methods of use," both incorporated by reference herein.

Methods for Using Cosmetic or Pharmaceutical Compositions

The present invention also relates to methods for using cosmetic or pharmaceutical compositions comprising a peptide antagonist of the invention. In some embodiments, the invention relates to methods for using the cosmetic or pharmaceutical composition to prevent or temporarily improve the appearance in a subject of one or more of skin wrinkles, e.g., in the face, skin laxity, moderate to severe glabellar lines associated with corrugator and/or procerus muscle activity, moderate to severe lateral canthal lines associated with orbicularis oculi activity (crow's feet lines), and moderate to severe forehead lines associated with frontalis muscle activity, comprising applying an effective amount of the cosmetic or pharmaceutical composition to the skin of the subject.

In some embodiments, the cosmetic or pharmaceutical composition is topically applied to a subject. Topical application as referred to herein can refer to application onto one or more surface, e.g., keratinous tissue. Topical application may relate to direct application to the desired area. A topical cosmetic or pharmaceutical composition or preparation can be applied by, e.g., pouring, dropping, or spraying, when present as a liquid or aerosol composition; smoothing, rubbing, spreading, and the like, when in ointment, lotion, cream, gel, or a like composition; dusting, when a powder; or by any other appropriate means.

In some embodiments, a subject is treated with an effective amount of the topical cosmetic or pharmaceutical composition during a period between treatments with an injectable neurotoxin, e.g., onabotulinum toxin A, wherein the injectable neurotoxin treatment was intended to prevent or temporarily improve the appearance in a subject of one or more features including skin wrinkles, e.g., in the face, skin laxity, moderate to severe glabellar lines associated with corrugator and/or procerus muscle activity, moderate to severe lateral canthal lines associated with orbicularis oculi activity (crow's feet lines), and moderate to severe forehead lines associated with frontalis muscle activity. In these embodiments, treatment with the topical cosmetic or pharmaceutical composition of the invention in effect extends the period of prevention or temporary improvement of the appearance of the one or more features conferred by the onabotulinum toxin A treatment. In some embodiments a subject is treated with a topical cosmetic or pharmaceutical composition of the invention is periodically beginning on the day after, 1, 2, 3, 4, 5, 6, 7, 8, 9, 10, 11, 12, 13, 14, 15, 16, 17, 18, 19, 20, 21, 22, 23, 24, 25, or 26 weeks after a treatment with an injectable neurotoxin.

In some embodiments, the subject is treated by topical application of an effective amount of the cosmetic or pharmaceutical composition one time or more during a course of treatment, e.g., 1-3 times per day, 1-21 times per week, 1 time per day, 2 times per day, or 3 times per day. In some embodiments, a subject is treated with an effective amount of the cosmetic or pharmaceutical composition about 1 time per week to about 12 times per week. In some embodiments, a subject is treated with an effective amount of the cosmetic or pharmaceutical composition at least about 1 time per week. In some embodiments, a subject is treated with an effective amount of the cosmetic or pharmaceutical composition at most about 12 times per week. In some embodiments, a subject is treated with an effective amount of the cosmetic or pharmaceutical composition about 1 time per week to about 2 times per week, about 1 time per week to about 3 times per week, about 1 time per week to about 4 times per week, about 1 time per week to about 5 times per week, about 1 time per week to about 6 times per week, about 1 time per week to about 7 times per week, about 1 time per week to about 8 times per week, about 1 time per week to about 9 times per week, about 1 time per week to about 10 times per week, about 1 time per week to about 11 times per week, about 1 time per week to about 12 times per week, about 2 times per week to about 3 times per week, about 2 times per week to about 4 times per week, about 2 times per week to about 5 times per week, about 2 times per week to about 6 times per week, about 2 times per week to about 7 times per week, about 2 times per week to about 8 times per week, about 2 times per week to about 9 times per week, about 2 times per week to about 10 times per week, about 2 times per week to about 11 times per week, about 2 times per week to about 12 times per week, about 3 times per week to about 4 times per week, about 3 times per week to about 5 times per week, about 3 times per week to about 6 times per week, about 3 times per week to about 7 times per week, about 3 times per week to about 8 times per week, about 3 times per week to about 9 times per week, about 3 times per week to about 10 times per week, about 3 times per week to about 11 times per week, about 3 times per week to about 12 times per week, about 4 times per week to about 5 times per week, about 4 times per week to about 6 times per week, about 4 times per week to about 7 times per week, about 4 times per week to about 8 times per week, about 4 times per week to about 9 times per week, about 4 times per week to about 10 times per week, about 4 times per week to about 11 times per week, about 4 times per week to about 12 times per week, about 5 times per week to about 6 times per week, about 5 times per week to about 7 times per week, about 5 times per week to about 8 times per week, about 5 times per week to about 9 times per week, about 5 times per week to about 10 times per week, about 5 times per week to about 11 times per week, about 5 times per week to about 12 times per week, about 6 times per week to about 7 times per week, about 6 times per week to about 8 times per week, about 6 times per week to about 9 times per week, about 6 times per week to about 10 times per week, about 6 times per week to about 11 times per week, about 6 times per week to about 12 times per week, about 7 times per week to about 8 times per week, about 7 times per week to about 9 times per week, about 7 times per week to about 10 times per week, about 7 times per week to about 11 times per week, about 7 times per week to about 12 times per week, about 8 times per week to about 9 times per week, about 8 times per week to about 10 times per week, about 8 times per week to about 11 times per week, about 8 times per week to about 12 times per week, about 9 times per week to about 10 times per week, about 9 times per week to about 11 times per week, about 9 times per week to about 12 times per week, about 10 times per week to about 11 times per week, about 10 times per week to about 12 times per week, or about 11 times per week to about 12 times per week. In some embodiments, a subject is treated with an effective amount of the cosmetic or pharmaceutical composition about 1 time per week, about 2 times per week, about 3 times per week, about 4 times per week, about 5 times per week, about 6 times per week, about 7 times per week, about 8 times per week, about 9 times per week, about 10 times per week, about 11 times per week, about 12 times per week, about 13 times per week, or about 14 times per week.

In some embodiments, a pharmaceutical composition of the invention is administered to a subject, for indications including but not limited to: prevention or temporary improvement of the appearance of one or more of skin wrinkles, e.g., in the face, skin laxity, moderate to severe glabellar lines associated with corrugator and/or procerus muscle activity, moderate to severe lateral canthal lines associated with orbicularis oculi activity (crow's feet lines), and moderate to severe forehead lines associated with frontalis muscle activity; treatment of overactive bladder (OAB); treatment of urinary incontinence; prophylaxis of headaches; treatment of spasticity; treatment of cervical dystonia; treatment of hypersalivation (also called ptyalism or sialorrhea); treatment of blepharospasm associated with dystonia; and treatment of strabismus. Administration of a composition of the invention can be carried out as appropriate for the specific treatment, e.g., by local injection. In some embodiments, a composition of the invention is administered by, e.g., intradermal, intradetrusor, or subcutaneous injection.

In some embodiments, a topical cosmetic composition of the invention is self-applied or administered by a patient. In some embodiments, a cosmetic or pharmaceutical composition of the invention is applied or administered by a medical professional, e.g., in a medical office setting.

Summary Paragraphs

1. A muscle-type nicotinic acetylcholine receptor peptide antagonist comprising an amino acid sequence:
Xaa1-Xaa2-Xaa3-Xaa4-Xaa5-Xaa6-Xaa7-Xaa8-Xaa9-Xaa10-Xaa11-Xaa12-Xaa13-Xaa14 wherein:
Xaa1 is absent or selected from Ala, Gly, Val, Leu, Ile and a derivative of Ala, Gly, Val, Leu, or Ile;
Xaa2 is absent or selected from: Asn, Asp, Gln, Glu, Arg, His, Lys, Phe, Trp, Tyr, Ala, Gly, Val, Leu, Ile, and a derivative of Asn, Asp, Gln, Glu, Arg, His, Lys, Phe, Trp, Tyr, Ala, Gly, Val, Leu, or Ile;
Xaa3 and Xaa8 form a linkage Xaa3-Xaa8;
Xaa4 and Xaa14 form a linkage Xaa4-Xaa14;
Xaa5 is selected from: Asn, Asp, Gln, Glu, Arg, His, Lys, and a derivative of Asn, Asp, Gln, Glu, Arg, His, or Lys;
Xaa6 is selected from: Pro and a derivative thereof;
Xaa7 is selected from: Ala, Gly, Val, Leu, Ile and a derivative of Ala, Gly, Val, Leu, or Ile;
Xaa9 is selected from: Ala, Gly, Val, Leu, Ile and a derivative of Ala, Gly, Val, Leu, or Ile;
Xaa10 is selected from: Arg, His, Lys, and a derivative of Arg, His, or Lys;
Xaa11 is selected from: Asn, Asp, Gln, Glu, Arg, His, Lys, and a derivative of Asn, Asp, Gln, Glu, Arg, His, or Lys;
Xaa12 is selected from: Phe, Trp, Tyr, and a derivative of Phe, Trp, or Tyr;
Xaa13 is selected from: Cys, Met, Sec, Ser, Thr, Arg, His, Lys, and a derivative of Cys, Met, Sec, Ser, Thr, Arg, His, or Lys;
the N-terminus is optionally modified; and
the C-terminus is optionally modified.

2. The muscle-type nicotinic acetylcholine receptor peptide antagonist of paragraph 1, wherein:
Xaa1 is absent;
Xaa2 is absent;
the Xaa3-Xaa8 linkage is selected from: a Cys-Cys linkage, a Sec-Sec linkage, a cystathionine linkage, a lactam bridge, a thioether linkage, and a dicarba linkage;
the Xaa4-Xaa14 linkage is selected from: a Cys-Cys linkage, a Sec-Sec linkage, a cystathionine linkage, a lactam bridge, a thioether linkage, and a dicarba linkage;
Xaa5 is selected from: Asn, Asp, Gln, Glu, and a derivative of Asn, Asp, Gln, or Glu;
Xaa6 is selected from: Pro and a derivative thereof;
Xaa7 is selected from: Ala, Gly, Val, Leu, Ile and a derivative of Ala, Gly, Val, Leu, or Ile;
Xaa9 is selected from: Ala, Gly, Val, Leu, Ile and a derivative of Ala, Gly, Val, Leu, or Ile;
Xaa10 is selected from: Arg, His, Lys, and a derivative of Arg, His, or Lys;
Xaa11 is selected from: Arg, His, Lys, and a derivative of Arg, His, or Lys;
Xaa12 is selected from: Phe, Trp, Tyr, and a derivative of Phe, Trp, or Tyr; and
Xaa13 is selected from: Cys, Met, Sec, Ser, Thr, and a derivative of Cys, Met, Sec, Ser, or Thr.

3. The muscle-type nicotinic acetylcholine receptor peptide antagonist of paragraph 1, wherein:
Xaa1 is absent;
Xaa2 is absent;
the Xaa3-Xaa8 linkage is selected from: a Cys-Cys linkage, a Sec-Sec linkage, a cystathionine linkage, a lactam bridge, a thioether linkage, and a dicarba linkage;
the Xaa4-Xaa14 linkage is selected from: a Cys-Cys linkage, a Sec-Sec linkage, a cystathionine linkage, a lactam bridge, a thioether linkage, and a dicarba linkage;

Xaa5 is selected from: Arg, His, Lys, and a derivative of Arg, His, or Lys;
Xaa6 is selected from: Pro and a derivative thereof;
Xaa7 is selected from: Ala, Gly, Val, Leu, Ile and a derivative of Ala, Gly, Val, Leu, or Ile;
Xaa9 is selected from: Ala, Gly, Val, Leu, Ile and a derivative of Ala, Gly, Val, Leu, or Ile;
Xaa10 is selected from: Arg, His, Lys, and a derivative of Arg, His, or Lys;
Xaa11 is selected from: Asn, Asp, Gln, Glu, and a derivative of Asn, Asp, Gln, or Glu;
Xaa12 is selected from: Phe, Trp, Tyr, and a derivative of Phe, Trp, or Tyr; and
Xaa13 is selected from: Cys, Met, Sec, Ser, Thr, and a derivative of Cys, Met, Sec, Ser, or Thr.

4. The muscle-type nicotinic acetylcholine receptor peptide antagonist of paragraph 1, wherein:
Xaa1 is absent;
Xaa2 is selected from: Arg, His, Lys, and a derivative of Arg, His, or Lys;
the Xaa3-Xaa8 linkage is selected from: a Cys-Cys linkage, a Sec-Sec linkage, a cystathionine linkage, a lactam bridge, a thioether linkage, and a dicarba linkage;
the Xaa4-Xaa14 linkage is selected from: a Cys-Cys linkage, a Sec-Sec linkage, a cystathionine linkage, a lactam bridge, a thioether linkage, and a dicarba linkage;
Xaa5 is selected from: Arg, His, Lys, and a derivative of Arg, His, or Lys;
Xaa6 is selected from: Pro and a derivative thereof;
Xaa7 is selected from: Ala, Gly, Val, Leu, Ile and a derivative of Ala, Gly, Val, Leu, or Ile;
Xaa9 is selected from: Ala, Gly, Val, Leu, Ile and a derivative of Ala, Gly, Val, Leu, or Ile;
Xaa10 is selected from: Arg, His, Lys, and a derivative of Arg, His, or Lys;
Xaa11 is selected from: Asn, Asp, Gln, Glu, and a derivative of Asn, Asp, Gln, or Glu;
Xaa12 is selected from: Phe, Trp, Tyr, and a derivative of Phe, Trp, or Tyr; and
Xaa13 is selected from: Cys, Met, Sec, Ser, Thr, and a derivative of Cys, Met, Sec, Ser, or Thr.

5. The muscle-type nicotinic acetylcholine receptor peptide antagonist of paragraph 1, wherein:
Xaa1 is absent;
Xaa2 is absent;
the Xaa3-Xaa8 linkage is selected from: a Cys-Cys linkage, a Sec-Sec linkage, a cystathionine linkage, a lactam bridge, a thioether linkage, and a dicarba linkage;
the Xaa4-Xaa14 linkage is selected from: a Cys-Cys linkage, a Sec-Sec linkage, a cystathionine linkage, a lactam bridge, a thioether linkage, and a dicarba linkage;
Xaa5 is selected from: Arg, His, Lys, and a derivative of Arg, His, or Lys;
Xaa6 is selected from: Pro and a derivative thereof;
Xaa7 is selected from: Ala, Gly, Val, Leu, Ile and a derivative of Ala, Gly, Val, Leu, or Ile;
Xaa9 is selected from: Ala, Gly, Val, Leu, Ile and a derivative of Ala, Gly, Val, Leu, or Ile;
Xaa10 is selected from: Arg, His, Lys, and a derivative of Arg, His, or Lys;
Xaa11 is selected from: Arg, His, Lys, and a derivative of Arg, His, or Lys;
Xaa12 is selected from: Phe, Trp, Tyr, and a derivative of Phe, Trp, or Tyr; and
Xaa13 is selected from: Cys, Met, Sec, Ser, Thr, and a derivative of Cys, Met, Sec, Ser, or Thr.

6. The muscle-type nicotinic acetylcholine receptor peptide antagonist of any of paragraphs 1-5, wherein:
Xaa1 is absent or selected from Ala, Gly, Val, Leu, Ile and a derivative of Ala, Gly, Val, Leu, or Ile;
Xaa2 is absent or selected from: Asn, Asp, Gln, Arg, His, Lys, Phe, Trp, Tyr, Ala, Gly, Val, Leu, Ile, and a derivative of Asn, Asp, Gln, Arg, His, Lys, Phe, Trp, Tyr, Ala, Gly, Val, Leu, or Ile;
the Xaa3-Xaa8 linkage is selected from: a Sec-Sec linkage, a cystathionine linkage, a lactam bridge, a thioether linkage, and a dicarba linkage;
the Xaa4-Xaa14 linkage is selected from: a Sec-Sec linkage, a cystathionine linkage, a lactam bridge, a thioether linkage, and a dicarba linkage;
Xaa5 is selected from: Asp, Gln, Glu, Arg, His, Lys, and a derivative of Asp, Gln, Glu, Arg, His, or Lys;
Xaa6 is selected from: Pro and a derivative thereof;
Xaa7 is selected from: Gly, Val, Leu, Ile and a derivative of Gly, Val, Leu, or Ile;
Xaa9 is selected from: Ala, Val, Leu, Ile and a derivative of Ala, Val, Leu, or Ile;
Xaa10 is selected from: His, Lys, and a derivative of His or Lys;
Xaa11 is selected from: Asn, Asp, Gln, Glu, Arg, Lys, and a derivative of Asn, Asp, Gln, Glu, Arg, or Lys;
Xaa12 is selected from: Phe, Trp, Tyr, and a derivative of Phe or Trp; and
Xaa13 is selected from: Cys, Met, Sec, Thr, Arg, His, Lys, and a derivative of Cys, Met, Sec, Thr, Arg, His, or Lys.

7. The muscle-type nicotinic acetylcholine receptor peptide antagonist of any of paragraphs 1-5, wherein:
Xaa1 is absent or selected from Ala, Gly, Val, Leu, Ile and a derivative of Ala, Gly, Val, Leu, or Ile;
Xaa2 is absent or selected from: Asn, Asp, Gln, Arg, His, Lys, Phe, Trp, Tyr, Ala, Gly, Val, Leu, Ile, and a derivative of Asn, Asp, Gln, Arg, His, Lys, Phe, Trp, Tyr, Ala, Gly, Val, Leu, or Ile;
the Xaa3-Xaa8 linkage is selected from: a Sec-Sec linkage, a cystathionine linkage, a lactam bridge, a thioether linkage, and a dicarba linkage;
the Xaa4-Xaa14 linkage is selected from: a Sec-Sec linkage, a cystathionine linkage, a lactam bridge, a thioether linkage, and a dicarba linkage;
Xaa5 is selected from: Asp, Gln, Glu, Arg, Lys, and a derivative of Asp, Gln, Glu, Arg, or Lys;
Xaa6 is selected from: Pro and a derivative thereof;
Xaa7 is selected from: Gly, Val, Leu, Ile and a derivative of Gly, Val, Leu, or Ile;
Xaa9 is selected from: Ala, Val, Leu, Ile and a derivative of Ala, Val, Leu, or Ile;
Xaa10 is selected from: Arg, His, and a derivative of Arg or Lys;
Xaa11 is selected from: Asn, Asp, Gln, Glu, Arg, Lys, and a derivative of Asn, Asp, Gln, Glu, Arg, or Lys;
Xaa12 is selected from: Trp, Tyr, and a derivative of Trp or Tyr; and
Xaa13 is selected from: Cys, Met, Sec, Thr, Arg, His, Lys, and a derivative of Cys, Met, Sec, Thr, Arg, His, or Lys.

8. The muscle-type nicotinic acetylcholine receptor peptide antagonist of any of paragraphs 1-5, wherein:
Xaa1 is absent or selected from Ala, Val, Leu, Ile and a derivative of Ala, Val, Leu, or Ile;
Xaa2 is absent or selected from: Asn, Asp, Gln, Glu, His, Lys, Phe, Trp, Tyr, Ala, Gly, Val, Leu, Ile, and a derivative of Asn, Asp, Gln, Glu, His, Lys, Phe, Trp, Tyr, Ala, Gly, Val, Leu, or Ile;

the Xaa3-Xaa8 linkage is selected from: a Sec-Sec linkage, a cystathionine linkage, a lactam bridge, a thioether linkage, and a dicarba linkage;

the Xaa4-Xaa14 linkage is selected from: a Sec-Sec linkage, a cystathionine linkage, a lactam bridge, a thioether linkage, and a dicarba linkage;

Xaa5 is selected from: Asn, Asp, Gln, Glu, Arg, Lys, and a derivative of Asn, Asp, Gln, Glu, Arg, or Lys;

Xaa6 is selected from: Pro and a derivative thereof;

Xaa7 is selected from: Gly, Val, Leu, Ile and a derivative of Gly, Val, Leu, or Ile;

Xaa9 is selected from: Ala, Val, Leu, Ile and a derivative of Ala, Val, Leu, or Ile;

Xaa10 is selected from: Arg, His, and a derivative of Arg or His;

Xaa11 is selected from: Asp, Gln, Glu, Arg, His, Lys, and a derivative of Asp, Gln, Glu, Arg, His, or Lys;

Xaa12 is selected from: Phe, Trp, and a derivative of Phe or Trp; and

Xaa13 is selected from: Cys, Met, Sec, Thr, Arg, His, Lys, and a derivative of Cys, Met, Sec, Thr, Arg, His, or Lys.

9. The muscle-type nicotinic acetylcholine receptor peptide antagonist of paragraph 1, wherein the Xaa3-Xaa8 linkage and the Xaa4-Xaa14 linkage are independently selected from:

a Cys-Cys linkage;
(ii) a Sec-Sec linkage;
(iii) a cystathionine linkage;
(iv) a lactam bridge,
(v) a thioether linkage, and
(vi) a dicarba linkage.

10. The muscle-type nicotinic acetylcholine receptor peptide antagonist of paragraph 9, wherein the thioether linkage is a lanthionine linkage.

11. The muscle-type nicotinic acetylcholine receptor peptide antagonist of any one of paragraphs 1-10, wherein the linkage between Xaa3 and Xaa8 has a spatial separation between the alpha carbons or the geometric centers of each of Xaa3 and Xaa8 of about 3.5 to about 10 angstroms, wherein the linkage between Xaa4 and Xaa14 has a spatial separation between the alpha carbons or the geometric centers of each of Xaa4 and Xaa14 of about 3.5 to about 10 angstroms, or both.

12. The muscle-type nicotinic acetylcholine receptor peptide antagonist of any one of paragraphs 1-11, wherein the N-terminus is modified to comprise C1-C6 acyl, C1-C8 alkyl, C6-C12 aralkyl, C5-C10 aryl, C4-C8 heteroaryl, formyl, or a lipid.

13. The muscle-type nicotinic acetylcholine receptor peptide antagonist of any one of paragraphs 1-12, wherein the N-terminus is not modified with an amino acid or a derivative of an amino acid.

14. The muscle-type nicotinic acetylcholine receptor peptide antagonist of any one of paragraphs 1-13, wherein the C-terminus is modified to comprise NH2, amino-acyl, amino-C1-C8 alkyl, amino-C6-C12-aralkyl, amino-C5-C10 aryl, amino-C4-C8 heteroaryl, or O—(C1-C8 alkyl).

15. The muscle-type nicotinic acetylcholine receptor macrocyclic peptide antagonist of any one of paragraphs 1-14, wherein the C-terminus is not modified with an amino acid or a derivative of an amino acid.

16. The muscle-type nicotinic acetylcholine receptor peptide antagonist of any one of paragraphs 1-15, wherein a lipid is covalently attached to a cysteine, serine, lysine, threonine or tyrosine.

17. The muscle-type nicotinic acetylcholine receptor peptide antagonist of paragraph 16, wherein the lipid is covalently attached to a cysteine or a lysine.

18. The muscle-type nicotinic acetylcholine receptor peptide antagonist of any one of paragraphs 1-17, wherein the lipid comprises a C6-C20 alkyl, C6-C20 alkenyl, C6-C20 alkynyl, or C6-C20 acyl group.

19. The muscle-type nicotinic acetylcholine receptor peptide antagonist of any one of paragraphs 1-17, wherein the lipid comprises a geranyl, farnesyl, or geranylgeranyl group.

20. The muscle-type nicotinic acetylcholine receptor peptide antagonist of any one of paragraphs 1-17, wherein the lipid comprises a undecyloyl, lauroyl, tridecyloyl, myristoyl, palmitoyl, or stearoyl group.

21. The muscle-type nicotinic acetylcholine receptor peptide antagonist of any one of paragraphs 1-17, wherein the lipid is a covalent modification of Cys added by palmitoylation or prenylation.

22. The muscle-type nicotinic acetylcholine receptor peptide antagonist of any one of paragraphs 1-21, comprising at least one derivative that is a non-canonical amino acid selected from the group consisting of: an aromatic side chain amino acid; a non-aromatic side chain amino acid; an aliphatic side chain amino acid; a side chain amide amino acid; a side chain ester amino acid; a heteroaromatic side chain amino acid; a side chain thiol amino acid; a beta amino acid; and a backbone-modified amino acid.

23. The muscle-type nicotinic acetylcholine receptor peptide antagonist of paragraph 22, wherein the aromatic side chain amino acid is a derivative of tyrosine, histidine, tryptophan, or phenylalanine.

24. The muscle-type nicotinic acetylcholine receptor peptide antagonist of paragraph 22, wherein the non-aromatic side chain amino acid is a derivative of serine, threonine, cysteine, methionine, arginine, asparagine, glutamine, aspartic acid, glutamic acid, lysine, proline, glycine, alanine, valine, isoleucine, or leucine.

25. The muscle-type nicotinic acetylcholine receptor peptide antagonist of any one of paragraphs 1-22, comprising a derivative that is a non-canonical amino acid selected from the group consisting of: 2-aminoadipic acid; 3-aminoadipic acid; beta-alanine; beta-aminoproprionic acid; 2-aminobutyric acid; 4-aminobutyric acid; piperidinic acid; 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminoproprionic acid; N-ethylglycine; N-ethylasparagine; hydroxylysine; allo-hydroxylysine; 3-hydroxyproline; 4-hydroxyproline; isodesmosine; allo-isoleucine; N-methylglycine; sarcosine; n-methylisoleucine; 6-N-methyllysine; N-methylvaline; norvaline; norleucine; and ornithine.

26. The muscle-type nicotinic acetylcholine receptor peptide antagonist of any of paragraphs 1-25, wherein one or more amino acids in the peptide have the D-amino acid configuration and the remaining amino acids in the peptide have the L-amino acid configuration.

27. The muscle-type nicotinic acetylcholine receptor peptide antagonist of any of paragraphs 1-26, wherein the antagonist selectively inhibits a muscle-type nicotinic acetylcholine receptor.

28. The muscle-type nicotinic acetylcholine receptor peptide antagonist of paragraph 27, wherein the $IC_{50}$ is about 1 millimolar to about 1 picomolar.

29. The muscle-type nicotinic acetylcholine receptor peptide antagonist of paragraph 28, wherein the $IC_{50}$ is determined by an activity assay.

30. The muscle-type nicotinic acetylcholine receptor peptide antagonist of paragraph 29, wherein the activity assay is a competitive binding assay or an assay of inhibition of the acetylcholine receptor ion channel conductance.

31. A cosmetic composition comprising the muscle-type nicotinic acetylcholine receptor peptide antagonist of any of paragraphs 1-30 and 55, for prevention or temporary improvement of the appearance of one or more of skin wrinkles, skin laxity, moderate to severe glabellar lines associated with corrugator and/or procerus muscle activity, moderate to severe lateral canthal lines associated with orbicularis oculi activity, and moderate to severe forehead lines associated with frontalis muscle activity, in a subject.

32. The cosmetic composition of paragraph 31, formulated for topical use.

33. The cosmetic composition of paragraph 32, comprising one or more excipient selected from the group consisting of: water, a buffer, an absorption enhancer, a stability enhancer, diaminobutyroyl benzylamide, diacetate, glycerin, a gum, a hydrophilic colloid or derivative, a cellulosic derivative, an emulsifier, a fatty alcohol, an acrylic derivative, a mineral, a surfactant, a fat, an oil, a preservative, a monosaccharide, a disaccharide, a polysaccharide, a glycosaminoglycan, and a chelating agent.

34. The cosmetic composition of paragraph 33, wherein the absorption enhancer is selected from the group consisting of: a liposome delivery system, a transfersome delivery system, an ethosome delivery system, a short chain alcohol, a long chain alcohol, a polyalcohol, urea, an amino acid, an amino acid ester, an amine, an amide, 1-dodecylazacycloheptan-2-one (AZONE®), a derivative of 1-dodecylazacycloheptan-2-one, a pyrrolidone, a pyrrolidone derivative, a terpene, a terpene derivative, a fatty acid, a fatty acid ester, a macrocyclic compound, a tenside, a sulfoxide, lecithin vesicles, water surfactants, a polyol, a small molecule tri, tetra, penta, hexa, septa or octa peptide, isoceteth-20, ethoxydiglycol, dimethyl sulfoxide, dimethyl isosorbide, and phloretin.

35. The cosmetic composition of paragraph 34, wherein the stability enhancer is a small molecule peptide.

36. The cosmetic composition of paragraph 35 wherein the small molecule peptide is selected from the group consisting of: a tripeptide, a tetrapeptide, a pentapeptide, a hexapeptide, a septapeptide, an octapeptide, Acetyl Hexapeptide-3 Cosmetic Topical Peptide, Melanotan II, ACVR2B (ACE-031), Argireline® Acetate, Argireline, Matrixyl Acetate (palmitoyl pentapeptide), peptide GHK spontaneously complexes with copper, Palmitoyl Tetrapeptide-3, Argireline, Acetyl Glutamyl Heptapeptide, Matrixyl™, Snap-8, Syn®-Tacks, Syn®-Coll, Syn®-Hycan, Leuphasyl®, Pepha®-Tight, Tego® Pep 4-17 and Trylagen®.

37. The cosmetic composition of any of paragraphs 31-36, further comprising one or more other active ingredient.

38. The cosmetic composition of paragraph 37, wherein the one or more other active ingredient is selected from the group consisting of: a second, different, muscle-type nicotinic acetylcholine receptor peptide antagonist, an antioxidant, a retinoid, a growth factor, a collagen stimulating peptide, a carrier peptide, a peptide that inhibits tTAT-superoxide dismutase, a peptide that inhibits a proteinase, a peptide that stimulates hyaluronan synthase 2, and a keratin-based peptide.

39. The cosmetic composition of any of paragraphs 31-37, comprising a liposome delivery system.

40. The cosmetic composition of any of paragraphs 31-39, wherein the cosmetic composition is a cream, balm, gel, solution, serum, cosmetic, liquid, lotion, ointment, emulsion, milk, spray, mask, or the like.

41. The cosmetic composition of any of paragraphs 31-39, comprising about 0.01% to about 5% w/w of the muscle-type nicotinic acetylcholine receptor peptide antagonist.

42. A pharmaceutical composition comprising the muscle-type nicotinic acetylcholine receptor peptide antagonist of any of paragraphs 1-30 and 55, for: prevention or temporary improvement of the appearance of one or more of skin wrinkles, skin laxity, moderate to severe glabellar lines associated with corrugator and/or procerus muscle activity, moderate to severe lateral canthal lines associated with orbicularis oculi activity, and moderate to severe forehead lines associated with frontalis muscle activity; treatment of overactive bladder (OAB); treatment of urinary incontinence; prophylaxis of headaches; treatment of spasticity; treatment of cervical dystonia; treatment of hypersalivation; treatment of blepharospasm associated with dystonia; or treatment of strabismus, in a subject.

43. The pharmaceutical composition of paragraph 42, formulated for intradermal, subcutaneous, intramuscular, or intradetrusor administration.

44. The pharmaceutical composition of paragraph 43, comprising one or more excipient.

45. A method for preventing or temporarily improving the appearance in a subject for prevention or temporary improvement of the appearance of one or more of skin wrinkles, skin laxity, moderate to severe glabellar lines associated with corrugator and/or procerus muscle activity, moderate to severe lateral canthal lines associated with orbicularis oculi activity, and moderate to severe forehead lines associated with frontalis muscle activity, comprising applying an effective amount of the cosmetic composition of any of paragraphs 31-40 to the skin of the subject.

46. The method of paragraph 45, wherein the muscle-type nicotinic acetylcholine receptor peptide antagonist is applied in one or more doses of the cosmetic composition.

47. The method of paragraph 46, wherein a single dose of the cosmetic composition is applied about once per hour to about once per 2 weeks.

48. The method of paragraph 47, wherein a single dose of the cosmetic composition is applied about once per day.

49. The method of any of paragraphs 45-48, wherein the cosmetic composition can be applied indefinitely with no adverse effect.

50. The method of any of paragraphs 45-49, wherein the dose of the cosmetic composition is a subimmunological dose.

51. A method for: preventing or temporarily improving one or more of the appearance of skin wrinkles, skin laxity, moderate to severe glabellar lines associated with corrugator and/or procerus muscle activity, moderate to severe lateral canthal lines associated with orbicularis oculi activity, and moderate to severe forehead lines associated with frontalis muscle activity; treatment of overactive bladder (OAB); treatment of urinary incontinence; prophylaxis of headaches; treatment of spasticity; treatment of cervical dystonia; treatment of hypersalivation; treatment of blepharospasm associated with dystonia; or treatment of strabismus; in a subject, comprising administering an effective amount of the pharmaceutical composition of any of paragraphs 42-44 to the subject.

52. The method of paragraph 51, wherein the muscle-type nicotinic acetylcholine receptor peptide antagonist is administered in one or more treatments with the pharmaceutical composition.

53. The method of paragraph 52, wherein administration of each treatment comprises injection of the pharmaceutical composition by injection into one or more treatment sites.

54. The method of any of paragraphs 51-53, wherein each treatment comprises a subimmunological dose of the pharmaceutical composition.

55. A muscle-type nicotinic acetylcholine receptor peptide antagonist comprising an amino acid sequence set forth as any of SEQ ID NOS: 4-52 and 60-79.

56. The muscle-type nicotinic acetylcholine receptor peptide antagonist of paragraph 55, comprising an amino acid sequence set forth as any of SEQ ID NOS: 60, 61, 62, 73, and 78.

EXAMPLES

Example 1. Evaluation of Muscle-Type nAChR Peptide Antagonist Binding to nAChR (alpha1) Human Ion Channel Using Antagonist Radioligand Competition Assay The binding of a muscle-type nAChR peptide antagonist of the invention to the alpha 1 subunit of nAChR is evaluated in a competition assay. Human rhabdomyosarcoma cells are used to prepare nicotinic acetylcholine bungarotoxin-sensitive muscle membranes in Ringer's solution pH 7.4. For acetylcholine-site competition binding assays, suspensions of nAChR-rich membranes (240 mg/mL) are incubated with 0.6 nM [$^{125}$I] of alpha-Bungarotoxin for 1 hour at 25° C. The membrane suspensions are applied to glass GF/F filters (Whatman, Maidstone, UK) presoaked in 0.25% polyethylenimine, and the unbound radioactivity is removed from the filter by washes (3×3 mL) with 50 mm Tris/HCl buffer, pH 8.0. The filters are washed and counted to measure specifically bound [$^{125}$I] alpha-Bungarotoxin. Inhibition curves are obtained by determining the reduction of bound alpha-Bungarotoxin in the presence of an amount of, and/or by increasing amounts of, the peptide antagonist of the invention. Non-specific binding of peptide is estimated separately in the presence of a vast excess (1 mM) of alpha-Bungarotoxin, which occupies all the available acetylcholine sites.

Using this assay, the binding of a peptide antagonist of the invention to the alpha 1 subunit of nAChR is compared to a control peptide, e.g., a peptide having the amino acid sequence set forth as SEQ ID NO: 53, or a peptide having a sequence set forth as any one of SEQ ID NOS: 1-3 and 53-59.

Example 2. Evaluation of Muscle-Type nAChR Peptide Antagonist Effect on Ion Channel Activity Using nAChR (alpha1/beta1/delta/epsilon) Human Ion Channel Cell-Based Antagonist IonFlux Assay: Comparison with CGI The Fluxion Bioscience IonFlux HT (Molecular Devices) Automated Patch Clamp microfluidic design was used to make ion channel recordings (Eurofins)Cells expressing human nAChR (Millipore PrecisION™ hnAChR α/β1/γ/ε-HEK 293 Recombinant Cell Line, Cat #CYL3052) were cultured in medium containing DMEM/F12 glutamax, Fetal Bovine Serum, Non Essential AA, Geneticin, and Hygromycin B at 37° C. and 5% CO2. For cell isolation, flasks were first washed with 10 ml of Ca- and Mg-free PBS, followed by 2 ml of Detachin™ solution (Genlantis), after which cells were treated with Detachin™ solution. After release, the cell suspension was spun for 90 seconds (1000 rpm) and re-suspended in extracellular solution ($5\times10^6$ cell/ml). The extracellular solution contained (mM): 138 NaCl, 4 KCl, 1 MgCl2, 1.8 CaCl2, 10 HEPES, 5.6 glucose, pH 7.45 with NaOH. The intracellular solution for the whole cell voltage clamp contained (mM): 15 NaCl, 60 KCl, 70 KF, 5 HEPES, 5 EGTA, pH 7.25 with KOH. Cell suspension in extracellular solution was dispensed into an IonFlux plate. The IonFlux plate layout consisted of units of twelve wells; two wells containing intracellular solution, one containing ECS plus cells, eight containing ECS plus compounds of interest, and one well for waste collection. Cells were captured from suspension by applying suction to microscopic channels in ensemble recording arrays. Once the array was fully occupied, the applied suction broke the cell membranes of captured cells, establishing whole cell voltage clamp. For compound applications, pressure was applied to the appropriate compound wells, introducing the compound into the extracellular solution rapidly flowing over the cells. For recording nAChR currents, cell arrays were voltage clamped at a holding potential of −80 mV. Acetylcholine, the nAChR agonist (Sigma-Aldrich Cat #A6625). ACh was dissolved in deionized water to make a 10 mM stock solution, and diluted serially into extracellular buffer. Data analysis and graphical presentation were carried out using a combination of IonFlux software and Origin Lab. A threshold was set at −2 nA for responses to 10 uM ACh. Ensemble responses below this value were excluded from the analysis.

Using this assay, the effect of representative peptide antagonists set forth in Table 1 were compared to that of a positive control peptide having the amino acid sequence set forth as SEQ ID NO: 1 (Conotoxin GI, also referred to as CGI). Peptides were synthesized by AnaSpec (Fremont, Calif.). Based on the percent conduction inhibition relative to the agonist the $IC_{50}$ values were determined (Eurofins or AAT Bioquest $IC_{50}$ calculator). The $IC_{50}$ values for the control and test peptides are shown in Table 3.

TABLE 3

| Effect on Ion Channel Activity of Peptide Antagonists | |
|---|---|
| $IC_{50}$ less than 200 nM | $IC_{50}$ greater than 200 nM |
| SEQ ID NO: 61 | SEQ ID NO: 1 |
| SEQ ID NO: 78 | SEQ ID NO: 60 |
| SEQ ID NO: 73 | SEQ ID NO: 62 |

Example 3. Evaluation of Human Skin Penetration by Peptide Antagonists Using Dynamic Flux Assay A peptide antagonist of the invention is tested for skin permeation and penetration in vitro in a dynamic flux assay with Franz diffusion cells. Experiments were performed using human epidermal membranes and Silastic® membranes. The Franz diffusion cells are made of glass with a contact area of 1.35 cm, pretreated with a silanizing agent (Sigmacoat®). The Franz diffusion cell consists of a donor compartment and a receptor compartment. The membrane is mounted between the cell compartments and an O-ring is used to position the membrane. The two cell compartments are held together with a clamp. The receptor compartment has a volume of 4.3 ml and is filled with PBS-buffer. It is kept at 37° C. by circulating water through an external water jacket. After 30 min of equilibration of the membrane with the receptor solution, 200 μl of the test peptide antagonist solution is applied in the donor compartment by means of a pipet. The donor compartment is then covered with parafilm to prevent evaporation of the solvent. The receptor solution is continuously stirred by means of a spinning bar magnet at 400 rpm. Receptor solution samples, 2.0 ml aliquots, are withdrawn through the sampling port of the receptor compartment at various time intervals. Presence of the test peptide antagonist is assessed by mass spectrometry. The cells are refilled with receptor solution to keep the volume of receptor solution constant during the experiment. The experiments are run for 25 hours. Penetration of skin from at least three different donors is carried out in triplicate.

Using this assay, the skin penetration of a peptide antagonist of the invention is compared to that of a peptide having the amino acid sequence set forth as SEQ ID NO: 53, or a peptide having a sequence set forth as any one of SEQ ID NOS: 1-3 and 53-59.

Example 4. Evaluation of the Safety and Efficacy of a Muscle-Type nAChR Peptide Antagonist Compared to Placebo for Treatment of Facial Wrinkles A muscle-type nAChR peptide antagonist of the invention is tested for safety and efficacy compared with placebo in the treatment of facial rhytides (skin wrinkles) and glabellar frown lines in a randomized, double-blind human clinical trial. Patients (50 in each group) are treated with an amount of the muscle-type nAChR peptide antagonist, or placebo (saline) injected into bilateral forehead and frown line areas on Day 1.

Primary outcome: Percentage of Participants Achieving a Score of None or Mild by Investigator-Assessment of Facial Wrinkle Scale With Photonumeric Guide (FWS) in Forehead Lines at Maximum Eyebrow Elevation.

On Day 30, the severity of the patient's forehead lines at maximum eyebrow elevation using the 4-point Facial Wrinkle Scale with Photonumeric Guide (FWS): 0=none, 1=mild, 2=moderate or 3=severe is assessed. The percentage of participants with a score of none or mild is determined.

Primary outcome: Percentage of Participants Achieving a Score of None or Mild by Subject-Assessment of Facial Wrinkle Scale With Photonumeric Guide (FWS) in Forehead Lines at Maximum Eyebrow Elevation.

Also on Day 30, the patients assess the severity of their forehead lines at maximum eyebrow elevation using the 4-point Facial Wrinkle Scale with Photonumeric Guide (FWS): 0=none, 1=mild, 2=moderate or 3=severe and the percentage of participants with a score of none or mild is determined.

Secondary outcome: Percentage of Participants Achieving Satisfied or Very Satisfied by Subject Assessment of Satisfaction of Appearance of Forehead Lines (participant assessment).

On Day 30, participants rate their overall satisfaction with the appearance of the forehead line area using a 5-point scale: 1=very unsatisfied, 2=unsatisfied, 3=neutral, 4=satisfied or 5=very satisfied. The percentage of participants with a rating of satisfied or very satisfied is determined.

Secondary outcome: Percentage of Participants With a =1 Grade Improvement from Baseline by Investigator-Assessed FWS in Forehead Lines at Rest.

At baseline and on Day 30, the Investigator assesses the severity of the patient's forehead lines at rest using the 4-point FWS: 0=none, 1=mild, 2=moderate or 3=severe. The percentage of participants with a =1 grade improvement from baseline is determined.

Secondary outcome: Percentage of Participants With a =1 Grade Improvement from Baseline by Subject-Assessed FWS in Forehead Lines at Rest.

At baseline and on Day 30, the participant assesses the severity of their forehead lines at rest using the 4-point FWS: 0=none, 1=mild, 2=moderate or 3=severe. The percentage of participants with a =1 grade improvement from baseline is determined.

Example 5. Evaluation of Muscle-Type nAChR Peptide Antagonist Effect on Ion Channel Activity Using nAChR (alpha1/beta1/delta/epsilon) Human Ion Channel Cell-Based Antagonist IonFlux Assay: Comparison with CMI The assay described in Example 2 is further used to evaluate peptides as listed in Table 1, including the peptides tested as described in Example 2, and a positive control peptide having the amino acid sequence set forth as SEQ ID NO: 3 (Conotoxin MI, also referred to as CMI). Tested peptides having high antagonist activity based on, e.g., the calculated $IC_{50}$, are selected for further study and use in the methods and compositions as described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

TABLE 4

Table of Sequences Listed

| Protein or Nucleic Acid | Sequence | SEQ ID NO: |
|---|---|---|
| α-conotoxin GI | Glu-Cys-Cys-Asn-Pro-Ala-Cys-Gly-Arg-His-Tyr-Ser-Cys | 1 |
| α-conotoxin GII (1) | Glu-Cys-Cys-Asn-Pro-Ala-Cys-Gly-Lys-His-Phe-Ser-Cys | 2 |
| α-conotoxin MI | Gly-Arg-Cys-Cys-His-Pro-Ala-Cys-Gly-Lys-Asn-Tyr-Ser-Cys | 3 |
| Peptide Antagonist Examples | See Table 1 | 4-52, 60-79 |

TABLE 4-continued

Table of Sequences Listed

| Protein or Nucleic Acid | Sequence | SEQ ID NO: |
|---|---|---|
| From U.S. Pat. No. 9,550,808 | Trp-Tyr-Pro-Lys-Pro | 53 |
| Vialox® | Gly-Pro-Arg-Pro-Ala | 54 |
| α-bungarotoxin control peptide | Cys-Lys-Met-Trp-Ala-Asp-Ala-Phe-Thr-Ser-Ser-Arg-Gly-Lys-Val-Val-Glu-Cys-Gly | 55 |
| α-conotoxin GII (2) | Glu-Cys-Cys-His-Pro-Ala-Cys-Gly-Lys-His-Phe-Ser-Cys | 56 |
| Azemiopsin control peptide | Asp-Asn-Trp-Trp-Pro-Lys-Arg-Pro-His | 57 |
| B. multicinctus α-bungarotoxin (processed from precursor form, e.g., UniProtKB-P60615 (3L21A_BUNMU) and GenBank CAA63045.1) | Ile-Val-Cys-His-Thr-Thr-Ala-Thr-Ser-Pro-Ile-Ser-Ala-Val-Thr-Cys-Pro-Pro-Gly-Glu-Asn-Leu-Cys-Tyr-Arg-Lys-Met-Trp-Cys-Asp-Ala-Phe-Cys-Ser-Ser-Arg-Gly-Lys-Val-Val-Glu-Leu-Gly-Cys-Ala-Ala-Thr-Cys-Pro-Ser-Lys-Lys-Pro-Tyr-Glu-Glu-Val-Thr-Cys-Cys-Ser-Thr-Asp-Lys-Cys-Asn-Pro-His-Pro-Lys-Gln-Arg-Pro-Gly | 58 |
| Laticauda colubrina Lc-a (UniProtKB-P0C8R7 (3L2A_LATCO) | Arg-Ile-Cys-Tyr-Leu-Ala-Pro-Arg-Asp-Thr-Gln-Ile-Cys-Ala-Pro-Gly-Gln-Glu-Ile-Cys-Tyr-Leu-Lys-Ser-Trp-Asp-Gly-Thr-Gly-Phe-Leu-Lys-Gly-Asn-Arg-Leu-Glu-Phe-Gly-Cys-Ala-Ala-Thr-Cys-Pro-Thr-Val-Lys-Pro-Gly-Ile-Asp-Ile-Lys-Cys-Cys-Ser-Thr-Asp-Lys-Cys-Asn-Pro-His-Pro-Lys-Leu-Ala | 59 |

What is claimed is:

1. A muscle-type nicotinic acetylcholine receptor peptide antagonist comprising an amino acid sequence:

Xaa1-Xaa2-Xaa3-Xaa4-Xaa5-Xaa6-Xaa7-Xaa8-Xaa9-Xaa10-Xaa11-Xaa12-Xaa13-Xaa14 wherein:
Xaa1 is absent;
Xaa2 is absent;
Xaa3 and Xaa8 form a linkage Xaa3-Xaa8;
Xaa4 and Xaa14 form a linkage Xaa4-Xaa14;
Xaa5 is selected from: Asp, Gln, Glu, Arg, His, and Lys;
Xaa6 is selected from: Pro and hydroxyproline;
Xaa7 is selected from: Ala, Gly, Val, Leu, and Ile;
Xaa9 is selected from: Ala, Gly, Val, Leu, and Ile;
Xaa10 is selected from: Arg and His;
Xaa11 is selected from: Asn, Asp, Gln, Glu, Arg, His, and Lys;
Xaa12 is selected from: Trp and Tyr;
Xaa13 is selected from: Cys, Met, Sec, Ser, Thr, Arg, His, and Lys;
the N-terminus is optionally modified; and
the C-terminus is optionally modified.

2. The muscle-type nicotinic acetylcholine receptor peptide antagonist of claim 1, wherein:
Xaa1 is absent;
Xaa2 is absent;
the Xaa3-Xaa8 linkage is selected from: a Cys-Cys linkage, a Sec-Sec linkage, a cystathionine linkage, a lactam bridge, a thioether linkage, and a dicarba linkage;
the Xaa4-Xaa14 linkage is selected from: a Cys-Cys linkage, a Sec-Sec linkage, a cystathionine linkage, a lactam bridge, a thioether linkage, and a dicarba linkage;
Xaa5 is selected from: Asp, Gln, and Glu;
Xaa6 is selected from: Pro and hydroxyproline;
Xaa7 is selected from: Ala, Gly, Val, Leu, and Ile;
Xaa9 is selected from: Ala, Gly, Val, Leu, and Ile;
Xaa10 is selected from: Arg and His;
Xaa11 is selected from: Arg, His, and Lys;
Xaa12 is selected from: Trp and Tyr; and
Xaa13 is selected from: Cys, Met, Sec, Ser, and Thr.

3. The muscle-type nicotinic acetylcholine receptor peptide antagonist of claim 1, wherein:
Xaa1 is absent;
Xaa2 is absent;
the Xaa3-Xaa8 linkage is selected from: a Cys-Cys linkage, a Sec-Sec linkage, a cystathionine linkage, a lactam bridge, a thioether linkage, and a dicarba linkage;
the Xaa4-Xaa14 linkage is selected from: a Cys-Cys linkage, a Sec-Sec linkage, a cystathionine linkage, a lactam bridge, a thioether linkage, and a dicarba linkage;
Xaa5 is selected from: Arg, His, and Lys;
Xaa6 is selected from: Pro and hydroxyproline;
Xaa7 is selected from: Ala, Gly, Val, Leu, and Ile;
Xaa9 is selected from: Ala, Gly, Val, Leu, and Ile;
Xaa10 is selected from: Arg and His;
Xaa11 is selected from: Asn, Asp, Gln, and Glu;
Xaa12 is selected from: Trp and Tyr; and
Xaa13 is selected from: Cys, Met, Sec, Ser, and Thr.

4. The muscle-type nicotinic acetylcholine receptor peptide antagonist of claim 1, wherein:
Xaa1 is absent;
Xaa2 is absent;
the Xaa3-Xaa8 linkage is selected from: a Cys-Cys linkage, a Sec-Sec linkage, a cystathionine linkage, a lactam bridge, a thioether linkage, and a dicarba linkage;
the Xaa4-Xaa14 linkage is selected from: a Cys-Cys linkage, a Sec-Sec linkage, a cystathionine linkage, a lactam bridge, a thioether linkage, and a dicarba linkage;
Xaa5 is selected from: Arg, His, Lys;
Xaa6 is selected from: Pro;
Xaa7 is selected from: Ala, Gly, Val, Leu, and Ile;
Xaa9 is selected from: Ala, Gly, Val, Leu, and Ile;
Xaa10 is selected from: Arg and His;
Xaa11 is selected from: Arg, His, and Lys;
Xaa12 is selected from: Trp and Tyr; and
Xaa13 is selected from: Cys, Met, Sec, Ser, and Thr.

5. The muscle-type nicotinic acetylcholine receptor peptide antagonist of claim 1, wherein:
Xaa1 is absent;
Xaa2 is absent;
the Xaa3-Xaa8 linkage is selected from: a Cys-Cys linkage, a Sec-Sec linkage, a cystathionine linkage, a lactam bridge, a thioether linkage, and a dicarba linkage;
the Xaa4-Xaa14 linkage is selected from: a Cys-Cys linkage, a Sec-Sec linkage, a cystathionine linkage, a lactam bridge, a thioether linkage, and a dicarba linkage;
Xaa5 is selected from: Arg, His, and Lys;
Xaa6 is selected from: Pro and hydroxyproline;
Xaa7 is selected from: Ala, Gly, Val, Leu, and Ile;
Xaa9 is selected from: Ala, Gly, Val, Leu, and Ile;
Xaa10 is selected from: Arg and His;
Xaa11 is selected from: Arg, His, Lys, Asn, Asp, Gln, and Glu;
Xaa12 is selected from: Trp and Tyr; and
Xaa13 is selected from: Cys, Met, Sec, Ser, and Thr.

6. The muscle-type nicotinic acetylcholine receptor peptide antagonist of claim 1, wherein the Xaa3-Xaa8 linkage and the Xaa4-Xaa14 linkage are independently selected from:
(i) a Cys-Cys linkage;
(ii) a Sec-Sec linkage;
(iii) a cystathionine linkage;
(iv) a lactam bridge,
(v) a thioether linkage, and
(vi) a dicarba linkage.

7. The muscle-type nicotinic acetylcholine receptor peptide antagonist of claim 6, wherein the thioether linkage is a lanthionine linkage.

8. The muscle-type nicotinic acetylcholine receptor peptide antagonist of claim 1, wherein the N-terminus is modified to comprise $C_1$-$C_6$ acyl, $C_1$-$C_8$ alkyl, $C_6$-$C_{12}$ aralkyl, $C_5$-$C_{10}$ aryl, $C_4$-$C_8$ heteroaryl, formyl, or a lipid.

9. The muscle-type nicotinic acetylcholine receptor peptide antagonist of claim 1, wherein the C-terminus is modified to comprise $NH_2$, amino-acyl, amino-$C_1$-$C_8$ alkyl, amino-$C_6$-$C_{12}$-aralkyl, amino-$C_5$-$C_{10}$ aryl, amino-$C_4$-$C_8$ heteroaryl, or O—($C_1$-$C_8$ alkyl).

10. The muscle-type nicotinic acetylcholine receptor peptide antagonist of claim 1, wherein a lipid is covalently attached to a cysteine, serine, lysine, threonine or tyrosine.

11. The muscle-type nicotinic acetylcholine receptor peptide antagonist of claim 1, wherein the antagonist selectively inhibits a muscle-type nicotinic acetylcholine receptor.

12. The muscle-type nicotinic acetylcholine receptor peptide antagonist of claim 11, wherein the $IC_{50}$ is: about 1 millimolar to about 1 picomolar, less than about 200 nM, less than about 150 nM, or less than about 100 nM.

13. A cosmetic composition comprising the muscle-type nicotinic acetylcholine receptor peptide antagonist of claim 1, for prevention or temporary improvement of the appearance of one or more of skin wrinkles, skin laxity, moderate to severe glabellar lines associated with corrugator and/or procerus muscle activity, moderate to severe lateral canthal lines associated with orbicularis oculi activity, and moderate to severe forehead lines associated with *frontalis* muscle activity, in a subject.

14. The cosmetic composition of claim 13, formulated for topical use.

15. A pharmaceutical composition comprising the muscle-type nicotinic acetylcholine receptor peptide antagonist of claim 1, for: prevention or temporary improvement of the appearance of one or more of skin wrinkles, skin laxity, moderate to severe glabellar lines associated with corrugator and/or procerus muscle activity, moderate to severe lateral canthal lines associated with orbicularis oculi activity, and moderate to severe forehead lines associated with *frontalis* muscle activity; treatment of overactive bladder (OAB); treatment of urinary incontinence; prophylaxis of headaches; treatment of spasticity; treatment of cervical dystonia; treatment of hypersalivation; treatment of blepharospasm associated with dystonia; or treatment of strabismus, in a subject.

16. A method for preventing or temporarily improving the appearance in a subject of one or more of skin wrinkles, skin laxity, moderate to severe glabellar lines associated with corrugator and/or procerus muscle activity, moderate to severe lateral canthal lines associated with orbicularis oculi activity, and moderate to severe forehead lines associated with frontalis muscle activity, comprising applying an effective amount of the cosmetic composition of claim 14 to the skin of the subject.

17. A method for: preventing or temporarily improving one or more of the appearance of skin wrinkles, skin laxity, moderate to severe glabellar lines associated with corrugator and/or procerus muscle activity, moderate to severe lateral canthal lines associated with orbicularis oculi activity, and moderate to severe forehead lines associated with *frontalis* muscle activity; treatment of overactive bladder (OAB); treatment of urinary incontinence; prophylaxis of headaches; treatment of spasticity; treatment of cervical dystonia; treatment of hypersalivation; treatment of blepharospasm associated with dystonia; or treatment of strabismus; in a subject, comprising administering an effective amount of the pharmaceutical composition of claim 15 to the subject.

* * * * *

UNITED STATES PATENT AND TRADEMARK OFFICE
CERTIFICATE OF CORRECTION

| | | |
|---|---|---|
| PATENT NO. | : 11,130,782 B2 | Page 1 of 1 |
| APPLICATION NO. | : 16/653724 | |
| DATED | : September 28, 2021 | |
| INVENTOR(S) | : Love | |

It is certified that error appears in the above-identified patent and that said Letters Patent is hereby corrected as shown below:

On the Title Page

Item (54) "NICOTINIC ACETYLCHOLINE RECEPTOR PEPTIDE ANTAGONIST CONOTOXIN COMPOSITIONS AND RELATED METHODS"
Should read:
--NICOTINIC ACETYLCHOLINE RECEPTOR PEPTIDE ANTAGONIST COMPOSITIONS AND RELATED METHODS--

In the Specification

In Column 1, Lines 1-3, "NICOTINIC ACETYLCHOLINE RECEPTOR PEPTIDE ANTAGONIST CONOTOXIN COMPOSITIONS AND RELATED METHODS"
Should read:
--NICOTINIC ACETYLCHOLINE RECEPTOR PEPTIDE ANTAGONIST COMPOSITIONS AND RELATED METHODS--

Signed and Sealed this
First Day of March, 2022

Drew Hirshfeld
*Performing the Functions and Duties of the
Under Secretary of Commerce for Intellectual Property and
Director of the United States Patent and Trademark Office*